(12) United States Patent
Endoh et al.

(10) Patent No.: US 8,003,331 B2
(45) Date of Patent: Aug. 23, 2011

(54) METHOD FOR IDENTIFYING TARGET PROTEIN OF DRUG AND METHOD FOR SCREENING THERAPEUTIC AGENT FOR DIABETES USING THE TARGET PROTEIN

(75) Inventors: Hideki Endoh, Tokyo (JP); Hiroyuki Yokota, Tokyo (JP); Masahiko Hayakawa, Tokyo (JP); Shinji Soga, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 681 days.

(21) Appl. No.: 11/909,031

(22) PCT Filed: Aug. 9, 2006

(86) PCT No.: PCT/JP2006/315745
§ 371 (c)(1),
(2), (4) Date: Sep. 18, 2007

(87) PCT Pub. No.: WO2007/020853
PCT Pub. Date: Feb. 22, 2007

(65) Prior Publication Data
US 2009/0041754 A1 Feb. 12, 2009

(30) Foreign Application Priority Data

Aug. 12, 2005 (JP) ................................. 2005-234673
Sep. 27, 2005 (JP) ................................. 2005-279582

(51) Int. Cl.
*G01N 33/53* (2006.01)
(52) U.S. Cl. ...................................................... 435/7.1
(58) Field of Classification Search ........................ None
See application file for complete search history.

(56) References Cited

U.S. PATENT DOCUMENTS

| | | | |
|---|---|---|---|
| 5,585,277 A | 12/1996 | Bowie et al. | |
| 5,679,582 A | 10/1997 | Bowie et al. | |
| 6,207,401 B1 * | 3/2001 | Plowman et al. | ............... 435/15 |
| 6,579,868 B1 | 6/2003 | Asano et al. | |
| 6,790,958 B2 | 9/2004 | Lum et al. | |
| 7,244,577 B2 * | 7/2007 | Todd et al. | .................. 435/7.21 |
| 2002/0055123 A1 | 5/2002 | Pakula et al. | |
| 2004/0072368 A1 | 4/2004 | Martinez | |
| 2004/0191835 A1 | 9/2004 | Pakula et al. | |

OTHER PUBLICATIONS

Lazar, E., et al. Mol. Cell Biol. 1988;8(3):1247-1252.*
Burgess, W.H., et al. J. Cell Biol. 1990;111:2129-2138.*
Parakhia, R.A., et al. Faseb J. 2009; 23(1):856.16.*
Foretz, M., et al. J. Clin. Invest. 2010;120(7):2355-2369.*
Hatori, H., et al., "FR225659-binding Proteins: Identification as Serine/Threonine Protein Phosphatase PP1 and PP2A Using High-performance Affinity Beads," *The Journal of Antibiotics*, vol. 57, No. 7, Jul. 2004, pp. 456-461.

Teo, S.K., et al., "Thalidomide as a novel therapeutic agent: new uses for an old product," *Drug Discovery Today*, vol. 10, No. 2, Jan. 2005, pp. 107-114.
Lalau, J.D., et al., "Lactic Acidosis in Metformin Therapy," *Drugs*, vol. 58, Suppl. 1, 1999, pp. 55-60 and pp. 75-82.
Shimizu, N., et al., "High-performance affinity beads for identifying drug receptors," *Nature Biotechnology* (England), vol. 18, Aug. 2000, pp. 877-881.
Henthorn, D.C., et al., "A GAL-4 based yeast three-hybrid system for the identification of small molecule-target protein interactions," *Biochemical Pharmacology*, vol. 63, 2002, pp. 1619-1628.
Sche, P.P., et al., "Display clonging: functional identification of natural product receptors using cDNA-phage display," *Chemistry & Biology*, vol. 6, No. 10, 1999, pp. 707-716.
Lehmann, J.M., et al., An Antidiabetic Thiazolidinedione Is a High Affinity Ligand for Peroxisome Proliferator-activated Receptor γ (PPARγ)*, *The Journal of Biological Chemistry* (USA), vol. 270, No. 22, Jun. 2, 1995, pp. 12953-12956.
Noji, H., et al., "Direct observation of the rotation of $F_1$-ATPase," *Nature* (USA), vol. 386, Mar. 20, 1997, pp. 299-302.
Abrahams, J.P., et al., "Structure at 2.8 Å resolution of $F_1$-ATPase from bovine heart mitochondria," *Nature* (USA), vol. 370, Aug. 25, 1994, pp. 621-628.
Gething et al., "Protein folding in the cell," Nature, vol. 355, Jan. 2, 1992, pp. 33-45.
Højlund et al., "Proteome Analysis Reveals Phosphorylation of ATP Synthase β-Subunit in Human Skeletal Muscle and Proteins with Potential roles in Type 2 Diabetes," J. Biological Chemistry, vol. 278, No. 12, Mar. 21, 2003, pp. 10436-10442.
Schäfer, "Some New Aspects on the Interaction of Hypoglycemia-Producing Biguanides with Biological Membranes," Biochemical Pharmacology, vol. 25, No. 18 (1976) pp. 2015-2024.
Sreedhar et al., "Heat shock proteins in the regulation of apoptosis:new strategies in tumor therapy A comprehensive review," Pharmacology & Therapeutics, vol. 101, No. 3, (2004) pp. 227-257.
Sreekumar et al., "Gene Expression Profile in Skeletal Muscle of Type 2 Diabetes and the Effect of Insulin Treatment, Diabetes," vol. 51, Jun. 2002, pp. 1913-1920. Beliakoff, J., et al., "Hormone-Refractory Breast Cancer Remains Sensitive to the Antitumor Activity of Heat Shock Protein 90 Inhibitors", Clinical Cancer Research, Oct. 2003, pp. 4961-4971, vol. 9., No. 13, American Association for Cancer Research, XP002548503.
Rosenhagen, M., "The Heat Shock Protein 90-Targeting Drug Cisplatin Selectively Inhibits Steroid Receptor Activation", Molecular Endocrinology, Oct. 2003, pp. 1991-2001, vol. 17, No. 10, The Endochrine Society, XP002548504.
Tateishi, Y., et al., "Ligand-dependent switching of ubiquitin-proteasome pathways for estrogen receptor", The EMBO Journal, Dec. 2004, pp. 4813-4823, vol. 23, No. 24, European Molecular Biology Organization, XP002548505.
European Office Action in corresponding European Application No. 09075347.6, issued Jun. 23, 2010, European Patent Office.

* cited by examiner

*Primary Examiner* — G. R. Ewoldt
(74) *Attorney, Agent, or Firm* — Sughrue Mion, PLLC

(57) ABSTRACT

A method for identifying a target protein of a compound having a pharmacological action by detecting a tertiary structural change of a target protein by binding a compound having a pharmacological action to a target protein with the use of a molecular chaperone protein having a characteristic of binding to a protein by recognizing a tertiary structural change of the protein is disclosed. Further, a method for screening a therapeutic agent for diabetes using a target protein of biguanide which is a therapeutic agent for diabetes and was found by the identification method, a screening tool which can be used in the screening method and a pharmaceutical composition for treating diabetes containing a substance obtained by the screening method are disclosed.

3 Claims, 5 Drawing Sheets

[Fig. 1]
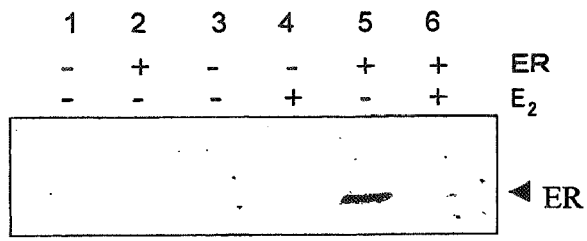
[Fig. 2]
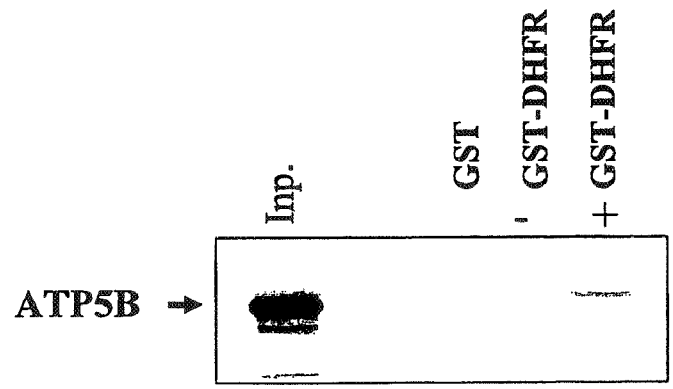
[Fig. 3]
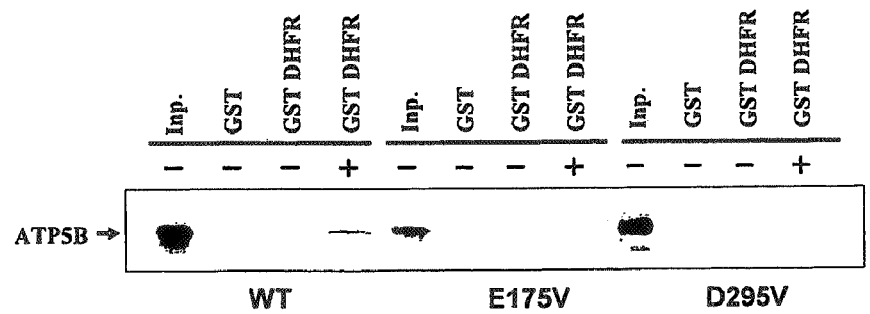

[Fig. 4]
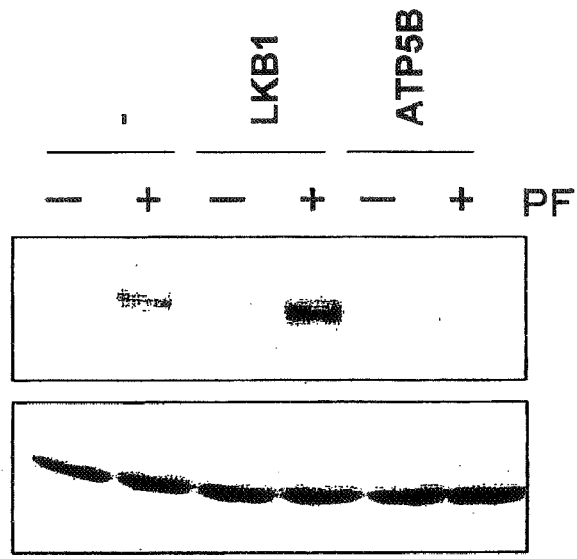
[Fig. 5]
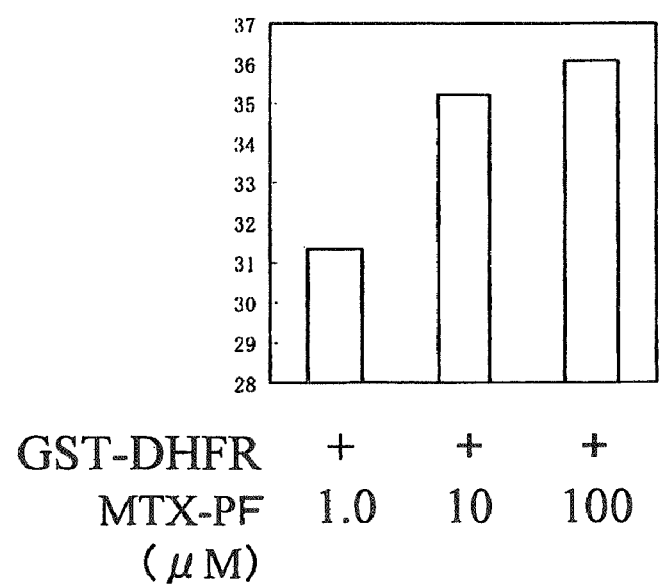

[Fig. 6]
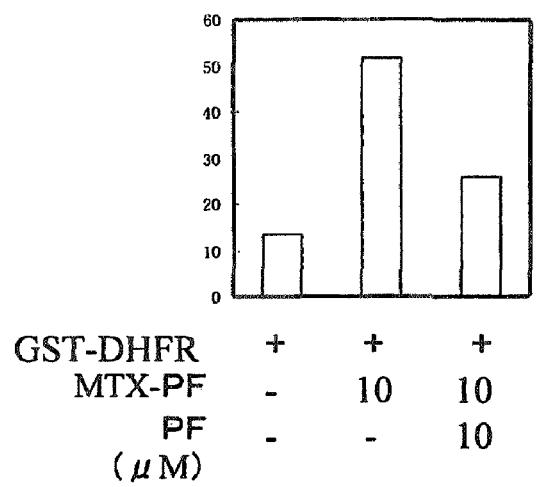
[Fig. 7]
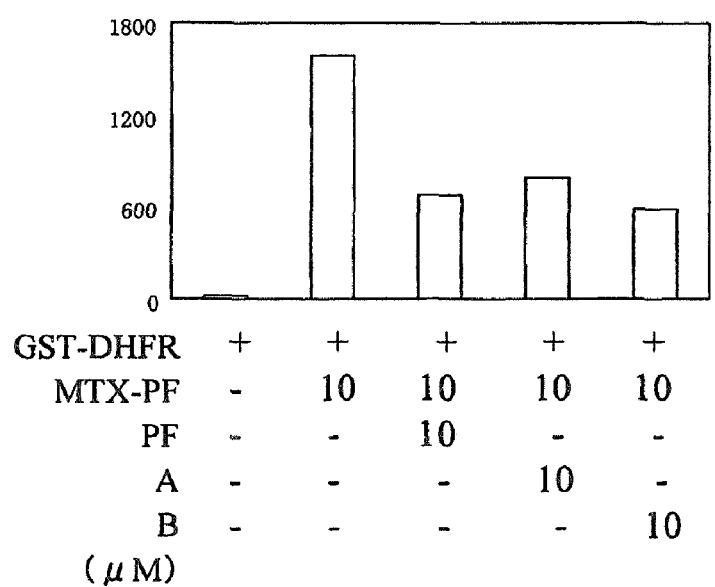

[Fig. 8]
A
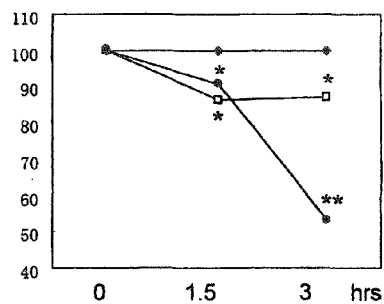
B
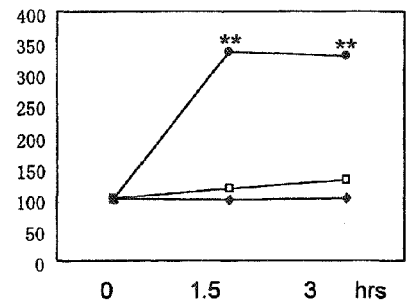
C
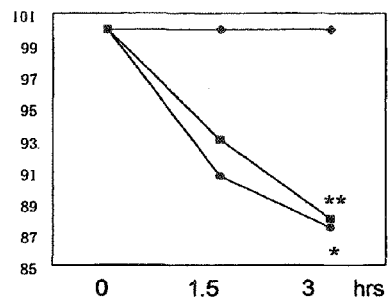
D
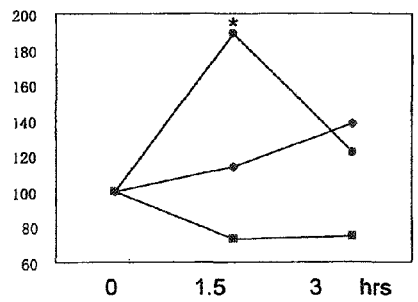
[Fig. 9]
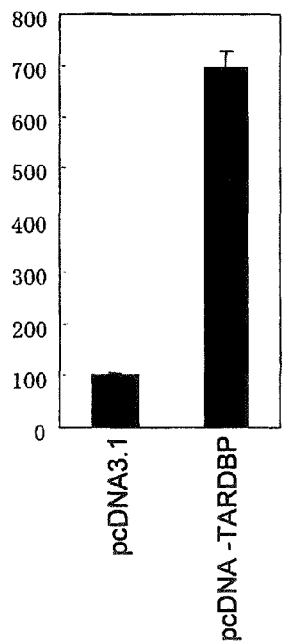

[Fig. 10]
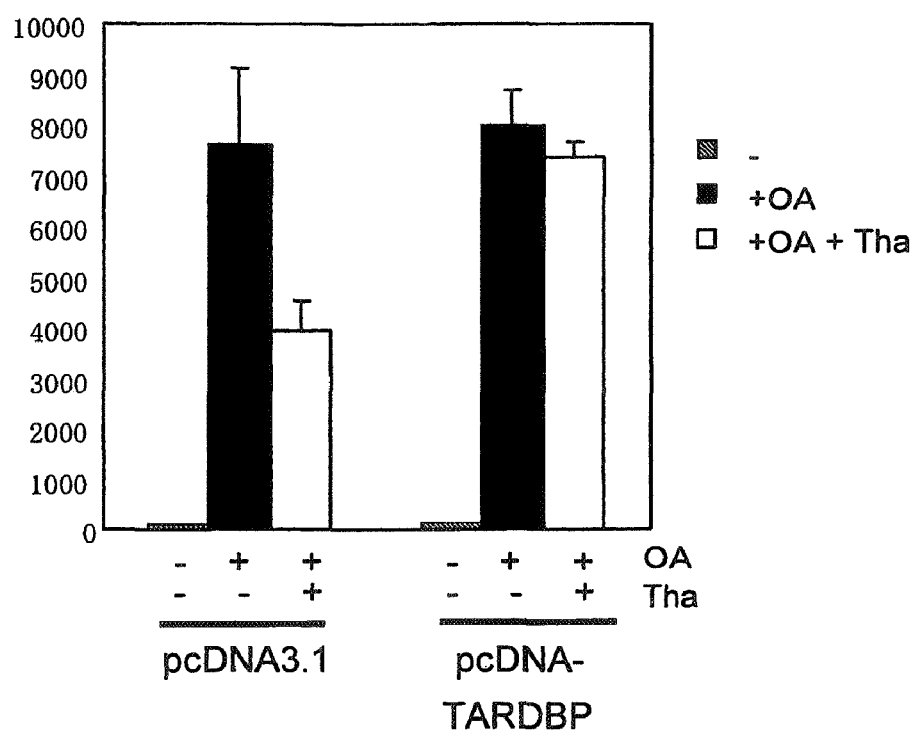

SEQUENCE LISTING

<160> NUMBER OF SEQ ID NOS: 102

<210> SEQ ID NO 1
<211> LENGTH: 1590

```
<212> TYPE: DNA
<213> ORGANISM: Homo sapiens

<400> SEQUENCE: 1
atgttggggt tgtgggtcg ggtggccgct gctccggcct ccggggcctt gcggagactc     60 acccccttcag cgtcgctgcc cccagctcag ctcttactgc gggccgctcc gacggcggtc    120
catcctgtca gggactatgc ggcgcaaaca tctccttcgc caaaagcagg cgccgccacc    180
gggcgcatcg tggcggtcat tggcgcagtg gtggacgtcc agtttgatga gggactacca    240
ccaattctaa atgccctgga agtgcaaggc agggagacca gactggtttt ggaggtggcc    300
cagcatttgg gtgagagcac agtaaggact attgctatgg atggtacaga aggcttggtt    360
agaggccaga aagtactgga ttctggtgca ccaatcaaaa ttcctgttgg tcctgagact    420
ttgggcagaa tcatgaatgt cattggagaa cctattgatg aaagaggtcc catcaaaacc    480
aaacaatttg ctcccattca tgctgaggct ccagagttca tggaaatgag tgttgagcag    540
gaaattctgg tgactggtat caaggttgtc gatctgctag ctccctatgc caagggtggc    600
aaaattgggc ttttggtgg tgctggagtt ggcaagactg tactgatcat ggagttaatc    660
aacaatgtcg ccaaagccca tggtggttac tctgtgtttg ctggtgttgg tgagaggacc    720
cgtgaaggca tgatttata ccatgaaatg attgaatctg gtgttatcaa cttaaaagat    780
gccacctcta aggtagcgct ggtatatggt caaatgaatg aaccacctgg tgctcgtgcc    840
cgggtagctc tgactgggct gactgtggct gaatacttca gagaccaaga aggtcaagat    900
gtactgctat ttattgataa catctttcgc ttcacccagg ctggttcaga ggtgtctgca    960
ttattgggcc gaatcccttc tgctgtgggc tatcagccta ccctggccac tgacatgggt   1020
actatgcagg aaagaattac cactaccaag aagggatcta tcacctctgt acaggctatc   1080
tatgtgcctg ctgatgactt gactgaccct gcccctgcta ctacgtttgc ccatttggat   1140
gctaccactg tactgtcgcg tgccattgct gagctgggca tctatccagc tgtggatcct   1200
ctagactcca cctctcgtat catggatccc aacattgttg gcagtgagca ttacgatgtt   1260
gcccgtgggg tgcaaaagat cctgcaggac tacaaatccc tccaggatat cattgccatc   1320
ctgggtatgg atgaactttc tgaggaagac aagttgaccg tgtcccgtgc acggaaaata   1380
cagcgtttct tgtctcagcc attccaggtt gctgaggtct tcacaggtca tatggggaag   1440
ctggtacccc tgaaggagac catcaaagga ttccagcaga ttttggcagg tgaatatgac   1500
catctcccag aacaggcctt ctatatggtg ggacccattg aagaagctgt ggcaaaagct   1560
gataagctgg ctgaagagca ttcatcgtga                                     1590

<210> SEQ ID NO 2
<211> LENGTH: 529
<212> TYPE: PRT
<213> ORGANISM: Homo sapiens

<400> SEQUENCE: 2

Met Leu Gly Phe Val Gly Arg Val Ala Ala Pro Ala Ser Gly Ala
1               5                   10                  15

Leu Arg Arg Leu Thr Pro Ser Ala Ser Leu Pro Pro Ala Gln Leu Leu
                20                  25                  30

Leu Arg Ala Ala Pro Thr Ala Val His Pro Val Arg Asp Tyr Ala Ala
            35                  40                  45

Gln Thr Ser Pro Ser Pro Lys Ala Gly Ala Ala Thr Gly Arg Ile Val
        50                  55                  60

Ala Val Ile Gly Ala Val Val Asp Val Gln Phe Asp Glu Gly Leu Pro
```

-continued

```
               65                  70                  75                  80
          Pro Ile Leu Asn Ala Leu Glu Val Gln Gly Arg Glu Thr Arg Leu Val
                           85                  90                  95

Leu Glu Val Ala Gln His Leu Gly Glu Ser Thr Val Arg Thr Ile Ala
                          100                 105                 110

Met Asp Gly Thr Glu Gly Leu Arg Gly Gln Lys Val Leu Asp Ser
                      115                 120                 125

Gly Ala Pro Ile Lys Ile Pro Val Gly Pro Glu Thr Leu Gly Arg Ile
                      130                 135                 140

Met Asn Val Ile Gly Glu Pro Ile Asp Glu Arg Gly Pro Ile Lys Thr
          145                 150                 155                 160

Lys Gln Phe Ala Pro Ile His Ala Glu Ala Pro Glu Phe Met Glu Met
                          165                 170                 175

Ser Val Glu Gln Glu Ile Leu Val Thr Gly Ile Lys Val Val Asp Leu
                      180                 185                 190

Leu Ala Pro Tyr Ala Lys Gly Gly Lys Ile Gly Leu Phe Gly Gly Ala
                      195                 200                 205

Gly Val Gly Lys Thr Val Leu Ile Met Glu Leu Ile Asn Asn Val Ala
                      210                 215                 220

Lys Ala His Gly Gly Tyr Ser Val Phe Ala Gly Val Gly Glu Arg Thr
          225                 230                 235                 240

Arg Glu Gly Asn Asp Leu Tyr His Glu Met Ile Glu Ser Gly Val Ile
                          245                 250                 255

Asn Leu Lys Asp Ala Thr Ser Lys Val Ala Leu Val Tyr Gly Gln Met
                      260                 265                 270

Asn Glu Pro Pro Gly Ala Arg Ala Arg Val Ala Leu Thr Gly Leu Thr
                      275                 280                 285

Val Ala Glu Tyr Phe Arg Asp Gln Glu Gly Gln Asp Val Leu Leu Phe
                      290                 295                 300

Ile Asp Asn Ile Phe Arg Phe Thr Gln Ala Gly Ser Glu Val Ser Ala
          305                 310                 315                 320

Leu Leu Gly Arg Ile Pro Ser Ala Val Gly Tyr Gln Pro Thr Leu Ala
                          325                 330                 335

Thr Asp Met Gly Thr Met Gln Glu Arg Ile Thr Thr Lys Lys Gly
                      340                 345                 350

Ser Ile Thr Ser Val Gln Ala Ile Tyr Val Pro Ala Asp Asp Leu Thr
                      355                 360                 365

Asp Pro Ala Pro Ala Thr Thr Phe Ala His Leu Asp Ala Thr Thr Val
                      370                 375                 380

Leu Ser Arg Ala Ile Ala Glu Leu Gly Ile Tyr Pro Ala Val Asp Pro
          385                 390                 395                 400

Leu Asp Ser Thr Ser Arg Ile Met Asp Pro Asn Ile Val Gly Ser Glu
                          405                 410                 415

His Tyr Asp Val Ala Arg Gly Val Gln Lys Ile Leu Gln Asp Tyr Lys
                      420                 425                 430

Ser Leu Gln Asp Ile Ile Ala Ile Leu Gly Met Asp Glu Leu Ser Glu
                      435                 440                 445

Glu Asp Lys Leu Thr Val Ser Arg Ala Arg Lys Ile Gln Arg Phe Leu
                      450                 455                 460

Ser Gln Pro Phe Gln Val Ala Glu Val Phe Thr Gly His Met Gly Lys
          465                 470                 475                 480

Leu Val Pro Leu Lys Glu Thr Ile Lys Gly Phe Gln Gln Ile Leu Ala
                          485                 490                 495
```

Gly Glu Tyr Asp His Leu Pro Glu Gln Ala Phe Tyr Met Val Gly Pro
            500                 505                 510

Ile Glu Glu Ala Val Ala Lys Ala Asp Lys Leu Ala Glu Glu His Ser
        515                 520                 525

Ser

<210> SEQ ID NO 3
<211> LENGTH: 641
<212> TYPE: PRT
<213> ORGANISM: Homo sapiens

<400> SEQUENCE: 3

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Asp Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp

```
                    340                 345                 350
        Phe Phe Asn Gly Arg Asp Leu Asn Lys Ser Ile Asn Pro Asp Glu Ala
                355                 360                 365

Val Ala Tyr Gly Ala Ala Val Gln Ala Ala Ile Leu Met Gly Asp Lys
            370                 375                 380

Ser Glu Asn Val Gln Asp Leu Leu Leu Asp Val Ala Pro Leu Ser
        385                 390                 395                 400

Leu Gly Leu Glu Thr Ala Gly Gly Val Met Thr Ala Leu Ile Lys Arg
                        405                 410                 415

Asn Ser Thr Ile Pro Thr Lys Gln Thr Gln Ile Phe Thr Thr Tyr Ser
                    420                 425                 430

Asp Asn Gln Pro Gly Val Leu Ile Gln Val Tyr Glu Gly Glu Arg Ala
                435                 440                 445

Met Thr Lys Asp Asn Asn Leu Leu Gly Arg Phe Glu Leu Ser Gly Ile
            450                 455                 460

Pro Pro Ala Pro Arg Gly Val Pro Gln Ile Glu Val Thr Phe Asp Ile
        465                 470                 475                 480

Asp Ala Asn Gly Ile Leu Asn Val Thr Ala Thr Asp Lys Ser Thr Gly
                        485                 490                 495

Lys Ala Asn Lys Ile Thr Ile Thr Asn Asp Lys Gly Arg Leu Ser Lys
                    500                 505                 510

Glu Glu Ile Glu Arg Met Val Gln Glu Ala Lys Tyr Lys Ala Glu
                515                 520                 525

Asp Glu Val Gln Arg Glu Arg Val Ser Ala Lys Asn Ala Leu Glu Ser
            530                 535                 540

Tyr Ala Phe Asn Met Lys Ser Ala Val Glu Asp Glu Gly Leu Lys Gly
        545                 550                 555                 560

Lys Ile Ser Glu Ala Asp Lys Lys Lys Val Leu Asp Lys Cys Gln Glu
                        565                 570                 575

Val Ile Ser Trp Leu Asp Ala Asn Thr Leu Ala Glu Lys Asp Glu Phe
                    580                 585                 590

Glu His Lys Arg Lys Glu Leu Glu Gln Val Cys Asn Pro Ile Ile Ser
                595                 600                 605

Gly Leu Tyr Gln Gly Ala Gly Gly Pro Gly Pro Gly Gly Phe Gly Ala
            610                 615                 620

Gln Gly Pro Lys Gly Gly Ser Gly Ser Gly Pro Thr Ile Glu Glu Val
        625                 630                 635                 640

Asp

<210> SEQ ID NO 4
<211> LENGTH: 858
<212> TYPE: PRT
<213> ORGANISM: Homo sapiens

<400> SEQUENCE: 4

Met Ser Val Val Gly Leu Asp Val Gly Ser Gln Ser Cys Tyr Ile Ala
1               5                   10                  15

Val Ala Arg Ala Gly Gly Ile Glu Thr Ile Ala Asn Glu Phe Ser Asp
            20                  25                  30

Arg Cys Thr Pro Ser Val Ile Ser Phe Gly Ser Lys Asn Arg Thr Ile
        35                  40                  45

Gly Val Ala Ala Lys Asn Gln Gln Ile Thr His Ala Asn Asn Thr Val
    50                  55                  60

Ser Asn Phe Lys Arg Phe His Gly Arg Ala Phe Asn Asp Pro Phe Ile
65                  70                  75                  80
```

```
Gln Lys Glu Lys Glu Asn Leu Ser Tyr Asp Leu Val Pro Leu Lys Asn
                85                  90                  95
Gly Gly Val Gly Ile Lys Val Met Tyr Met Gly Glu His Leu Phe
            100                 105                 110
Ser Val Glu Gln Ile Thr Ala Met Leu Leu Thr Lys Leu Lys Glu Thr
            115                 120                 125
Ala Glu Asn Ser Leu Lys Lys Pro Val Thr Asp Cys Val Ile Ser Val
130                 135                 140
Pro Ser Phe Phe Thr Asp Ala Glu Arg Arg Ser Val Leu Asp Ala Ala
145                 150                 155                 160
Gln Ile Val Gly Leu Asn Cys Leu Arg Leu Met Asn Asp Met Thr Ala
                165                 170                 175
Val Ala Leu Asn Tyr Gly Ile Tyr Lys Gln Asp Leu Pro Ser Leu Asp
            180                 185                 190
Glu Lys Pro Arg Ile Val Val Phe Val Asp Met Gly His Ser Ala Phe
            195                 200                 205
Gln Val Ser Ala Cys Ala Phe Asn Lys Gly Lys Leu Lys Val Leu Gly
210                 215                 220
Thr Ala Phe Asp Pro Phe Leu Gly Gly Lys Asn Phe Asp Glu Lys Leu
225                 230                 235                 240
Val Glu His Phe Cys Ala Glu Phe Lys Thr Lys Tyr Lys Leu Asp Ala
                245                 250                 255
Lys Ser Lys Ile Arg Ala Leu Leu Arg Leu Tyr Gln Glu Cys Glu Lys
            260                 265                 270
Leu Lys Lys Leu Met Ser Ser Asn Ser Thr Asp Leu Pro Leu Asn Ile
            275                 280                 285
Glu Cys Phe Met Asn Asp Lys Asp Val Ser Gly Lys Met Asn Arg Ser
290                 295                 300
Gln Phe Glu Glu Leu Cys Ala Glu Leu Leu Gln Lys Ile Glu Val Pro
305                 310                 315                 320
Leu Tyr Ser Leu Leu Glu Gln Thr His Leu Lys Val Glu Asp Val Ser
                325                 330                 335
Ala Val Glu Ile Val Gly Gly Ala Thr Arg Ile Pro Ala Val Lys Glu
            340                 345                 350
Arg Ile Ala Lys Phe Phe Gly Lys Asp Ile Ser Thr Thr Leu Asn Ala
            355                 360                 365
Asp Glu Ala Val Ala Arg Gly Cys Ala Leu Gln Cys Ala Ile Leu Ser
370                 375                 380
Pro Ala Phe Lys Val Arg Glu Phe Ser Val Thr Asp Ala Val Pro Phe
385                 390                 395                 400
Pro Ile Ser Leu Ile Trp Asn His Asp Ser Glu Asp Thr Glu Gly Val
                405                 410                 415
His Glu Val Phe Ser Arg Asn His Ala Ala Pro Phe Ser Lys Val Leu
            420                 425                 430
Thr Phe Leu Arg Arg Gly Pro Phe Glu Leu Glu Ala Phe Tyr Ser Asp
            435                 440                 445
Pro Gln Gly Val Pro Tyr Pro Glu Ala Lys Ile Gly Arg Phe Val Val
450                 455                 460
Gln Asn Val Ser Ala Gln Lys Asp Gly Glu Lys Ser Arg Val Lys Val
465                 470                 475                 480
Lys Val Arg Val Asn Thr His Gly Ile Phe Thr Ile Ser Thr Ala Ser
                485                 490                 495
Met Val Glu Lys Val Pro Thr Glu Glu Asn Glu Met Ser Ser Glu Ala
```

```
                500             505             510
Asp Met Glu Cys Leu Asn Gln Arg Pro Pro Glu Asn Pro Asp Thr Asp
            515                 520                 525

Lys Asn Val Gln Gln Asp Asn Ser Glu Ala Gly Thr Gln Pro Gln Val
        530                 535                 540

Gln Thr Asp Ala Gln Thr Ser Gln Ser Pro Pro Ser Pro Glu Leu
545                 550                 555                 560

Thr Ser Glu Glu Asn Lys Ile Pro Asp Ala Asp Lys Ala Asn Glu Lys
                565                 570                 575

Lys Val Asp Gln Pro Pro Glu Ala Lys Lys Pro Lys Ile Lys Val Val
            580                 585                 590

Asn Val Glu Leu Pro Ile Glu Ala Asn Leu Val Trp Gln Leu Gly Lys
        595                 600                 605

Asp Leu Leu Asn Met Tyr Ile Glu Thr Glu Gly Lys Met Ile Met Gln
610                 615                 620

Asp Lys Leu Glu Lys Glu Arg Asn Asp Ala Lys Asn Ala Val Glu Glu
625                 630                 635                 640

Tyr Val Tyr Glu Phe Arg Asp Lys Leu Cys Gly Pro Tyr Glu Lys Phe
                645                 650                 655

Ile Cys Glu Gln Asp His Gln Asn Phe Leu Arg Leu Leu Thr Glu Thr
            660                 665                 670

Glu Asp Trp Leu Tyr Glu Gly Glu Asp Gln Ala Lys Gln Ala Tyr
        675                 680                 685

Val Asp Lys Leu Glu Glu Leu Met Lys Ile Gly Thr Pro Val Lys Val
        690                 695                 700

Arg Phe Gln Glu Ala Glu Arg Pro Lys Met Phe Glu Glu Leu Gly
705                 710                 715                 720

Gln Arg Leu Gln His Tyr Ala Lys Ile Ala Ala Asp Phe Arg Asn Lys
                725                 730                 735

Asp Glu Lys Tyr Asn His Ile Asp Glu Ser Met Lys Lys Val Glu
            740                 745                 750

Lys Ser Val Asn Glu Val Met Glu Trp Met Asn Asn Val Met Asn Ala
        755                 760                 765

Gln Ala Lys Lys Ser Leu Asp Gln Asp Pro Val Val Arg Ala Gln Glu
770                 775                 780

Ile Lys Thr Lys Ile Lys Glu Leu Asn Asn Thr Cys Glu Pro Val Val
785                 790                 795                 800

Thr Gln Pro Lys Pro Lys Ile Glu Ser Pro Lys Leu Glu Arg Thr Pro
                805                 810                 815

Asn Gly Pro Asn Ile Asp Lys Lys Glu Glu Asp Leu Glu Asp Lys Asn
            820                 825                 830

Asn Phe Gly Ala Glu Pro Pro His Gln Asn Gly Glu Cys Tyr Pro Asn
        835                 840                 845

Glu Lys Asn Ser Val Asn Met Asp Leu Asp
        850                 855

<210> SEQ ID NO 5
<211> LENGTH: 732
<212> TYPE: PRT
<213> ORGANISM: Homo sapiens

<400> SEQUENCE: 5

Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
```

-continued

```
                20                  25                  30
Ile Ile Asn Thr Phe Tyr Ser Asn Lys Glu Ile Phe Leu Arg Glu Leu
            35                  40                  45
Ile Ser Asn Ser Ser Asp Ala Leu Asp Lys Ile Arg Tyr Glu Thr Leu
        50                  55                  60
Thr Asp Pro Ser Lys Leu Asp Ser Gly Lys Glu Leu His Ile Asn Leu
65                  70                  75                  80
Ile Pro Asn Lys Gln Asp Arg Thr Leu Thr Ile Val Asp Thr Gly Ile
                85                  90                  95
Gly Met Thr Lys Ala Asp Leu Ile Asn Asn Leu Gly Thr Ile Ala Lys
            100                 105                 110
Ser Gly Thr Lys Ala Phe Met Glu Ala Leu Gln Ala Gly Ala Asp Ile
        115                 120                 125
Ser Met Ile Gly Gln Phe Gly Val Gly Phe Tyr Ser Ala Tyr Leu Val
    130                 135                 140
Ala Glu Lys Val Thr Val Ile Thr Lys His Asn Asp Asp Glu Gln Tyr
145                 150                 155                 160
Ala Trp Glu Ser Ser Ala Gly Gly Ser Phe Thr Val Arg Thr Asp Thr
                165                 170                 175
Gly Glu Pro Met Gly Arg Gly Thr Lys Val Ile Leu His Leu Lys Glu
            180                 185                 190
Asp Gln Thr Glu Tyr Leu Glu Glu Arg Arg Ile Lys Glu Ile Val Lys
        195                 200                 205
Lys His Ser Gln Phe Ile Gly Tyr Pro Ile Thr Leu Phe Val Glu Lys
    210                 215                 220
Glu Arg Asp Lys Glu Val Ser Asp Asp Glu Ala Glu Glu Lys Glu Asp
225                 230                 235                 240
Lys Glu Glu Glu Lys Glu Lys Glu Glu Lys Glu Ser Glu Asp Lys Pro
                245                 250                 255
Glu Ile Glu Asp Val Gly Ser Asp Glu Glu Glu Lys Lys Asp Gly
            260                 265                 270
Asp Lys Lys Lys Lys Lys Ile Lys Glu Lys Tyr Ile Asp Gln Glu
        275                 280                 285
Glu Leu Asn Lys Thr Lys Pro Ile Trp Thr Arg Asn Pro Asp Asp Ile
    290                 295                 300
Thr Asn Glu Glu Tyr Gly Glu Phe Tyr Lys Ser Leu Thr Asn Asp Trp
305                 310                 315                 320
Glu Asp His Leu Ala Val Lys His Phe Ser Val Glu Gly Gln Leu Glu
                325                 330                 335
Phe Arg Ala Leu Leu Phe Val Pro Arg Arg Ala Pro Phe Asp Leu Phe
            340                 345                 350
Glu Asn Arg Lys Lys Lys Asn Asn Ile Lys Leu Tyr Val Arg Arg Val
        355                 360                 365
Phe Ile Met Asp Asn Cys Glu Glu Leu Ile Pro Glu Tyr Leu Asn Phe
    370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
                405                 410                 415
Val Lys Lys Cys Leu Glu Leu Phe Thr Glu Leu Ala Glu Asp Lys Glu
            420                 425                 430
Asn Tyr Lys Lys Phe Tyr Glu Gln Phe Ser Lys Asn Ile Lys Leu Gly
        435                 440                 445
```

```
Ile His Glu Asp Ser Gln Asn Arg Lys Lys Leu Ser Glu Leu Leu Arg
450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
                500                 505                 510

Lys His Gly Leu Glu Val Ile Tyr Met Ile Glu Pro Ile Asp Glu Tyr
                515                 520                 525

Cys Val Gln Gln Leu Lys Glu Phe Glu Gly Lys Thr Leu Val Ser Val
530                 535                 540

Thr Lys Glu Gly Leu Glu Leu Pro Glu Asp Glu Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Val Ser Asn Arg Leu
                580                 585                 590

Val Thr Ser Pro Cys Cys Ile Val Thr Ser Thr Tyr Gly Trp Thr Ala
                595                 600                 605

Asn Met Glu Arg Ile Met Lys Ala Gln Ala Leu Arg Asp Asn Ser Thr
                610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
                660                 665                 670

Ser Ser Gly Phe Ser Leu Glu Asp Pro Gln Thr His Ala Asn Arg Ile
                675                 680                 685

Tyr Arg Met Ile Lys Leu Gly Leu Gly Ile Asp Glu Asp Pro Thr
                690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

<210> SEQ ID NO 6
<211> LENGTH: 573
<212> TYPE: PRT
<213> ORGANISM: Homo sapiens

<400> SEQUENCE: 6

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
            35                  40                  45

Asp Ala Val Ala Val Thr Met Gly Pro Lys Gly Arg Thr Val Ile Ile
        50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95
```

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
            115                 120                 125

Glu Lys Ile Ser Lys Gly Ala Asn Pro Val Glu Ile Arg Arg Gly Val
130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
            165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
            195                 200                 205

Asp Glu Leu Glu Ile Ile Glu Gly Met Lys Phe Asp Arg Gly Tyr Ile
            210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
            245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
            275                 280                 285

Asn Arg Leu Lys Val Gly Leu Gln Val Val Ala Val Lys Ala Pro Gly
            290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
            325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
            355                 360                 365

Lys Arg Ile Gln Glu Ile Ile Glu Gln Leu Asp Val Thr Thr Ser Glu
            370                 375                 380

Tyr Glu Lys Glu Lys Leu Asn Glu Arg Leu Ala Lys Leu Ser Asp Gly
385                 390                 395                 400

Val Ala Val Leu Lys Val Gly Thr Ser Asp Val Glu Val Asn Glu
            405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
            435                 440                 445

Pro Ala Leu Asp Ser Leu Thr Pro Ala Asn Glu Asp Gln Lys Ile Gly
            450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
            485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
            515                 520                 525

```
Leu Leu Asp Ala Ala Gly Val Ala Ser Leu Leu Thr Thr Ala Glu Val
            530                 535                 540

Val Val Thr Glu Ile Pro Lys Glu Glu Lys Asp Pro Gly Met Gly Ala
545                 550                 555                 560

Met Gly Gly Met Gly Gly Met Gly Gly Met Phe
            565                 570

<210> SEQ ID NO 7
<211> LENGTH: 397
<212> TYPE: PRT
<213> ORGANISM: Homo sapiens

<400> SEQUENCE: 7

Met Val Lys Glu Thr Thr Tyr Tyr Asp Val Leu Gly Val Lys Pro Asn
1               5                   10                  15

Ala Thr Gln Glu Glu Leu Lys Lys Ala Tyr Arg Lys Leu Ala Leu Lys
            20                  25                  30

Tyr His Pro Asp Lys Asn Pro Asn Glu Gly Glu Lys Phe Lys Gln Ile
        35                  40                  45

Ser Gln Ala Tyr Glu Val Leu Ser Asp Ala Lys Lys Arg Glu Leu Tyr
    50                  55                  60

Asp Lys Gly Gly Glu Gln Ala Ile Lys Glu Gly Gly Ala Gly Gly Gly
65                  70                  75                  80

Phe Gly Ser Pro Met Asp Ile Phe Asp Met Phe Phe Gly Gly Gly Gly
                85                  90                  95

Arg Met Gln Arg Glu Arg Arg Gly Lys Asn Val Val His Gln Leu Ser
            100                 105                 110

Val Thr Leu Glu Asp Leu Tyr Asn Gly Ala Thr Arg Lys Leu Ala Leu
        115                 120                 125

Gln Lys Asn Val Ile Cys Asp Lys Cys Glu Gly Arg Gly Gly Lys Lys
    130                 135                 140

Gly Ala Val Glu Cys Cys Pro Asn Cys Arg Gly Thr Gly Met Gln Ile
145                 150                 155                 160

Arg Ile His Gln Ile Gly Pro Gly Met Val Gln Gln Ile Gln Ser Val
                165                 170                 175

Cys Met Glu Cys Gln Gly His Gly Glu Arg Ile Ser Pro Lys Asp Arg
            180                 185                 190

Cys Lys Ser Cys Asn Gly Arg Lys Ile Val Arg Glu Lys Lys Ile Leu
        195                 200                 205

Glu Val His Ile Asp Lys Gly Met Lys Asp Gly Gln Lys Ile Thr Phe
    210                 215                 220

His Gly Glu Gly Asp Gln Glu Pro Gly Leu Glu Pro Gly Asp Ile Ile
225                 230                 235                 240

Ile Val Leu Asp Gln Lys Asp His Ala Val Phe Thr Arg Arg Gly Glu
                245                 250                 255

Asp Leu Phe Met Cys Met Asp Ile Gln Leu Val Glu Ala Leu Cys Gly
            260                 265                 270

Phe Gln Lys Pro Ile Ser Thr Leu Asp Asn Arg Thr Ile Val Ile Thr
        275                 280                 285

Ser His Pro Gly Gln Ile Val Lys His Gly Asp Ile Lys Cys Val Leu
    290                 295                 300

Asn Glu Gly Met Pro Ile Tyr Arg Arg Pro Tyr Glu Lys Gly Arg Leu
305                 310                 315                 320

Ile Ile Glu Phe Lys Val Asn Phe Pro Glu Asn Gly Phe Leu Ser Pro
                325                 330                 335
```

```
Asp Lys Leu Ser Leu Leu Glu Lys Leu Leu Pro Glu Arg Lys Glu Val
            340                 345                 350

Glu Glu Thr Asp Glu Met Asp Gln Val Glu Leu Val Asp Phe Asp Pro
        355                 360                 365

Asn Gln Glu Arg Arg His Tyr Asn Gly Glu Ala Tyr Glu Asp Asp
    370                 375                 380

Glu His His Pro Arg Gly Gly Val Gln Cys Gln Thr Ser
385                 390                 395

<210> SEQ ID NO 8
<211> LENGTH: 205
<212> TYPE: PRT
<213> ORGANISM: Homo sapiens

<400> SEQUENCE: 8

Met Thr Glu Arg Arg Val Pro Phe Ser Leu Leu Arg Gly Pro Ser Trp
1               5                   10                  15

Asp Pro Phe Arg Asp Trp Tyr Pro His Ser Arg Leu Phe Asp Gln Ala
            20                  25                  30

Phe Gly Leu Pro Arg Leu Pro Glu Glu Trp Ser Gln Trp Leu Gly Gly
        35                  40                  45

Ser Ser Trp Pro Gly Tyr Val Arg Pro Leu Pro Pro Ala Ala Ile Glu
50                  55                  60

Ser Pro Ala Val Ala Ala Pro Ala Tyr Ser Arg Ala Leu Ser Arg Gln
65                  70                  75                  80

Leu Ser Ser Gly Val Ser Glu Ile Arg His Thr Ala Asp Arg Trp Arg
                85                  90                  95

Val Ser Leu Asp Val Asn His Phe Ala Pro Asp Glu Leu Thr Val Lys
            100                 105                 110

Thr Lys Asp Gly Val Val Glu Ile Thr Gly Lys His Glu Glu Arg Gln
        115                 120                 125

Asp Glu His Gly Tyr Ile Ser Arg Cys Phe Thr Arg Lys Tyr Thr Leu
    130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
            180                 185                 190

Gly Pro Glu Ala Ala Lys Ser Asp Glu Thr Ala Ala Lys
        195                 200                 205

<210> SEQ ID NO 9
<211> LENGTH: 102
<212> TYPE: PRT
<213> ORGANISM: Homo sapiens

<400> SEQUENCE: 9

Met Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
50                  55                  60
```

Val Lys Val Gly Asp Lys Val Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 10
<211> LENGTH: 840
<212> TYPE: PRT
<213> ORGANISM: Homo sapiens

<400> SEQUENCE: 10

Met Ser Val Val Gly Ile Asp Leu Gly Phe Gln Ser Cys Tyr Val Ala
1               5                   10                  15

Val Ala Arg Ala Gly Gly Ile Glu Thr Ile Ala Asn Glu Tyr Ser Asp
                20                  25                  30

Arg Cys Thr Pro Ala Cys Ile Ser Phe Gly Pro Lys Asn Arg Ser Ile
            35                  40                  45

Gly Ala Ala Ala Lys Ser Gln Val Ile Ser Asn Ala Lys Asn Thr Val
        50                  55                  60

Gln Gly Phe Lys Arg Phe His Gly Arg Ala Phe Ser Asp Pro Phe Val
65                  70                  75                  80

Glu Ala Glu Lys Ser Asn Leu Ala Tyr Asp Ile Val Gln Leu Pro Thr
                85                  90                  95

Gly Leu Thr Gly Ile Lys Val Thr Tyr Met Glu Glu Glu Arg Asn Phe
            100                 105                 110

Thr Thr Glu Gln Val Thr Ala Met Leu Leu Ser Lys Leu Lys Glu Thr
        115                 120                 125

Ala Glu Ser Val Leu Lys Lys Pro Val Val Asp Cys Val Val Ser Val
130                 135                 140

Pro Cys Phe Tyr Thr Asp Ala Glu Arg Arg Ser Val Met Asp Ala Thr
145                 150                 155                 160

Gln Ile Ala Gly Leu Asn Cys Leu Arg Leu Met Asn Glu Thr Thr Ala
                165                 170                 175

Val Ala Leu Ala Tyr Gly Ile Tyr Lys Gln Asp Leu Pro Ala Leu Glu
            180                 185                 190

Glu Lys Pro Arg Asn Val Val Phe Val Asp Met Gly His Ser Ala Tyr
        195                 200                 205

Gln Val Ser Val Cys Ala Phe Asn Arg Gly Lys Leu Lys Val Leu Ala
210                 215                 220

Thr Ala Phe Asp Thr Thr Leu Gly Gly Arg Lys Phe Asp Glu Val Leu
225                 230                 235                 240

Val Asn His Phe Cys Glu Glu Phe Gly Lys Lys Tyr Lys Leu Asp Ile
                245                 250                 255

Lys Ser Lys Ile Arg Ala Leu Leu Arg Leu Ser Gln Glu Cys Glu Lys
            260                 265                 270

Leu Lys Lys Leu Met Ser Ala Asn Ala Ser Asp Leu Pro Leu Ser Ile
        275                 280                 285

Glu Cys Phe Met Asn Asp Val Asp Val Ser Gly Thr Met Asn Arg Gly
290                 295                 300

Lys Phe Leu Glu Met Cys Asn Asp Leu Leu Ala Arg Val Glu Pro Pro
305                 310                 315                 320

Leu Arg Ser Val Leu Glu Gln Thr Lys Leu Lys Lys Glu Asp Ile Tyr
                325                 330                 335

```
                            -continued
Ala Val Glu Ile Val Gly Gly Ala Thr Arg Ile Pro Ala Val Lys Glu
            340                 345                 350

Lys Ile Ser Lys Phe Phe Gly Lys Glu Leu Ser Thr Thr Leu Asn Ala
        355                 360                 365

Asp Glu Ala Val Thr Arg Gly Cys Ala Leu Gln Cys Ala Ile Leu Ser
    370                 375                 380

Pro Ala Phe Lys Val Arg Glu Phe Ser Ile Thr Asp Val Val Pro Tyr
385                 390                 395                 400

Pro Ile Ser Leu Arg Trp Asn Ser Pro Ala Glu Gly Ser Ser Asp
            405                 410                 415

Cys Glu Val Phe Ser Lys Asn His Ala Ala Pro Phe Ser Lys Val Leu
            420                 425                 430

Thr Phe Tyr Arg Lys Glu Pro Phe Thr Leu Glu Ala Tyr Tyr Ser Ser
        435                 440                 445

Pro Gln Asp Leu Pro Tyr Pro Asp Pro Ala Ile Ala Gln Phe Ser Val
    450                 455                 460

Gln Lys Val Thr Pro Gln Ser Asp Gly Ser Ser Lys Val Lys Val
465                 470                 475                 480

Lys Val Arg Val Asn Val His Gly Ile Phe Ser Val Ser Ser Ala Ser
            485                 490                 495

Leu Val Glu Val His Lys Ser Glu Glu Asn Glu Glu Pro Met Glu Thr
            500                 505                 510

Asp Gln Asn Ala Lys Glu Glu Lys Met Gln Val Asp Gln Glu Glu
    515                 520                 525

Pro His Val Glu Glu Gln Gln Gln Thr Pro Ala Glu Asn Lys Ala
    530                 535                 540

Glu Ser Glu Glu Met Glu Thr Ser Gln Ala Gly Ser Lys Asp Lys Lys
545                 550                 555                 560

Met Asp Gln Pro Pro Gln Ala Lys Lys Ala Lys Val Lys Thr Ser Thr
            565                 570                 575

Val Asp Leu Pro Ile Glu Asn Gln Leu Leu Trp Gln Ile Asp Arg Glu
            580                 585                 590

Met Leu Asn Leu Tyr Ile Glu Asn Glu Gly Lys Met Ile Met Gln Asp
        595                 600                 605

Lys Leu Glu Lys Glu Arg Asn Asp Ala Lys Asn Ala Val Glu Glu Tyr
    610                 615                 620

Val Tyr Glu Met Arg Asp Lys Leu Ser Gly Glu Tyr Glu Lys Phe Val
625                 630                 635                 640

Ser Glu Asp Asp Arg Asn Ser Phe Thr Leu Lys Leu Glu Asp Thr Glu
            645                 650                 655

Asn Trp Leu Tyr Glu Asp Gly Glu Asp Gln Pro Lys Gln Val Tyr Val
            660                 665                 670

Asp Lys Leu Ala Glu Leu Lys Asn Leu Gly Gln Pro Ile Lys Ile Arg
        675                 680                 685

Phe Gln Glu Ser Glu Glu Arg Pro Lys Leu Phe Glu Glu Leu Gly Lys
    690                 695                 700

Gln Ile Gln Gln Tyr Met Lys Ile Ile Ser Ser Phe Lys Asn Lys Glu
705                 710                 715                 720

Asp Gln Tyr Asp His Leu Asp Ala Ala Asp Met Thr Lys Val Glu Lys
            725                 730                 735

Ser Thr Asn Glu Ala Met Glu Trp Met Asn Asn Lys Leu Asn Leu Gln
            740                 745                 750

Asn Lys Gln Ser Leu Thr Met Asp Pro Val Val Lys Ser Lys Glu Ile
        755                 760                 765
```

```
Glu Ala Lys Ile Lys Glu Leu Thr Ser Thr Cys Ser Pro Ile Ile Ser
        770                 775                 780

Lys Pro Lys Pro Lys Val Glu Pro Pro Lys Glu Gln Lys Asn Ala
785                 790                 795                 800

Glu Gln Asn Gly Pro Val Asp Gly Gln Gly Asp Asn Pro Gly Pro Gln
                805                 810                 815

Ala Ala Glu Gln Gly Thr Asp Thr Ala Val Pro Ser Asp Ser Asp Lys
        820                 825                 830

Lys Leu Pro Glu Met Asp Ile Asp
        835                 840

<210> SEQ ID NO 11
<211> LENGTH: 803
<212> TYPE: PRT
<213> ORGANISM: Homo sapiens

<400> SEQUENCE: 11

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
290                 295                 300
```

```
Glu Ser Asp Asp Glu Ala Ala Val Glu Glu Glu Glu Lys Lys
305                 310                 315                 320

Pro Lys Thr Lys Lys Val Glu Lys Thr Val Trp Asp Trp Glu Leu Met
            325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
            355                 360                 365

Pro Met Ala Tyr Ile His Phe Thr Ala Glu Gly Val Thr Phe Lys
370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
            405                 410                 415

Phe Ile Thr Asp Asp Phe His Asp Met Met Pro Lys Tyr Leu Asn Phe
            420                 425                 430

Val Lys Gly Val Val Asp Ser Asp Leu Pro Leu Asn Val Ser Arg
            435                 440                 445

Glu Thr Leu Gln Gln His Lys Leu Leu Lys Val Ile Arg Lys Lys Leu
450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
            485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
            515                 520                 525

Glu Arg Met Lys Glu Lys Gln Asp Lys Ile Tyr Phe Met Ala Gly Ser
530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
            565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
            595                 600                 605

Glu Ala Val Glu Lys Glu Phe Glu Pro Leu Leu Asn Trp Met Lys Asp
610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
            645                 650                 655

Asn Met Glu Arg Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
            675                 680                 685

Pro Arg His Pro Leu Ile Arg Asp Met Leu Arg Arg Ile Lys Glu Asp
            690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
```

```
                    725                 730                 735
Asp Arg Ile Glu Arg Met Leu Arg Leu Ser Leu Asn Ile Asp Pro Asp
            740                 745                 750

Ala Lys Val Glu Glu Pro Glu Glu Pro Glu Glu Thr Ala Glu
            755                 760                 765

Asp Thr Thr Glu Asp Thr Gln Asp Glu Asp Glu Glu Met Asp Val
            770                 775                 780

Gly Thr Asp Glu Glu Glu Thr Ala Lys Glu Ser Thr Ala Glu Lys
785                 790                 795                 800

Asp Glu Leu

<210> SEQ ID NO 12
<211> LENGTH: 530
<212> TYPE: PRT
<213> ORGANISM: Homo sapiens

<400> SEQUENCE: 12

Met Ala Ala Ile Lys Ala Val Asn Ser Lys Ala Glu Val Ala Arg Ala
1               5                   10                  15

Arg Ala Ala Leu Ala Val Asn Ile Cys Ala Ala Arg Gly Leu Gln Asp
                20                  25                  30

Val Leu Arg Thr Asn Leu Gly Pro Lys Gly Thr Met Lys Met Leu Val
            35                  40                  45

Ser Gly Ala Gly Asp Ile Lys Leu Thr Lys Asp Gly Asn Val Leu Leu
    50                  55                  60

Asp Glu Met Gln Ile Gln His Pro Thr Ala Ser Leu Ile Ala Lys Val
65                  70                  75                  80

Ala Thr Ala Gln Asp Asp Val Thr Gly Asp Gly Thr Thr Ser Asn Val
                85                  90                  95

Leu Ile Ile Gly Glu Leu Leu Lys Gln Ala Asp Leu Tyr Ile Ser Glu
            100                 105                 110

Gly Leu His Pro Arg Ile Ile Ala Glu Gly Phe Glu Ala Ala Lys Ile
        115                 120                 125

Lys Ala Leu Glu Val Leu Glu Glu Val Lys Val Thr Lys Glu Met Lys
    130                 135                 140

Arg Lys Ile Leu Leu Asp Val Ala Arg Thr Ser Leu Gln Thr Lys Val
145                 150                 155                 160

His Ala Glu Leu Ala Asp Val Leu Thr Glu Val Val Asp Ser Val
                165                 170                 175

Leu Ala Val Arg Arg Pro Gly Tyr Pro Ile Asp Leu Phe Met Val Glu
            180                 185                 190

Ile Met Glu Met Lys His Lys Leu Gly Thr Asp Thr Lys Leu Ile Gln
        195                 200                 205

Gly Leu Val Leu Asp His Gly Ala Arg His Pro Asp Met Lys Lys Arg
    210                 215                 220

Val Glu Asp Ala Phe Ile Leu Ile Cys Asn Val Ser Leu Glu Tyr Glu
225                 230                 235                 240

Lys Thr Glu Val Asn Ser Gly Phe Phe Tyr Lys Thr Ala Glu Glu Lys
                245                 250                 255

Glu Lys Leu Val Lys Ala Glu Arg Lys Phe Ile Glu Asp Arg Val Gln
            260                 265                 270

Lys Ile Ile Asp Leu Lys Asp Lys Val Cys Ala Gln Ser Asn Lys Gly
        275                 280                 285

Phe Val Val Ile Asn Gln Lys Gly Ile Asp Pro Phe Ser Leu Asp Ser
    290                 295                 300
```

```
Leu Ala Lys His Gly Ile Val Ala Leu Arg Arg Ala Lys Arg Arg Asn
305                 310                 315                 320

Met Glu Arg Leu Ser Leu Ala Cys Gly Gly Met Ala Val Asn Ser Phe
            325                 330                 335

Glu Asp Leu Thr Val Asp Cys Leu Gly His Ala Gly Leu Val Tyr Glu
        340                 345                 350

Tyr Thr Leu Gly Glu Glu Lys Phe Thr Phe Ile Glu Glu Cys Val Asn
    355                 360                 365

Pro Cys Ser Val Thr Leu Leu Val Lys Gly Pro Asn Lys His Thr Leu
370                 375                 380

Thr Gln Val Lys Asp Ala Ile Arg Asp Gly Leu Arg Ala Ile Lys Asn
385                 390                 395                 400

Ala Ile Glu Asp Gly Cys Met Val Pro Gly Ala Gly Ala Ile Glu Val
                405                 410                 415

Ala Met Ala Glu Ala Leu Val Thr Tyr Lys Asn Ser Ile Lys Gly Arg
            420                 425                 430

Ala Arg Leu Gly Val Gln Ala Phe Ala Asp Ala Leu Leu Ile Ile Pro
        435                 440                 445

Lys Val Leu Ala Gln Asn Ala Gly Tyr Asp Pro Gln Glu Thr Leu Val
    450                 455                 460

Lys Val Gln Ala Glu His Val Glu Ser Lys Gln Leu Val Gly Val Asp
465                 470                 475                 480

Leu Asn Thr Gly Glu Pro Met Val Ala Ala Asp Ala Gly Val Trp Asp
                485                 490                 495

Asn Tyr Cys Val Lys Lys Gln Leu Leu His Ser Cys Thr Val Ile Ala
            500                 505                 510

Thr Asn Ile Leu Leu Val Asp Glu Ile Met Arg Ala Gly Met Ser Ser
        515                 520                 525

Leu Lys
    530

<210> SEQ ID NO 13
<211> LENGTH: 556
<212> TYPE: PRT
<213> ORGANISM: Homo sapiens

<400> SEQUENCE: 13

Met Glu Gly Pro Leu Ser Val Phe Gly Asp Arg Ser Thr Gly Glu Thr
1               5                   10                  15

Ile Arg Ser Gln Asn Val Met Ala Ala Ser Ile Ala Asn Ile Val
            20                  25                  30

Lys Ser Ser Leu Gly Pro Val Gly Leu Asp Lys Met Leu Val Asp Asp
            35                  40                  45

Ile Gly Asp Val Thr Ile Thr Asn Asp Gly Ala Thr Ile Leu Lys Leu
    50                  55                  60

Leu Glu Val Glu His Pro Ala Ala Lys Val Leu Cys Glu Leu Ala Asp
65                  70                  75                  80

Leu Gln Asp Lys Glu Val Gly Asp Gly Thr Thr Ser Val Val Ile Ile
                85                  90                  95

Ala Ala Glu Leu Leu Lys Asn Ala Asp Glu Leu Val Lys Gln Lys Ile
            100                 105                 110

His Pro Thr Ser Val Ile Ser Gly Tyr Arg Leu Ala Cys Lys Glu Ala
        115                 120                 125

Val Arg Tyr Ile Asn Glu Asn Leu Ile Val Asn Thr Asp Glu Leu Gly
    130                 135                 140
```

-continued

```
Arg Asp Cys Leu Ile Asn Ala Ala Lys Thr Ser Met Ser Ser Lys Ile
145                 150                 155                 160

Ile Gly Ile Asn Gly Asp Phe Phe Ala Asn Met Val Val Asp Ala Val
                165                 170                 175

Leu Ala Ile Lys Tyr Thr Asp Ile Arg Gly Gln Pro Arg Tyr Pro Val
            180                 185                 190

Asn Ser Val Asn Ile Leu Lys Ala His Gly Arg Ser Gln Met Glu Ser
        195                 200                 205

Met Leu Ile Ser Gly Tyr Ala Leu Asn Cys Val Val Gly Ser Gln Gly
    210                 215                 220

Met Pro Lys Arg Ile Val Asn Ala Lys Ile Ala Cys Leu Asp Phe Ser
225                 230                 235                 240

Leu Gln Lys Thr Lys Met Lys Leu Gly Val Gln Val Val Ile Thr Asp
                245                 250                 255

Pro Glu Lys Leu Asp Gln Ile Arg Gln Arg Glu Ser Asp Ile Thr Lys
            260                 265                 270

Glu Arg Ile Gln Lys Ile Leu Ala Thr Gly Ala Asn Val Ile Leu Thr
        275                 280                 285

Thr Gly Gly Ile Asp Asp Met Cys Leu Lys Tyr Phe Val Glu Ala Gly
    290                 295                 300

Ala Met Ala Val Arg Arg Val Leu Lys Arg Asp Leu Lys Arg Ile Ala
305                 310                 315                 320

Lys Ala Ser Gly Ala Thr Ile Leu Ser Thr Leu Ala Asn Leu Glu Gly
                325                 330                 335

Glu Glu Thr Phe Glu Ala Ala Met Leu Gly Gln Ala Glu Glu Val Val
            340                 345                 350

Gln Glu Arg Ile Cys Asp Asp Glu Leu Ile Leu Ile Lys Asn Thr Lys
        355                 360                 365

Ala Arg Thr Ser Ala Ser Ile Ile Leu Arg Gly Ala Asn Asp Phe Met
    370                 375                 380

Cys Asp Glu Met Glu Arg Ser Leu His Asp Ala Leu Cys Val Val Lys
385                 390                 395                 400

Arg Val Leu Glu Ser Lys Ser Val Val Pro Gly Gly Gly Ala Val Glu
                405                 410                 415

Ala Ala Leu Ser Ile Tyr Leu Glu Asn Tyr Ala Thr Ser Met Gly Ser
            420                 425                 430

Arg Glu Gln Leu Ala Ile Ala Glu Phe Ala Arg Ser Leu Leu Val Ile
        435                 440                 445

Pro Asn Thr Leu Ala Val Asn Ala Ala Gln Asp Ser Thr Asp Leu Val
    450                 455                 460

Ala Lys Leu Arg Ala Phe His Asn Glu Ala Gln Val Asn Pro Glu Arg
465                 470                 475                 480

Lys Asn Leu Lys Trp Ile Gly Leu Asp Leu Ser Asn Gly Lys Pro Arg
                485                 490                 495

Asp Asn Lys Gln Ala Gly Val Phe Glu Pro Thr Ile Val Lys Val Lys
            500                 505                 510

Ser Leu Lys Phe Ala Thr Glu Ala Ala Ile Thr Ile Leu Arg Ile Asp
        515                 520                 525

Asp Leu Ile Lys Leu His Pro Glu Ser Lys Asp Lys His Gly Ser
    530                 535                 540

Tyr Glu Asp Ala Val His Ser Gly Ala Leu Asn Asp
545                 550                 555
```

<210> SEQ ID NO 14
<211> LENGTH: 509
<212> TYPE: PRT
<213> ORGANISM: Homo sapiens

<400> SEQUENCE: 14

Met Ala Ala Ile Gly Val His Leu Gly Cys Thr Ser Ala Cys Val Ala
1               5                   10                  15

Val Tyr Lys Asp Gly Arg Ala Gly Val Val Ala Asn Asp Ala Gly Asp
            20                  25                  30

Arg Val Thr Pro Ala Val Val Ala Tyr Ser Glu Asn Glu Glu Ile Val
        35                  40                  45

Gly Leu Ala Ala Lys Gln Ser Arg Ile Arg Asn Ile Ser Asn Thr Val
    50                  55                  60

Met Lys Val Lys Gln Ile Leu Gly Arg Ser Ser Ser Asp Pro Gln Ala
65                  70                  75                  80

Gln Lys Tyr Ile Ala Glu Ser Lys Cys Leu Val Ile Glu Lys Asn Gly
                85                  90                  95

Lys Leu Arg Tyr Glu Ile Asp Thr Gly Glu Glu Thr Lys Phe Val Asn
            100                 105                 110

Pro Glu Asp Val Ala Arg Leu Ile Phe Ser Lys Met Lys Glu Thr Ala
        115                 120                 125

His Ser Val Leu Gly Ser Asp Ala Asn Asp Val Val Ile Thr Val Pro
    130                 135                 140

Phe Asp Phe Gly Glu Lys Gln Lys Asn Ala Leu Gly Glu Ala Ala Arg
145                 150                 155                 160

Ala Ala Gly Phe Asn Val Leu Arg Leu Ile His Glu Pro Ser Ala Ala
                165                 170                 175

Leu Leu Ala Tyr Gly Ile Gly Gln Asp Ser Pro Thr Gly Lys Ser Asn
            180                 185                 190

Ile Leu Val Phe Lys Leu Gly Gly Thr Ser Leu Ser Leu Ser Val Met
        195                 200                 205

Glu Val Asn Ser Gly Ile Tyr Arg Val Leu Ser Thr Asn Thr Asp Asp
    210                 215                 220

Asn Ile Gly Gly Ala His Phe Thr Glu Thr Leu Ala Gln Tyr Leu Ala
225                 230                 235                 240

Ser Glu Phe Gln Arg Ser Phe Lys His Asp Val Arg Gly Asn Ala Arg
                245                 250                 255

Ala Met Met Lys Leu Thr Asn Ser Ala Glu Val Ala Lys His Ser Leu
            260                 265                 270

Ser Thr Leu Gly Ser Ala Asn Cys Phe Leu Asp Ser Leu Tyr Glu Gly
        275                 280                 285

Gln Asp Phe Asp Cys Asn Val Ser Arg Ala Arg Phe Glu Leu Leu Cys
    290                 295                 300

Ser Pro Leu Phe Asn Lys Cys Ile Glu Ala Ile Arg Gly Leu Leu Asp
305                 310                 315                 320

Gln Asn Gly Phe Thr Ala Asp Asp Ile Asn Lys Val Val Leu Cys Gly
                325                 330                 335

Gly Ser Ser Arg Ile Pro Lys Leu Gln Gln Leu Ile Lys Asp Leu Phe
            340                 345                 350

Pro Ala Val Glu Leu Leu Asn Ser Ile Pro Pro Asp Glu Val Ile Pro
        355                 360                 365

Ile Gly Ala Ala Ile Glu Ala Gly Ile Leu Ile Gly Lys Glu Asn Leu
    370                 375                 380

Leu Val Glu Asp Ser Leu Met Ile Glu Cys Ser Ala Arg Asp Ile Leu

```
                385                 390                 395                 400
Val Lys Gly Val Asp Glu Ser Gly Ala Ser Arg Phe Thr Val Leu Phe
                    405                 410                 415

Pro Ser Gly Thr Pro Leu Pro Ala Arg Arg Gln His Thr Leu Gln Ala
                420                 425                 430

Pro Gly Ser Ile Ser Ser Val Cys Leu Glu Leu Tyr Glu Ser Asp Gly
                435                 440                 445

Lys Asn Ser Ala Lys Glu Glu Thr Lys Phe Ala Gln Val Val Leu Gln
            450                 455                 460

Asp Leu Asp Lys Lys Glu Asn Gly Leu Arg Asp Ile Leu Ala Val Leu
465                 470                 475                 480

Thr Met Lys Arg Asp Gly Ser Leu His Val Thr Cys Thr Asp Gln Glu
                485                 490                 495

Thr Gly Lys Cys Glu Ala Ile Ser Ile Glu Ile Ala Ser
                500                 505

<210> SEQ ID NO 15
<211> LENGTH: 679
<212> TYPE: PRT
<213> ORGANISM: Homo sapiens

<400> SEQUENCE: 15

Met Ile Ser Ala Ser Arg Ala Ala Ala Arg Leu Val Gly Ala Ala
1               5                   10                  15

Ala Ser Arg Gly Pro Thr Ala Ala Arg His Gln Asp Ser Trp Asn Gly
                20                  25                  30

Leu Ser His Glu Ala Phe Arg Leu Val Ser Arg Arg Asp Tyr Ala Ser
            35                  40                  45

Glu Ala Ile Lys Gly Ala Val Val Gly Ile Asp Leu Gly Thr Thr Asn
    50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
                100                 105                 110

Pro Asn Asn Thr Phe Tyr Ala Thr Lys Arg Leu Ile Gly Arg Arg Tyr
            115                 120                 125

Asp Asp Pro Glu Val Gln Lys Asp Ile Lys Asn Val Pro Phe Lys Ile
130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255

Ile Gln Lys Gly Val Phe Glu Val Lys Ser Thr Asn Gly Asp Thr Phe
```

```
                  260                 265                 270
Leu Gly Gly Glu Asp Phe Asp Gln Ala Leu Leu Arg His Ile Val Lys
            275                 280                 285
Glu Phe Lys Arg Glu Thr Gly Val Asp Leu Thr Lys Asp Asn Met Ala
            290                 295                 300
Leu Gln Arg Val Arg Glu Ala Ala Glu Lys Ala Lys Cys Glu Leu Ser
305                 310                 315                 320
Ser Ser Val Gln Thr Asp Ile Asn Leu Pro Tyr Leu Thr Met Asp Ser
                325                 330                 335
Ser Gly Pro Lys His Leu Asn Met Lys Leu Thr Arg Ala Gln Phe Glu
            340                 345                 350
Gly Ile Val Thr Asp Leu Ile Arg Arg Thr Ile Ala Pro Cys Gln Lys
            355                 360                 365
Ala Met Gln Asp Ala Glu Val Ser Lys Ser Asp Ile Gly Glu Val Ile
            370                 375                 380
Leu Val Gly Gly Met Thr Arg Met Pro Lys Val Gln Gln Thr Val Gln
385                 390                 395                 400
Asp Leu Phe Gly Arg Ala Pro Ser Lys Ala Val Asn Pro Asp Glu Ala
                405                 410                 415
Val Ala Ile Gly Ala Ala Ile Gln Gly Gly Val Leu Ala Gly Asp Val
                420                 425                 430
Thr Asp Val Leu Leu Leu Asp Val Thr Pro Leu Ser Leu Gly Ile Glu
                435                 440                 445
Thr Leu Gly Gly Val Phe Thr Lys Leu Ile Asn Arg Asn Thr Thr Ile
450                 455                 460
Pro Thr Lys Lys Ser Gln Val Phe Ser Thr Ala Ala Asp Gly Gln Thr
465                 470                 475                 480
Gln Val Glu Ile Lys Val Cys Gln Gly Glu Arg Glu Met Ala Gly Asp
                485                 490                 495
Asn Lys Leu Leu Gly Gln Phe Thr Leu Ile Gly Ile Pro Pro Ala Pro
                500                 505                 510
Arg Gly Val Pro Gln Ile Glu Val Thr Phe Asp Ile Asp Ala Asn Gly
                515                 520                 525
Ile Val His Val Ser Ala Lys Asp Lys Gly Thr Gly Arg Glu Gln Gln
                530                 535                 540
Ile Val Ile Gln Ser Ser Gly Gly Leu Ser Lys Asp Asp Ile Glu Asn
545                 550                 555                 560
Met Val Lys Asn Ala Glu Lys Tyr Ala Glu Glu Asp Arg Arg Lys Lys
                565                 570                 575
Glu Arg Val Glu Ala Val Asn Met Ala Glu Gly Ile Ile His Asp Thr
                580                 585                 590
Glu Thr Lys Met Glu Glu Phe Lys Asp Gln Leu Pro Ala Asp Glu Cys
                595                 600                 605
Asn Lys Leu Lys Glu Glu Ile Ser Lys Met Arg Glu Leu Leu Ala Arg
                610                 615                 620
Lys Asp Ser Glu Thr Gly Glu Asn Ile Arg Gln Ala Ala Ser Ser Leu
625                 630                 635                 640
Gln Gln Ala Ser Leu Lys Leu Phe Glu Met Ala Tyr Lys Lys Met Ala
                645                 650                 655
Ser Glu Arg Glu Gly Ser Gly Ser Ser Gly Thr Gly Glu Gln Lys Glu
                660                 665                 670
Asp Gln Lys Glu Glu Lys Gln
                675
```

-continued

<210> SEQ ID NO 16
<211> LENGTH: 471
<212> TYPE: PRT
<213> ORGANISM: Homo sapiens

<400> SEQUENCE: 16

```
Met Ala Arg Glu Met Thr Ile Leu Gly Ser Ala Val Leu Thr Leu Leu
1               5                   10                  15

Leu Ala Gly Tyr Leu Ala Gln Gln Tyr Leu Pro Leu Pro Thr Pro Lys
            20                  25                  30

Val Ile Gly Ile Asp Leu Gly Thr Thr Tyr Cys Ser Val Gly Val Phe
        35                  40                  45

Phe Pro Gly Thr Gly Lys Val Lys Val Ile Pro Asp Glu Asn Gly His
    50                  55                  60

Ile Ser Ile Pro Ser Met Val Ser Phe Thr Asp Asn Asp Val Tyr Val
65                  70                  75                  80

Gly Tyr Glu Ser Val Glu Leu Ala Asp Ser Asn Pro Gln Asn Thr Ile
                85                  90                  95

Tyr Asp Ala Lys Arg Phe Ile Gly Lys Ile Phe Thr Ala Glu Glu Leu
            100                 105                 110

Glu Ala Glu Ile Gly Arg Tyr Pro Phe Lys Val Leu Asn Lys Asn Gly
        115                 120                 125

Met Val Glu Phe Ser Val Thr Ser Asn Glu Thr Ile Thr Val Ser Pro
    130                 135                 140

Glu Tyr Val Gly Ser Arg Leu Leu Leu Lys Leu Lys Glu Met Ala Glu
145                 150                 155                 160

Ala Tyr Leu Gly Met Pro Val Ala Asn Ala Val Ile Ser Val Pro Ala
                165                 170                 175

Glu Phe Asp Leu Lys Gln Arg Asn Ser Thr Ile Glu Ala Ala Asn Leu
            180                 185                 190

Ala Gly Leu Lys Ile Leu Arg Val Ile Asn Glu Pro Thr Ala Ala Ala
        195                 200                 205

Met Ala Tyr Gly Leu His Lys Ala Asp Val Phe His Val Leu Val Ile
    210                 215                 220

Asp Leu Gly Gly Gly Thr Leu Asp Val Ser Leu Leu Asn Lys Gln Gly
225                 230                 235                 240

Gly Met Phe Leu Thr Arg Ala Met Ser Gly Asn Asn Lys Leu Gly Gly
                245                 250                 255

Gln Asp Phe Asn Gln Arg Leu Leu Gln Tyr Leu Tyr Lys Gln Ile Tyr
            260                 265                 270

Gln Thr Tyr Gly Phe Val Pro Ser Arg Lys Glu Glu Ile His Arg Leu
        275                 280                 285

Arg Gln Ala Val Glu Met Val Lys Leu Asn Leu Thr Leu His Gln Ser
    290                 295                 300

Ala Gln Leu Ser Val Leu Leu Thr Val Glu Glu Gln Asp Arg Lys Glu
305                 310                 315                 320

Pro His Ser Ser Asp Thr Glu Leu Pro Lys Asp Lys Leu Ser Ser Ala
                325                 330                 335

Asp Asp His Arg Val Asn Ser Gly Phe Gly Arg Gly Leu Ser Asp Lys
            340                 345                 350

Lys Ser Gly Glu Ser Gln Val Leu Phe Glu Thr Glu Ile Ser Arg Lys
        355                 360                 365

Leu Phe Asp Thr Leu Asn Glu Asp Leu Phe Gln Lys Ile Leu Val Pro
    370                 375                 380
```

Ile Gln Gln Val Leu Lys Glu Gly His Leu Glu Lys Thr Glu Ile Asp
385                 390                 395                 400

Glu Val Val Leu Val Gly Gly Ser Thr Arg Ile Pro Arg Ile Arg Gln
            405                 410                 415

Val Ile Gln Glu Phe Phe Gly Lys Asp Pro Asn Thr Ser Val Asp Pro
        420                 425                 430

Asp Leu Ala Val Val Thr Gly Val Ala Ile Gln Ala Gly Ile Asp Gly
            435                 440                 445

Gly Ser Trp Pro Leu Gln Val Ser Ala Leu Glu Ile Pro Asn Lys His
    450                 455                 460

Leu Gln Lys Thr Asn Phe Asn
465                 470

<210> SEQ ID NO 17
<211> LENGTH: 999
<212> TYPE: PRT
<213> ORGANISM: Homo sapiens

<400> SEQUENCE: 17

Met Ala Asp Lys Val Arg Arg Gln Arg Pro Arg Arg Val Cys Trp
1               5                   10                  15

Ala Leu Val Ala Val Leu Leu Ala Asp Leu Ala Leu Ser Asp Thr
            20                  25                  30

Leu Ala Val Met Ser Val Asp Leu Gly Ser Glu Ser Met Lys Val Ala
            35                  40                  45

Ile Val Lys Pro Gly Val Pro Met Glu Ile Val Leu Asn Lys Glu Ser
        50                  55                  60

Arg Arg Lys Thr Pro Val Ile Val Thr Leu Lys Glu Asn Glu Arg Phe
65                  70                  75                  80

Phe Gly Asp Ser Ala Ala Ser Met Ala Ile Lys Asn Pro Lys Ala Thr
                85                  90                  95

Leu Arg Tyr Phe Gln His Leu Leu Gly Lys Gln Ala Asp Asn Pro His
            100                 105                 110

Val Ala Leu Tyr Gln Ala Arg Phe Pro Glu His Glu Leu Thr Phe Asp
        115                 120                 125

Pro Gln Arg Gln Thr Val His Phe Gln Ile Ser Ser Gln Leu Gln Phe
130                 135                 140

Ser Pro Glu Glu Val Leu Gly Met Val Leu Asn Tyr Ser Arg Ser Leu
145                 150                 155                 160

Ala Glu Asp Phe Ala Glu Gln Pro Ile Lys Asp Ala Val Ile Thr Val
                165                 170                 175

Pro Val Phe Phe Asn Gln Ala Glu Arg Arg Ala Val Leu Gln Ala Ala
            180                 185                 190

Arg Met Ala Gly Leu Lys Val Leu Gln Leu Ile Asn Asp Asn Thr Ala
        195                 200                 205

Thr Ala Leu Ser Tyr Gly Val Phe Arg Arg Lys Asp Ile Asn Thr Thr
    210                 215                 220

Ala Gln Asn Ile Met Phe Tyr Asp Met Gly Ser Gly Ser Thr Val Cys
225                 230                 235                 240

Thr Ile Val Thr Tyr Gln Met Val Lys Thr Lys Glu Ala Gly Met Gln
                245                 250                 255

Pro Gln Leu Gln Ile Arg Gly Val Gly Phe Asp Arg Thr Leu Gly Gly
            260                 265                 270

Leu Glu Met Glu Leu Arg Leu Arg Glu Arg Leu Ala Gly Leu Phe Asn
        275                 280                 285

-continued

```
Glu Gln Arg Lys Gly Gln Arg Ala Lys Asp Val Arg Glu Asn Pro Arg
    290                 295                 300
Ala Met Ala Lys Leu Leu Arg Glu Ala Asn Arg Leu Lys Thr Val Leu
305                 310                 315                 320
Ser Ala Asn Ala Asp His Met Ala Gln Ile Glu Gly Leu Met Asp Asp
                325                 330                 335
Val Asp Phe Lys Ala Lys Val Thr Arg Val Glu Phe Glu Glu Leu Cys
            340                 345                 350
Ala Asp Leu Phe Glu Arg Val Pro Gly Pro Val Gln Gln Ala Leu Gln
        355                 360                 365
Ser Ala Glu Met Ser Leu Asp Glu Ile Glu Gln Val Ile Leu Val Gly
    370                 375                 380
Gly Ala Thr Arg Val Pro Arg Val Gln Glu Val Leu Leu Lys Ala Val
385                 390                 395                 400
Gly Lys Glu Glu Leu Gly Lys Asn Ile Asn Ala Asp Glu Ala Ala Ala
                405                 410                 415
Met Gly Ala Val Tyr Gln Ala Ala Leu Ser Lys Ala Phe Lys Val
            420                 425                 430
Lys Pro Phe Val Val Arg Asp Ala Val Val Tyr Pro Ile Leu Val Glu
        435                 440                 445
Phe Thr Arg Glu Val Glu Glu Pro Gly Ile His Ser Leu Lys His
    450                 455                 460
Asn Lys Arg Val Leu Phe Ser Arg Met Gly Pro Tyr Pro Gln Arg Lys
465                 470                 475                 480
Val Ile Thr Phe Asn Arg Tyr Ser His Asp Phe Asn Phe His Ile Asn
                485                 490                 495
Tyr Gly Asp Leu Gly Phe Leu Gly Pro Glu Asp Leu Arg Val Phe Gly
            500                 505                 510
Ser Gln Asn Leu Thr Thr Val Lys Leu Lys Gly Val Gly Asp Ser Phe
        515                 520                 525
Lys Lys Tyr Pro Asp Tyr Glu Ser Lys Gly Ile Lys Ala His Phe Asn
    530                 535                 540
Leu Asp Glu Ser Gly Val Leu Ser Leu Asp Arg Val Glu Ser Val Phe
545                 550                 555                 560
Glu Thr Leu Val Glu Asp Ser Ala Glu Glu Ser Thr Leu Thr Lys
                565                 570                 575
Leu Gly Asn Thr Ile Ser Ser Leu Phe Gly Gly Thr Thr Pro Asp
            580                 585                 590
Ala Lys Glu Asn Gly Thr Asp Thr Val Gln Glu Glu Glu Ser Pro
        595                 600                 605
Ala Glu Gly Ser Lys Asp Glu Pro Gly Glu Gln Val Glu Leu Lys Glu
    610                 615                 620
Glu Ala Glu Ala Pro Val Glu Asp Gly Ser Gln Pro Pro Pro Glu
625                 630                 635                 640
Pro Lys Gly Asp Ala Thr Pro Glu Gly Glu Lys Ala Thr Glu Lys Glu
                645                 650                 655
Asn Gly Asp Lys Ser Glu Ala Gln Lys Pro Ser Glu Lys Ala Glu Ala
            660                 665                 670
Gly Pro Glu Gly Val Ala Pro Ala Pro Glu Gly Glu Lys Lys Gln Lys
        675                 680                 685
Pro Ala Arg Lys Arg Arg Met Val Glu Glu Ile Gly Val Glu Leu Val
    690                 695                 700
Val Leu Asp Leu Pro Asp Leu Pro Glu Asp Lys Leu Ala Gln Ser Val
705                 710                 715                 720
```

```
Gln Lys Leu Gln Asp Leu Thr Leu Arg Asp Leu Glu Lys Gln Glu Arg
            725                 730                 735

Glu Lys Ala Ala Asn Ser Leu Glu Ala Phe Ile Phe Glu Thr Gln Asp
        740                 745                 750

Lys Leu Tyr Gln Pro Glu Tyr Gln Val Ser Thr Glu Val Gln Arg
    755                 760                 765

Glu Glu Ile Ser Gly Lys Leu Ser Ala Ala Ser Thr Trp Leu Glu Asp
770                 775                 780

Glu Gly Val Gly Ala Thr Thr Val Met Leu Lys Glu Lys Leu Ala Glu
785                 790                 795                 800

Leu Arg Lys Leu Cys Gln Gly Leu Phe Phe Arg Val Glu Glu Arg Lys
                805                 810                 815

Lys Trp Pro Glu Arg Leu Ser Ala Leu Asp Asn Leu Leu Asn His Ser
            820                 825                 830

Ser Met Phe Leu Lys Gly Ala Arg Leu Ile Pro Glu Met Asp Gln Ile
        835                 840                 845

Phe Thr Glu Val Glu Met Thr Thr Leu Glu Lys Val Ile Asn Glu Thr
    850                 855                 860

Trp Ala Trp Lys Asn Ala Thr Leu Ala Glu Gln Ala Lys Leu Pro Ala
865                 870                 875                 880

Thr Glu Lys Pro Val Leu Leu Ser Lys Asp Ile Glu Ala Lys Met Met
                885                 890                 895

Ala Leu Asp Arg Glu Val Gln Tyr Leu Leu Asn Lys Ala Lys Phe Thr
            900                 905                 910

Lys Pro Arg Pro Arg Pro Lys Asp Lys Asn Gly Thr Arg Ala Glu Pro
        915                 920                 925

Pro Leu Asn Ala Ser Ala Ser Asp Gln Gly Glu Lys Val Ile Pro Pro
    930                 935                 940

Ala Gly Gln Thr Glu Asp Ala Glu Pro Ile Ser Glu Pro Glu Lys Val
945                 950                 955                 960

Glu Thr Gly Ser Glu Pro Gly Asp Thr Glu Pro Leu Glu Leu Gly Gly
                965                 970                 975

Pro Gly Ala Glu Pro Glu Gln Lys Glu Gln Ser Thr Gly Gln Lys Arg
            980                 985                 990

Pro Leu Lys Asn Asp Glu Leu
        995

<210> SEQ ID NO 18
<211> LENGTH: 175
<212> TYPE: PRT
<213> ORGANISM: Homo sapiens

<400> SEQUENCE: 18

Met Asp Ile Ala Ile His His Pro Trp Ile Arg Arg Pro Phe Phe Pro
1               5                   10                  15

Phe His Ser Pro Ser Arg Leu Phe Asp Gln Phe Phe Gly Glu His Leu
            20                  25                  30

Leu Glu Ser Asp Leu Phe Pro Thr Ser Thr Ser Leu Ser Pro Phe Tyr
        35                  40                  45

Leu Arg Pro Pro Ser Phe Leu Arg Ala Pro Ser Trp Phe Asp Thr Gly
    50                  55                  60

Leu Ser Glu Met Arg Leu Glu Lys Asp Arg Phe Ser Val Asn Leu Asp
65                  70                  75                  80

Val Lys His Phe Ser Pro Glu Glu Leu Lys Val Lys Val Leu Gly Asp
                85                  90                  95
```

```
Val Ile Glu Val His Gly Lys His Glu Arg Gln Asp Glu His Gly
            100                 105                 110

Phe Ile Ser Arg Glu Phe His Arg Lys Tyr Arg Ile Pro Ala Asp Val
            115                 120                 125

Asp Pro Leu Thr Ile Thr Ser Ser Leu Ser Ser Asp Gly Val Leu Thr
        130                 135                 140

Val Asn Gly Pro Arg Lys Gln Val Ser Gly Pro Glu Arg Thr Ile Pro
145                 150                 155                 160

Ile Thr Arg Glu Glu Lys Pro Ala Val Thr Ala Ala Pro Lys Lys
                165                 170                 175

<210> SEQ ID NO 19
<211> LENGTH: 182
<212> TYPE: PRT
<213> ORGANISM: Homo sapiens

<400> SEQUENCE: 19

Met Ser Gly Arg Ser Val Pro His Ala His Pro Ala Thr Ala Glu Tyr
1               5                   10                  15

Glu Phe Ala Asn Pro Ser Arg Leu Gly Glu Gln Arg Phe Gly Glu Gly
            20                  25                  30

Leu Leu Pro Glu Glu Ile Leu Thr Pro Thr Leu Tyr His Gly Tyr Tyr
        35                  40                  45

Val Arg Pro Arg Ala Ala Pro Ala Gly Glu Gly Ser Arg Ala Gly Ala
50                  55                  60

Ser Glu Leu Arg Leu Ser Glu Gly Lys Phe Gln Ala Phe Leu Asp Val
65                  70                  75                  80

Ser His Phe Thr Pro Asp Glu Val Thr Val Arg Thr Val Asp Asn Leu
                85                  90                  95

Leu Glu Val Ser Ala Arg His Pro Gln Arg Leu Asp Arg His Gly Phe
            100                 105                 110

Val Ser Arg Glu Phe Cys Arg Thr Tyr Val Leu Pro Ala Asp Val Asp
        115                 120                 125

Pro Trp Arg Val Arg Ala Ala Leu Ser His Asp Gly Ile Leu Asn Leu
130                 135                 140

Glu Ala Pro Arg Gly Gly Arg His Leu Asp Thr Glu Val Asn Glu Val
145                 150                 155                 160

Tyr Ile Ser Leu Leu Pro Ala Pro Pro Asp Pro Glu Glu Glu Glu Glu
                165                 170                 175

Ala Ala Ile Val Glu Pro
            180

<210> SEQ ID NO 20
<211> LENGTH: 412
<212> TYPE: PRT
<213> ORGANISM: Homo sapiens

<400> SEQUENCE: 20

Met Ala Asn Val Ala Asp Thr Lys Leu Tyr Asp Ile Leu Gly Val Pro
1               5                   10                  15

Pro Gly Ala Ser Glu Asn Glu Leu Lys Lys Ala Tyr Arg Lys Leu Ala
            20                  25                  30

Lys Glu Tyr His Pro Asp Lys Asn Pro Asn Ala Gly Asp Lys Phe Lys
        35                  40                  45

Glu Ile Ser Phe Ala Tyr Glu Val Leu Ser Asn Pro Glu Lys Arg Glu
    50                  55                  60
```

```
Leu Tyr Asp Arg Tyr Gly Glu Gln Gly Leu Arg Glu Gly Ser Gly Gly
 65                  70                  75                  80

Gly Gly Gly Met Asp Asp Ile Phe Ser His Ile Phe Gly Gly Gly Leu
             85                  90                  95

Phe Gly Phe Met Gly Asn Gln Ser Arg Ser Arg Asn Gly Arg Arg Arg
            100                 105                 110

Gly Glu Asp Met Met His Pro Leu Lys Val Ser Leu Glu Asp Leu Tyr
            115                 120                 125

Asn Gly Lys Thr Thr Lys Leu Gln Leu Ser Lys Asn Val Leu Cys Ser
        130                 135                 140

Ala Cys Ser Gly Gln Gly Lys Ser Gly Ala Val Gln Lys Cys Ser
145                 150                 155                 160

Ala Cys Arg Gly Arg Gly Val Arg Ile Met Ile Arg Gln Leu Ala Pro
                165                 170                 175

Gly Met Val Gln Gln Met Gln Ser Val Cys Ser Asp Cys Asn Gly Glu
            180                 185                 190

Gly Glu Val Ile Asn Glu Lys Asp Arg Cys Lys Lys Cys Glu Gly Lys
            195                 200                 205

Lys Val Ile Lys Glu Val Lys Ile Leu Glu Val His Val Asp Lys Gly
        210                 215                 220

Met Lys His Gly Gln Arg Ile Thr Phe Thr Gly Glu Ala Asp Gln Ala
225                 230                 235                 240

Pro Gly Val Glu Pro Gly Asp Ile Val Leu Leu Leu Gln Glu Lys Glu
                245                 250                 255

His Glu Val Phe Gln Arg Asp Gly Asn Asp Leu His Met Thr Tyr Lys
            260                 265                 270

Ile Gly Leu Val Glu Ala Leu Cys Gly Phe Gln Phe Thr Phe Lys His
        275                 280                 285

Leu Asp Gly Arg Gln Ile Val Val Lys Tyr Pro Pro Gly Lys Val Ile
    290                 295                 300

Glu Pro Gly Cys Val Arg Val Val Arg Gly Glu Gly Met Pro Gln Tyr
305                 310                 315                 320

Arg Asn Pro Phe Glu Lys Gly Asp Leu Tyr Ile Lys Phe Asp Val Gln
                325                 330                 335

Phe Pro Glu Asn Asn Trp Ile Asn Pro Asp Lys Leu Ser Glu Leu Glu
            340                 345                 350

Asp Leu Leu Pro Ser Arg Pro Glu Val Pro Asn Ile Ile Gly Glu Thr
        355                 360                 365

Glu Glu Val Glu Leu Gln Glu Phe Asp Ser Thr Arg Gly Ser Gly Gly
    370                 375                 380

Gly Gln Arg Arg Glu Ala Tyr Asn Asp Ser Ser Asp Glu Glu Ser Ser
385                 390                 395                 400

Ser His His Gly Pro Gly Val Gln Cys Ala His Gln
                405                 410

<210> SEQ ID NO 21
<211> LENGTH: 340
<212> TYPE: PRT
<213> ORGANISM: Homo sapiens

<400> SEQUENCE: 21

Met Gly Lys Asp Tyr Tyr Gln Thr Leu Gly Leu Ala Arg Gly Ala Ser
 1               5                  10                  15

Asp Glu Glu Ile Lys Arg Ala Tyr Arg Arg Gln Ala Leu Arg Tyr His
                20                  25                  30
```

```
Pro Asp Lys Asn Lys Glu Pro Gly Ala Glu Glu Lys Phe Lys Glu Ile
        35                  40                  45

Ala Glu Ala Tyr Asp Val Leu Ser Asp Pro Arg Lys Arg Glu Ile Phe
 50                  55                  60

Asp Arg Tyr Gly Glu Gly Leu Lys Gly Ser Gly Pro Ser Gly Gly
 65                  70                  75                  80

Ser Gly Gly Gly Ala Asn Gly Thr Ser Phe Ser Tyr Thr Phe His Gly
                85                  90                  95

Asp Pro His Ala Met Phe Ala Glu Phe Gly Gly Arg Asn Pro Phe
                100                 105                 110

Asp Thr Phe Phe Gly Gln Arg Asn Gly Glu Glu Gly Met Asp Ile Asp
        115                 120                 125

Asp Pro Phe Ser Gly Phe Pro Met Gly Met Gly Gly Phe Thr Asn Val
 130                 135                 140

Asn Phe Gly Arg Ser Arg Ser Ala Gln Glu Pro Ala Arg Lys Lys Gln
 145                 150                 155                 160

Asp Pro Pro Val Thr His Asp Leu Arg Val Ser Leu Glu Glu Ile Tyr
                165                 170                 175

Ser Gly Cys Thr Lys Lys Met Lys Ile Ser His Lys Arg Leu Asn Pro
                180                 185                 190

Asp Gly Lys Ser Ile Arg Asn Glu Asp Lys Ile Leu Thr Ile Glu Val
                195                 200                 205

Lys Lys Gly Trp Lys Glu Gly Thr Lys Ile Thr Phe Pro Lys Glu Gly
 210                 215                 220

Asp Gln Thr Ser Asn Asn Ile Pro Ala Asp Ile Val Phe Val Leu Lys
 225                 230                 235                 240

Asp Lys Pro His Asn Ile Phe Lys Arg Asp Gly Ser Asp Val Ile Tyr
                245                 250                 255

Pro Ala Arg Ile Ser Leu Arg Glu Ala Leu Cys Gly Cys Thr Val Asn
                260                 265                 270

Val Pro Thr Leu Asp Gly Arg Thr Ile Pro Val Val Phe Lys Asp Val
                275                 280                 285

Ile Arg Pro Gly Met Arg Arg Lys Val Pro Gly Glu Gly Leu Pro Leu
 290                 295                 300

Pro Lys Thr Pro Glu Lys Arg Gly Asp Leu Ile Ile Glu Phe Glu Val
 305                 310                 315                 320

Ile Phe Pro Glu Arg Ile Pro Gln Thr Ser Arg Thr Val Leu Glu Gln
                325                 330                 335

Val Leu Pro Ile
        340

<210> SEQ ID NO 22
<211> LENGTH: 324
<212> TYPE: PRT
<213> ORGANISM: Homo sapiens

<400> SEQUENCE: 22

Met Ala Ser Tyr Tyr Glu Ile Leu Asp Val Pro Arg Ser Ala Ser Ala
1                5                  10                  15

Asp Asp Ile Lys Lys Ala Tyr Arg Arg Lys Ala Leu Gln Trp His Pro
                20                  25                  30

Asp Lys Asn Pro Asp Asn Lys Glu Phe Ala Glu Lys Lys Phe Lys Glu
        35                  40                  45

Val Ala Glu Ala Tyr Glu Val Leu Ser Asp Lys His Lys Arg Glu Ile
 50                  55                  60
```

Tyr Asp Arg Tyr Gly Arg Glu Gly Leu Thr Gly Thr Gly Thr Gly Pro
65                  70                  75                  80

Ser Arg Ala Glu Ala Gly Ser Gly Gly Pro Gly Phe Thr Phe Thr Phe
                85                  90                  95

Arg Ser Pro Glu Glu Val Phe Arg Glu Phe Phe Gly Ser Gly Asp Pro
            100                 105                 110

Phe Ala Glu Leu Phe Asp Asp Leu Gly Pro Phe Ser Glu Leu Gln Asn
        115                 120                 125

Arg Gly Ser Arg His Ser Gly Pro Phe Phe Thr Phe Ser Ser Ser Phe
    130                 135                 140

Pro Gly His Ser Asp Phe Ser Ser Ser Phe Ser Phe Ser Pro Gly
145                 150                 155                 160

Ala Gly Ala Phe Arg Ser Val Ser Thr Ser Thr Thr Phe Val Gln Gly
                165                 170                 175

Arg Arg Ile Thr Thr Arg Arg Ile Met Glu Asn Gly Gln Glu Arg Val
            180                 185                 190

Glu Val Glu Glu Asp Gly Gln Leu Lys Ser Val Thr Ile Asn Gly Val
        195                 200                 205

Pro Asp Asp Leu Ala Leu Gly Leu Glu Leu Ser Arg Arg Glu Gln Gln
210                 215                 220

Pro Ser Val Thr Ser Arg Ser Gly Gly Thr Gln Val Gln Gln Thr Pro
225                 230                 235                 240

Ala Ser Cys Pro Leu Asp Ser Asp Leu Ser Glu Asp Glu Asp Leu Gln
                245                 250                 255

Leu Ala Met Ala Tyr Ser Leu Ser Glu Met Glu Ala Ala Gly Lys Lys
            260                 265                 270

Pro Ala Gly Gly Arg Glu Ala Gln His Arg Arg Gln Gly Arg Pro Lys
        275                 280                 285

Ala Gln His Gln Asp Pro Gly Leu Gly Thr Gln Glu Gly Ala Arg
    290                 295                 300

Gly Glu Ala Thr Lys Arg Ser Pro Ser Pro Glu Lys Ala Ser Arg
305                 310                 315                 320

Cys Leu Ile Leu

<210> SEQ ID NO 23
<211> LENGTH: 145
<212> TYPE: PRT
<213> ORGANISM: Homo sapiens

<400> SEQUENCE: 23

Met Val Asp Tyr Tyr Glu Val Leu Asp Val Pro Arg Gln Ala Ser Ser
1               5                   10                  15

Glu Ala Ile Lys Lys Ala Tyr Arg Lys Leu Ala Leu Lys Trp His Pro
            20                  25                  30

Asp Lys Asn Pro Glu Asn Lys Glu Glu Ala Glu Arg Arg Phe Lys Gln
        35                  40                  45

Val Ala Glu Ala Tyr Glu Val Leu Ser Asp Ala Lys Lys Arg Asp Ile
    50                  55                  60

Tyr Asp Arg Tyr Gly Glu Ala Gly Ala Glu Gly Gly Cys Thr Gly Gly
65                  70                  75                  80

Arg Pro Phe Glu Asp Pro Phe Tyr Val Phe Ser Phe Arg Asp Pro
                85                  90                  95

Ala Asp Val Phe Arg Glu Phe Phe Gly Gly Gln Asp Pro Phe Ser Phe
            100                 105                 110

Asp Leu Leu Gly Asn Pro Leu Glu Asn Ile Leu Gly Gly Ser Glu Glu

-continued

```
                    115                 120                 125
Leu Leu Gly Lys Gln Lys Gln Ser Val Cys Thr Pro Phe Leu Cys Leu
    130                 135                 140
Gln
145

<210> SEQ ID NO 24
<211> LENGTH: 358
<212> TYPE: PRT
<213> ORGANISM: Homo sapiens

<400> SEQUENCE: 24

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Lys Gln Tyr Asp Thr Tyr Gly Glu Glu Gly Leu Lys Asp
                85                  90                  95

Gly His Gln Ser Ser His Gly Asp Ile Phe Ser His Phe Phe Gly Asp
            100                 105                 110

Phe Gly Phe Met Phe Gly Gly Thr Pro Arg Gln Gln Asp Arg Asn Ile
        115                 120                 125

Pro Arg Gly Ser Asp Ile Ile Val Asp Leu Glu Val Thr Leu Glu Glu
    130                 135                 140

Val Tyr Ala Gly Asn Phe Val Glu Val Val Arg Asn Lys Pro Val Ala
145                 150                 155                 160

Arg Gln Ala Pro Gly Lys Arg Lys Cys Asn Cys Arg Gln Glu Met Arg
                165                 170                 175

Thr Thr Gln Leu Gly Pro Gly Arg Phe Gln Met Thr Gln Glu Val Val
            180                 185                 190

Cys Asp Glu Cys Pro Asn Val Lys Leu Val Asn Glu Glu Arg Thr Leu
        195                 200                 205

Glu Val Glu Ile Glu Pro Gly Val Arg Asp Gly Met Glu Tyr Pro Phe
    210                 215                 220

Ile Gly Glu Gly Glu Pro His Val Asp Gly Glu Pro Gly Asp Leu Arg
225                 230                 235                 240

Phe Arg Ile Lys Val Val Lys His Pro Ile Phe Glu Arg Arg Gly Asp
                245                 250                 255

Asp Leu Tyr Thr Asn Val Thr Ile Ser Leu Val Glu Ser Leu Val Gly
            260                 265                 270

Phe Glu Met Asp Ile Thr His Leu Asp Gly His Lys Val His Ile Ser
        275                 280                 285

Arg Asp Lys Ile Thr Arg Pro Gly Ala Lys Leu Trp Lys Lys Gly Glu
    290                 295                 300

Gly Leu Pro Asn Phe Asp Asn Asn Ile Lys Gly Ser Leu Ile Ile
305                 310                 315                 320

Thr Phe Asp Val Asp Phe Pro Lys Glu Gln Leu Thr Glu Glu Ala Arg
                325                 330                 335

Glu Gly Ile Lys Gln Leu Leu Lys Gln Gly Ser Val Gln Lys Val Tyr
```

```
                    340                 345                 350
Asn Gly Leu Gln Gly Tyr
            355

<210> SEQ ID NO 25
<211> LENGTH: 559
<212> TYPE: PRT
<213> ORGANISM: Homo sapiens

<400> SEQUENCE: 25

Met Ala Thr Ala Leu Ser Glu Glu Leu Asp Asn Glu Asp Tyr Tyr
1               5                   10                  15

Ser Leu Leu Asn Val Arg Arg Glu Ala Ser Ser Glu Glu Leu Lys Ala
                20                  25                  30

Ala Tyr Arg Arg Leu Cys Met Leu Tyr His Pro Asp Lys His Arg Asp
            35                  40                  45

Pro Glu Leu Lys Ser Gln Ala Glu Arg Leu Phe Asn Leu Val His Gln
50                  55                  60

Ala Tyr Glu Val Leu Ser Asp Pro Gln Thr Arg Ala Ile Tyr Asp Ile
65                  70                  75                  80

Tyr Gly Lys Arg Gly Leu Glu Met Glu Gly Trp Glu Val Val Glu Arg
                85                  90                  95

Arg Arg Thr Pro Ala Glu Ile Arg Glu Glu Phe Glu Arg Leu Gln Arg
            100                 105                 110

Glu Arg Glu Glu Arg Arg Leu Gln Gln Arg Thr Asn Pro Lys Gly Thr
        115                 120                 125

Ile Ser Val Gly Val Asp Ala Thr Asp Leu Phe Asp Arg Tyr Asp Glu
130                 135                 140

Glu Tyr Glu Asp Val Ser Gly Ser Ser Phe Pro Gln Ile Glu Ile Asn
145                 150                 155                 160

Lys Met His Ile Ser Gln Ser Ile Glu Ala Pro Leu Thr Ala Thr Asp
                165                 170                 175

Thr Ala Ile Leu Ser Gly Ser Leu Ser Thr Gln Asn Gly Asn Gly Gly
            180                 185                 190

Gly Ser Ile Asn Phe Ala Leu Arg Arg Val Thr Ser Ala Lys Gly Trp
        195                 200                 205

Gly Glu Leu Glu Phe Gly Ala Gly Asp Leu Gln Gly Pro Leu Phe Gly
210                 215                 220

Leu Lys Leu Phe Arg Asn Leu Thr Pro Arg Cys Phe Val Thr Thr Asn
225                 230                 235                 240

Cys Ala Leu Gln Phe Ser Ser Arg Gly Ile Arg Pro Gly Leu Thr Thr
                245                 250                 255

Val Leu Ala Arg Asn Leu Asp Lys Asn Thr Met Gly Tyr Leu Gln Trp
            260                 265                 270

Arg Trp Gly Ile Gln Ser Ala Met Asn Thr Ser Ile Val Arg Asp Thr
        275                 280                 285

Lys Thr Ser His Phe Thr Val Ala Leu Gln Leu Gly Ile Pro His Ser
290                 295                 300

Phe Ala Leu Ile Ile Tyr Gln His Lys Phe Gln Asp Asp Gln Thr
305                 310                 315                 320

Arg Val Lys Gly Ser Leu Lys Ala Gly Phe Phe Gly Thr Val Val Glu
                325                 330                 335

Tyr Gly Ala Glu Arg Lys Ile Ser Arg His Ser Val Leu Gly Ala Ala
            340                 345                 350

Val Ser Val Gly Val Pro Gln Gly Val Ser Leu Lys Val Lys Leu Asn
```

```
                355                 360                 365
Arg Ala Ser Gln Thr Tyr Phe Phe Pro Ile His Leu Thr Asp Gln Leu
        370                 375                 380

Leu Pro Ser Ala Met Phe Tyr Ala Thr Val Gly Pro Leu Val Val Tyr
385                 390                 395                 400

Phe Ala Met His Arg Leu Ile Ile Lys Pro Tyr Leu Arg Ala Gln Lys
                405                 410                 415

Glu Lys Glu Leu Glu Lys Gln Arg Glu Ser Ala Ala Thr Asp Val Leu
                420                 425                 430

Gln Lys Lys Gln Glu Ala Glu Ser Ala Val Arg Leu Met Gln Glu Ser
        435                 440                 445

Val Arg Arg Ile Ile Glu Ala Glu Ser Arg Met Gly Leu Ile Ile
450                 455                 460

Val Asn Ala Trp Tyr Gly Lys Phe Val Asn Asp Lys Ser Arg Lys Ser
465                 470                 475                 480

Glu Lys Val Lys Val Ile Asp Val Thr Val Pro Leu Gln Cys Leu Val
                485                 490                 495

Lys Asp Ser Lys Leu Ile Leu Thr Glu Ala Ser Lys Ala Gly Leu Pro
                500                 505                 510

Gly Phe Tyr Asp Pro Cys Val Gly Glu Glu Lys Asn Leu Lys Val Leu
        515                 520                 525

Tyr Gln Phe Arg Gly Val Leu His Gln Val Met Val Leu Asp Ser Glu
530                 535                 540

Ala Leu Arg Ile Pro Lys Gln Ser His Arg Ile Asp Thr Asp Gly
545                 550                 555

<210> SEQ ID NO 26
<211> LENGTH: 484
<212> TYPE: PRT
<213> ORGANISM: Homo sapiens

<400> SEQUENCE: 26

Met Ala Ala Thr Glu Pro Glu Leu Leu Asp Asp Gln Glu Ala Lys Arg
1               5                   10                  15

Glu Ala Glu Thr Phe Lys Glu Gln Gly Asn Ala Tyr Tyr Ala Lys Lys
                20                  25                  30

Asp Tyr Asn Glu Ala Tyr Asn Tyr Tyr Thr Lys Ala Ile Asp Met Cys
            35                  40                  45

Pro Lys Asn Ala Ser Tyr Tyr Gly Asn Arg Ala Ala Thr Leu Met Met
        50                  55                  60

Leu Gly Arg Phe Arg Glu Ala Leu Gly Asp Ala Gln Gln Ser Val Arg
65              70                  75                  80

Leu Asp Asp Ser Phe Val Arg Gly His Leu Arg Glu Gly Lys Cys His
                85                  90                  95

Leu Ser Leu Gly Asn Ala Met Ala Ala Cys Arg Ser Phe Gln Arg Ala
                100                 105                 110

Leu Glu Leu Asp His Lys Asn Ala Gln Ala Gln Gln Glu Phe Lys Asn
            115                 120                 125

Ala Asn Ala Val Met Glu Tyr Glu Lys Ile Ala Glu Thr Asp Phe Glu
        130                 135                 140

Lys Arg Asp Phe Arg Lys Val Val Phe Cys Met Asp Arg Ala Leu Glu
145                 150                 155                 160

Phe Ala Pro Ala Cys His Arg Phe Lys Ile Leu Lys Ala Glu Cys Leu
                165                 170                 175

Ala Met Leu Gly Arg Tyr Pro Glu Ala Gln Ser Val Ala Ser Asp Ile
```

```
                    180                 185                 190
Leu Arg Met Asp Ser Thr Asn Ala Asp Ala Leu Tyr Val Arg Gly Leu
            195                 200                 205

Cys Leu Tyr Tyr Glu Asp Cys Ile Glu Lys Ala Val Gln Phe Phe Val
        210                 215                 220

Gln Ala Leu Arg Met Ala Pro Asp His Glu Lys Ala Cys Ile Ala Cys
225                 230                 235                 240

Arg Asn Ala Lys Ala Leu Lys Ala Lys Lys Glu Asp Gly Asn Lys Ala
                245                 250                 255

Phe Lys Glu Gly Asn Tyr Lys Leu Ala Tyr Glu Leu Tyr Thr Glu Ala
            260                 265                 270

Leu Gly Ile Asp Pro Asn Asn Ile Lys Thr Asn Ala Lys Leu Tyr Cys
        275                 280                 285

Asn Arg Gly Thr Val Asn Ser Lys Leu Arg Lys Leu Asp Asp Ala Ile
        290                 295                 300

Glu Asp Cys Thr Asn Ala Val Lys Leu Asp Asp Thr Tyr Ile Lys Ala
305                 310                 315                 320

Tyr Leu Arg Arg Ala Gln Cys Tyr Met Asp Thr Glu Gln Tyr Glu Glu
                325                 330                 335

Ala Val Arg Asp Tyr Glu Lys Val Tyr Gln Thr Glu Lys Thr Lys Glu
            340                 345                 350

His Lys Gln Leu Leu Lys Asn Ala Gln Leu Glu Leu Lys Lys Ser Lys
        355                 360                 365

Arg Lys Asp Tyr Tyr Lys Ile Leu Gly Val Asp Lys Asn Ala Ser Glu
        370                 375                 380

Asp Glu Ile Lys Lys Ala Tyr Arg Lys Arg Ala Leu Met His His Pro
385                 390                 395                 400

Asp Arg His Ser Gly Ala Ser Ala Glu Val Gln Lys Glu Glu Glu Lys
                405                 410                 415

Lys Phe Lys Glu Val Gly Glu Ala Phe Thr Ile Leu Ser Asp Pro Lys
            420                 425                 430

Lys Lys Thr Arg Tyr Asp Ser Gly Gln Asp Leu Asp Glu Glu Gly Met
        435                 440                 445

Asn Met Gly Asp Phe Asp Pro Asn Asn Ile Phe Lys Ala Phe Phe Gly
        450                 455                 460

Gly Pro Gly Gly Phe Ser Phe Glu Ala Ser Gly Pro Gly Asn Phe Phe
465                 470                 475                 480

Phe Gln Phe Gly

<210> SEQ ID NO 27
<211> LENGTH: 913
<212> TYPE: PRT
<213> ORGANISM: Homo sapiens

<400> SEQUENCE: 27

Met Lys Asp Ser Glu Asn Lys Gly Ala Ser Ser Pro Asp Met Glu Pro
1               5                   10                  15

Ser Tyr Gly Gly Gly Leu Phe Asp Met Val Lys Gly Gly Ala Gly Arg
            20                  25                  30

Leu Phe Ser Asn Leu Lys Asp Asn Leu Lys Asp Thr Leu Lys Asp Thr
        35                  40                  45

Ser Ser Arg Val Ile Gln Ser Val Thr Ser Tyr Thr Lys Gly Asp Leu
    50                  55                  60

Asp Phe Thr Tyr Val Thr Ser Arg Ile Ile Val Met Ser Phe Pro Leu
65                  70                  75                  80
```

-continued

```
Asp Asn Val Asp Ile Gly Phe Arg Asn Gln Val Asp Asp Ile Arg Ser
                85                  90                  95
Phe Leu Asp Ser Arg His Leu Asp His Tyr Thr Val Tyr Asn Leu Ser
                100                 105                 110
Pro Lys Ser Tyr Arg Thr Ala Lys Phe His Ser Arg Val Ser Glu Cys
                115                 120                 125
Ser Trp Pro Ile Arg Gln Ala Pro Ser Leu His Asn Leu Phe Ala Val
        130                 135                 140
Cys Arg Asn Met Tyr Asn Trp Leu Leu Gln Asn Pro Lys Asn Val Cys
145                 150                 155                 160
Val Val His Cys Leu Asp Gly Arg Ala Ala Ser Ile Leu Val Gly
                165                 170                 175
Ala Met Phe Ile Phe Cys Asn Leu Tyr Ser Thr Pro Gly Pro Ala Ile
                180                 185                 190
Arg Leu Leu Tyr Ala Lys Arg Pro Gly Ile Gly Leu Ser Pro Ser His
                195                 200                 205
Arg Arg Tyr Leu Gly Tyr Met Cys Asp Leu Leu Ala Asp Lys Pro Tyr
        210                 215                 220
Arg Pro His Phe Lys Pro Leu Thr Ile Lys Ser Ile Thr Val Ser Pro
225                 230                 235                 240
Ile Pro Phe Phe Asn Lys Gln Arg Asn Gly Cys Arg Pro Tyr Cys Asp
                245                 250                 255
Val Leu Ile Gly Glu Thr Lys Ile Tyr Ser Thr Cys Thr Asp Phe Glu
                260                 265                 270
Arg Met Lys Glu Tyr Arg Val Gln Asp Gly Lys Ile Phe Ile Pro Leu
                275                 280                 285
Asn Ile Thr Val Gln Gly Asp Val Val Val Ser Met Tyr His Leu Arg
                290                 295                 300
Ser Thr Ile Gly Ser Arg Leu Gln Ala Lys Val Thr Asn Thr Gln Ile
305                 310                 315                 320
Phe Gln Leu Gln Phe His Thr Gly Phe Ile Pro Leu Asp Thr Thr Val
                325                 330                 335
Leu Lys Phe Thr Lys Pro Glu Leu Asp Ala Cys Asp Val Pro Glu Lys
                340                 345                 350
Tyr Pro Gln Leu Phe Gln Val Thr Leu Asp Val Glu Leu Gln Pro His
                355                 360                 365
Asp Lys Val Ile Asp Leu Thr Pro Pro Trp Glu His Tyr Cys Thr Lys
                370                 375                 380
Asp Val Asn Pro Ser Ile Leu Phe Ser Ser His Gln Glu His Gln Asp
385                 390                 395                 400
Thr Leu Ala Leu Gly Gly Gln Ala Pro Ile Asp Ile Pro Pro Asp Asn
                405                 410                 415
Pro Arg His Tyr Gly Gln Ser Gly Phe Phe Ala Ser Leu Cys Trp Gln
                420                 425                 430
Asp Gln Lys Ser Glu Lys Ser Phe Cys Glu Glu Asp His Ala Ala Leu
                435                 440                 445
Val Asn Gln Glu Ser Glu Gln Ser Asp Asp Glu Leu Leu Thr Leu Ser
                450                 455                 460
Ser Pro His Gly Asn Ala Asn Gly Asp Lys Pro His Gly Val Lys Lys
465                 470                 475                 480
Pro Ser Lys Lys Gln Gln Glu Pro Ala Ala Pro Pro Pro Glu Asp
                485                 490                 495
Val Asp Leu Leu Gly Leu Glu Gly Ser Ala Met Ser Asn Ser Phe Ser
```

-continued

```
                500             505             510
Pro Pro Ala Ala Pro Pro Thr Asn Ser Glu Leu Leu Ser Asp Leu Phe
            515                 520                 525
Gly Gly Gly Gly Ala Ala Gly Pro Thr Gln Ala Gly Gln Ser Gly Val
            530                 535                 540
Glu Asp Val Phe His Pro Ser Gly Pro Ala Ser Thr Gln Ser Thr Pro
545                 550                 555                 560
Arg Arg Ser Ala Thr Ser Thr Ser Ala Ser Pro Thr Leu Arg Val Gly
                565                 570                 575
Glu Gly Ala Thr Phe Asp Pro Phe Gly Ala Pro Ser Lys Pro Ser Gly
                580                 585                 590
Gln Asp Leu Leu Gly Ser Phe Leu Asn Thr Ser Ser Ala Ser Ser Asp
                595                 600                 605
Pro Phe Leu Gln Pro Thr Arg Ser Pro Ser Pro Thr Val His Ala Ser
            610                 615                 620
Ser Thr Pro Ala Val Asn Ile Gln Pro Asp Val Ser Gly Gly Trp Asp
625                 630                 635                 640
Trp His Ala Lys Pro Gly Gly Phe Gly Met Gly Ser Lys Ser Ala Ala
                645                 650                 655
Thr Ser Pro Thr Gly Ser Ser His Gly Thr Pro Thr His Gln Ser Lys
                660                 665                 670
Pro Gln Thr Leu Asp Pro Phe Ala Asp Leu Gly Thr Leu Gly Ser Ser
            675                 680                 685
Ser Phe Ala Ser Lys Pro Thr Thr Pro Thr Gly Leu Gly Gly Gly Phe
            690                 695                 700
Pro Pro Leu Ser Ser Pro Gln Lys Ala Ser Pro Gln Pro Met Gly Gly
705                 710                 715                 720
Gly Trp Gln Gln Gly Gly Ala Tyr Asn Trp Gln Pro Gln Pro Pro Lys
                725                 730                 735
Pro Gln Pro Ser Met Pro His Ser Ser Pro Gln Asn Arg Pro Asn Tyr
                740                 745                 750
Asn Val Ser Phe Ser Ala Met Pro Gly Gly Gln Asn Glu Arg Gly Lys
                755                 760                 765
Gly Ser Ser Asn Leu Glu Gly Lys Gln Lys Ala Ala Asp Phe Glu Asp
            770                 775                 780
Leu Leu Ser Gly Gln Gly Phe Asn Ala His Lys Asp Lys Lys Gly Pro
785                 790                 795                 800
Arg Thr Ile Ala Glu Met Arg Lys Glu Met Ala Lys Glu Met Asp
                805                 810                 815
Pro Glu Lys Leu Lys Ile Leu Glu Trp Ile Glu Gly Lys Glu Arg Asn
            820                 825                 830
Ile Arg Ala Leu Leu Ser Thr Met His Thr Val Leu Trp Ala Gly Glu
            835                 840                 845
Thr Lys Trp Lys Pro Val Gly Met Ala Asp Leu Val Thr Pro Glu Gln
            850                 855                 860
Val Lys Lys Val Tyr Arg Lys Ala Val Leu Val His Pro Asp Lys
865                 870                 875                 880
Ala Thr Gly Gln Pro Tyr Glu Gln Tyr Ala Lys Met Ile Phe Met Glu
                885                 890                 895
Leu Asn Asp Ala Trp Ser Glu Phe Glu Asn Gln Gly Gln Lys Pro Leu
            900                 905                 910
Tyr
```

```
<210> SEQ ID NO 28
<211> LENGTH: 31
<212> TYPE: DNA
<213> ORGANISM: Artificial
<220> FEATURE:
<223> OTHER INFORMATION: primer sequence

<400> SEQUENCE: 28
ttggatccat ggccaaagcc gcggcgatcg g                                  31

<210> SEQ ID NO 29
<211> LENGTH: 33
<212> TYPE: DNA
<213> ORGANISM: Artificial
<220> FEATURE:
<223> OTHER INFORMATION: primer sequence

<400> SEQUENCE: 29
ttctcgagct aatctacctc ctcaatggtg ggg                                33

<210> SEQ ID NO 30
<211> LENGTH: 30
<212> TYPE: DNA
<213> ORGANISM: Artificial
<220> FEATURE:
<223> OTHER INFORMATION: primer sequence

<400> SEQUENCE: 30
ttagatctat gtcggtggtg gggttggacg                                    30

<210> SEQ ID NO 31
<211> LENGTH: 31
<212> TYPE: DNA
<213> ORGANISM: Artificial
<220> FEATURE:
<223> OTHER INFORMATION: primer sequence

<400> SEQUENCE: 31
ttctcgagct agtccaagtc catattaaca g                                  31

<210> SEQ ID NO 32
<211> LENGTH: 30
<212> TYPE: DNA
<213> ORGANISM: Artificial
<220> FEATURE:
<223> OTHER INFORMATION: primer sequence

<400> SEQUENCE: 32
ttggatccat gcctgaggaa acccagaccc                                    30

<210> SEQ ID NO 33
<211> LENGTH: 34
<212> TYPE: DNA
<213> ORGANISM: Artificial
<220> FEATURE:
<223> OTHER INFORMATION: primer sequence

<400> SEQUENCE: 33
ttctcgagtt agtctacttc ttccatgcgt gatg                               34

<210> SEQ ID NO 34
<211> LENGTH: 33
<212> TYPE: DNA
<213> ORGANISM: Artificial
<220> FEATURE:
<223> OTHER INFORMATION: primer sequence

<400> SEQUENCE: 34
```
ttggatccat gcttcggtta cccacagtct ttc                33

<210> SEQ ID NO 35
<211> LENGTH: 32
<212> TYPE: DNA
<213> ORGANISM: Artificial
<220> FEATURE:
<223> OTHER INFORMATION: primer sequence

<400> SEQUENCE: 35
ttctcgagtt agaacatgcc acctcccata cc                 32

<210> SEQ ID NO 36
<211> LENGTH: 36
<212> TYPE: DNA
<213> ORGANISM: Artificial
<220> FEATURE:
<223> OTHER INFORMATION: primer sequence

<400> SEQUENCE: 36
ttggatccat ggtgaaagaa acaacttact acgatg             36

<210> SEQ ID NO 37
<211> LENGTH: 34
<212> TYPE: DNA
<213> ORGANISM: Artificial
<220> FEATURE:
<223> OTHER INFORMATION: primer sequence

<400> SEQUENCE: 37
ttctcgagtt aagaggtctg acactgaaca ccac               34

<210> SEQ ID NO 38
<211> LENGTH: 29
<212> TYPE: DNA
<213> ORGANISM: Artificial
<220> FEATURE:
<223> OTHER INFORMATION: primer sequence

<400> SEQUENCE: 38
ttggatccat gaccgagcgc cgcgtcccc                     29

<210> SEQ ID NO 39
<211> LENGTH: 31
<212> TYPE: DNA
<213> ORGANISM: Artificial
<220> FEATURE:
<223> OTHER INFORMATION: primer sequence

<400> SEQUENCE: 39
ttctcgagtt acttggcggc agtctcatcg g                  31

<210> SEQ ID NO 40
<211> LENGTH: 32
<212> TYPE: DNA
<213> ORGANISM: Artificial
<220> FEATURE:
<223> OTHER INFORMATION: primer sequence

<400> SEQUENCE: 40
ttggatccat ggcaggacaa gcgtttagaa ag                 32

<210> SEQ ID NO 41
<211> LENGTH: 33
<212> TYPE: DNA
<213> ORGANISM: Artificial

```
<220> FEATURE:
<223> OTHER INFORMATION: primer sequence

<400> SEQUENCE: 41
ttctcgagtc agtctacgta ctttccaaga atg                            33

<210> SEQ ID NO 42
<211> LENGTH: 28
<212> TYPE: DNA
<213> ORGANISM: Artificial
<220> FEATURE:
<223> OTHER INFORMATION: primer sequence

<400> SEQUENCE: 42
aagatatcca tgtcggtggt gggcatag                                  28

<210> SEQ ID NO 43
<211> LENGTH: 34
<212> TYPE: DNA
<213> ORGANISM: Artificial
<220> FEATURE:
<223> OTHER INFORMATION: primer sequence

<400> SEQUENCE: 43
aagcggccgc tcaatcaatg tccatttcag gaag                           34

<210> SEQ ID NO 44
<211> LENGTH: 30
<212> TYPE: DNA
<213> ORGANISM: Artificial
<220> FEATURE:
<223> OTHER INFORMATION: primer sequence

<400> SEQUENCE: 44
aaggatccat gagggccctg tgggtgctgg                                30

<210> SEQ ID NO 45
<211> LENGTH: 37
<212> TYPE: DNA
<213> ORGANISM: Artificial
<220> FEATURE:
<223> OTHER INFORMATION: primer sequence

<400> SEQUENCE: 45
ttctcgagtt acaattcatc tttttcagct gtagatt                        37

<210> SEQ ID NO 46
<211> LENGTH: 32
<212> TYPE: DNA
<213> ORGANISM: Artificial
<220> FEATURE:
<223> OTHER INFORMATION: primer sequence

<400> SEQUENCE: 46
aaggatccat ggctgcgata aaggccgtca ac                             32

<210> SEQ ID NO 47
<211> LENGTH: 34
<212> TYPE: DNA
<213> ORGANISM: Artificial
<220> FEATURE:
<223> OTHER INFORMATION: primer sequence

<400> SEQUENCE: 47
ttctcgagtc atttgagaga agacatccca gctc                           34
```

<210> SEQ ID NO 48
<211> LENGTH: 32
<212> TYPE: DNA
<213> ORGANISM: Artificial
<220> FEATURE:
<223> OTHER INFORMATION: primer sequence

<400> SEQUENCE: 48
aatgatcaat ggagggcct ttgtccgtgt tc                            32

<210> SEQ ID NO 49
<211> LENGTH: 35
<212> TYPE: DNA
<213> ORGANISM: Artificial
<220> FEATURE:
<223> OTHER INFORMATION: primer sequence

<400> SEQUENCE: 49
ttgcggccgc tcaatcatta agggctccag agtga                        35

<210> SEQ ID NO 50
<211> LENGTH: 30
<212> TYPE: DNA
<213> ORGANISM: Artificial
<220> FEATURE:
<223> OTHER INFORMATION: primer sequence

<400> SEQUENCE: 50
aaggatccat ggcggccatc ggagttcacc                              30

<210> SEQ ID NO 51
<211> LENGTH: 35
<212> TYPE: DNA
<213> ORGANISM: Artificial
<220> FEATURE:
<223> OTHER INFORMATION: primer sequence

<400> SEQUENCE: 51
ttctcgagct aagatgctat ctcaatagag attgc                        35

<210> SEQ ID NO 52
<211> LENGTH: 32
<212> TYPE: DNA
<213> ORGANISM: Artificial
<220> FEATURE:
<223> OTHER INFORMATION: primer sequence

<400> SEQUENCE: 52
aaggatccat gataagtgcc agccgagctg ca                           32

<210> SEQ ID NO 53
<211> LENGTH: 35
<212> TYPE: DNA
<213> ORGANISM: Artificial
<220> FEATURE:
<223> OTHER INFORMATION: primer sequence

<400> SEQUENCE: 53
ttctcgagtt actgtttttc ctccttttga tcttc                        35

<210> SEQ ID NO 54
<211> LENGTH: 33
<212> TYPE: DNA
<213> ORGANISM: Artificial
<220> FEATURE:
<223> OTHER INFORMATION: primer sequence

<400> SEQUENCE: 54
aagaattcat ggccagagag atgacgatct tag     33

<210> SEQ ID NO 55
<211> LENGTH: 35
<212> TYPE: DNA
<213> ORGANISM: Artificial
<220> FEATURE:
<223> OTHER INFORMATION: primer sequence

<400> SEQUENCE: 55
ttctcgagtc agttgaagtt ggttttttgt aaatg     35

<210> SEQ ID NO 56
<211> LENGTH: 32
<212> TYPE: DNA
<213> ORGANISM: Artificial
<220> FEATURE:
<223> OTHER INFORMATION: primer sequence

<400> SEQUENCE: 56
aagaattcat ggcagacaaa gttaggaggc ag     32

<210> SEQ ID NO 57
<211> LENGTH: 34
<212> TYPE: DNA
<213> ORGANISM: Artificial
<220> FEATURE:
<223> OTHER INFORMATION: primer sequence

<400> SEQUENCE: 57
ttctcgagtt atagttcgtc gttcttcaaa ggcc     34

<210> SEQ ID NO 58
<211> LENGTH: 31
<212> TYPE: DNA
<213> ORGANISM: Artificial
<220> FEATURE:
<223> OTHER INFORMATION: primer sequence

<400> SEQUENCE: 58
aagaattcat ggacatcgcc atccaccacc c     31

<210> SEQ ID NO 59
<211> LENGTH: 32
<212> TYPE: DNA
<213> ORGANISM: Artificial
<220> FEATURE:
<223> OTHER INFORMATION: primer sequence

<400> SEQUENCE: 59
ttctcgagct atttcttggg ggctgcggtg ac     32

<210> SEQ ID NO 60
<211> LENGTH: 32
<212> TYPE: DNA
<213> ORGANISM: Artificial
<220> FEATURE:
<223> OTHER INFORMATION: primer sequence

<400> SEQUENCE: 60
aaggatccat gtcgggccgc tcagtgccac at     32

<210> SEQ ID NO 61
<211> LENGTH: 32
<212> TYPE: DNA
<213> ORGANISM: Artificial

```
<220> FEATURE:
<223> OTHER INFORMATION: primer sequence

<400> SEQUENCE: 61
ttctcgagtc agggctcaac tatggctgcc tc                                32

<210> SEQ ID NO 62
<211> LENGTH: 32
<212> TYPE: DNA
<213> ORGANISM: Artificial
<220> FEATURE:
<223> OTHER INFORMATION: primer sequence

<400> SEQUENCE: 62
aaggatccat ggctaacgtg gctgacacga ag                                32

<210> SEQ ID NO 63
<211> LENGTH: 34
<212> TYPE: DNA
<213> ORGANISM: Artificial
<220> FEATURE:
<223> OTHER INFORMATION: primer sequence

<400> SEQUENCE: 63
ttgcggccgc ttactgatgg gcacactgca ctcc                              34

<210> SEQ ID NO 64
<211> LENGTH: 32
<212> TYPE: DNA
<213> ORGANISM: Artificial
<220> FEATURE:
<223> OTHER INFORMATION: primer sequence

<400> SEQUENCE: 64
aaggatccat gggtaaagac tactaccaga cg                                32

<210> SEQ ID NO 65
<211> LENGTH: 34
<212> TYPE: DNA
<213> ORGANISM: Artificial
<220> FEATURE:
<223> OTHER INFORMATION: primer sequence

<400> SEQUENCE: 65
ttctcgagct atattggaag aacctgctca agta                              34

<210> SEQ ID NO 66
<211> LENGTH: 33
<212> TYPE: DNA
<213> ORGANISM: Artificial
<220> FEATURE:
<223> OTHER INFORMATION: primer sequence

<400> SEQUENCE: 66
aaggatccat ggcatcctac tacgagatcc tag                               33

<210> SEQ ID NO 67
<211> LENGTH: 31
<212> TYPE: DNA
<213> ORGANISM: Artificial
<220> FEATURE:
<223> OTHER INFORMATION: primer sequence

<400> SEQUENCE: 67
ttctcgagtc agaggatgag gcagcgagag g                                 31
```

```
<210> SEQ ID NO 68
<211> LENGTH: 32
<212> TYPE: DNA
<213> ORGANISM: Artificial
<220> FEATURE:
<223> OTHER INFORMATION: primer sequence

<400> SEQUENCE: 68
aaggatccat ggtggactac tacgaggtgc tg                              32

<210> SEQ ID NO 69
<211> LENGTH: 32
<212> TYPE: DNA
<213> ORGANISM: Artificial
<220> FEATURE:
<223> OTHER INFORMATION: primer sequence

<400> SEQUENCE: 69
ttctcgagtc actgaaggca gagaaaaggg gt                              32

<210> SEQ ID NO 70
<211> LENGTH: 30
<212> TYPE: DNA
<213> ORGANISM: Artificial
<220> FEATURE:
<223> OTHER INFORMATION: primer sequence

<400> SEQUENCE: 70
aggatccatg gctccgcaga acctgagcac                                 30

<210> SEQ ID NO 71
<211> LENGTH: 35
<212> TYPE: DNA
<213> ORGANISM: Artificial
<220> FEATURE:
<223> OTHER INFORMATION: primer sequence

<400> SEQUENCE: 71
ttctcgagtc aatatccttg cagtccattg tatac                           35

<210> SEQ ID NO 72
<211> LENGTH: 30
<212> TYPE: DNA
<213> ORGANISM: Artificial
<220> FEATURE:
<223> OTHER INFORMATION: primer sequence

<400> SEQUENCE: 72
aagaattcat ggcgacggcc ttgagcgagg                                 30

<210> SEQ ID NO 73
<211> LENGTH: 33
<212> TYPE: DNA
<213> ORGANISM: Artificial
<220> FEATURE:
<223> OTHER INFORMATION: primer sequence

<400> SEQUENCE: 73
ttctcgagtt atccatctgt atcgatcctg tgg                             33

<210> SEQ ID NO 74
<211> LENGTH: 29
<212> TYPE: DNA
<213> ORGANISM: Artificial
<220> FEATURE:
<223> OTHER INFORMATION: primer sequence

<400> SEQUENCE: 74
```

```
aaggatccat ggcggcgacc gagccggag                                    29
```

<210> SEQ ID NO 75
<211> LENGTH: 35
<212> TYPE: DNA
<213> ORGANISM: Artificial
<220> FEATURE:
<223> OTHER INFORMATION: primer sequence

<400> SEQUENCE: 75

```
ttctcgagtt agccaaattg aaaaagaaa ttccc                              35
```

<210> SEQ ID NO 76
<211> LENGTH: 35
<212> TYPE: DNA
<213> ORGANISM: Artificial
<220> FEATURE:
<223> OTHER INFORMATION: primer sequence

<400> SEQUENCE: 76

```
aagaattcat gaaagattct gaaataaag gtgcc                              35
```

<210> SEQ ID NO 77
<211> LENGTH: 35
<212> TYPE: DNA
<213> ORGANISM: Artificial
<220> FEATURE:
<223> OTHER INFORMATION: primer sequence

<400> SEQUENCE: 77

```
ttctcgagtt aatataaggg cttttggcct tggtt                             35
```

<210> SEQ ID NO 78
<211> LENGTH: 20
<212> TYPE: DNA
<213> ORGANISM: Homo sapiens

<400> SEQUENCE: 78

```
atgaccatga ccctccacac                                              20
```

<210> SEQ ID NO 79
<211> LENGTH: 19
<212> TYPE: DNA
<213> ORGANISM: Homo sapiens

<400> SEQUENCE: 79

```
gactgtggca gggaaaccc                                               19
```

<210> SEQ ID NO 80
<211> LENGTH: 22
<212> TYPE: DNA
<213> ORGANISM: Homo sapiens

<400> SEQUENCE: 80

```
atgttggggt ttgtgggtcg gg                                           22
```

<210> SEQ ID NO 81
<211> LENGTH: 22
<212> TYPE: DNA
<213> ORGANISM: Homo sapiens

<400> SEQUENCE: 81

```
cgatgaatgc tcttcagcca gc                                           22
```

```
<210> SEQ ID NO 82
<211> LENGTH: 22
<212> TYPE: DNA
<213> ORGANISM: Homo sapiens

<400> SEQUENCE: 82
atggaggtgg tggacccgca gc                                              22

<210> SEQ ID NO 83
<211> LENGTH: 22
<212> TYPE: DNA
<213> ORGANISM: Homo sapiens

<400> SEQUENCE: 83
ctgctgcttg caggccgaca gc                                              22

<210> SEQ ID NO 84
<211> LENGTH: 26
<212> TYPE: DNA
<213> ORGANISM: Artificial
<220> FEATURE:
<223> OTHER INFORMATION: primer sequence

<400> SEQUENCE: 84
ggatccatgg ttggttcgct aaactg                                          26

<210> SEQ ID NO 85
<211> LENGTH: 30
<212> TYPE: DNA
<213> ORGANISM: Artificial
<220> FEATURE:
<223> OTHER INFORMATION: primer sequence

<400> SEQUENCE: 85
ctcgagttaa tcattcttct catatacttc                                      30

<210> SEQ ID NO 86
<211> LENGTH: 19
<212> TYPE: DNA
<213> ORGANISM: Artificial
<220> FEATURE:
<223> OTHER INFORMATION: primer sequence

<400> SEQUENCE: 86
tttgcagggc tggcaagcc                                                  19

<210> SEQ ID NO 87
<211> LENGTH: 30
<212> TYPE: DNA
<213> ORGANISM: Artificial
<220> FEATURE:
<223> OTHER INFORMATION: primer sequence

<400> SEQUENCE: 87
ctccagagtt catggtaatg agtgttgagc                                      30

<210> SEQ ID NO 88
<211> LENGTH: 30
<212> TYPE: DNA
<213> ORGANISM: Artificial
<220> FEATURE:
<223> OTHER INFORMATION: primer sequence

<400> SEQUENCE: 88
gctcaacact cattaccatg aactctggag                                      30
```

```
<210> SEQ ID NO 89
<211> LENGTH: 20
<212> TYPE: DNA
<213> ORGANISM: Artificial
<220> FEATURE:
<223> OTHER INFORMATION: primer sequence

<400> SEQUENCE: 89
taatacgact cactataggg                                                 20

<210> SEQ ID NO 90
<211> LENGTH: 22
<212> TYPE: DNA
<213> ORGANISM: Homo sapiens

<400> SEQUENCE: 90
ggcagaatca tgaatgtcat tg                                              22

<210> SEQ ID NO 91
<211> LENGTH: 30
<212> TYPE: DNA
<213> ORGANISM: Artificial
<220> FEATURE:
<223> OTHER INFORMATION: primer sequence

<400> SEQUENCE: 91
ctgaatactt cagagtccaa gaaggtcaag                                      30

<210> SEQ ID NO 92
<211> LENGTH: 30
<212> TYPE: DNA
<213> ORGANISM: Artificial
<220> FEATURE:
<223> OTHER INFORMATION: primer sequence

<400> SEQUENCE: 92
cttgaccttc ttggactctg aagtattcag                                      30

<210> SEQ ID NO 93
<211> LENGTH: 25
<212> TYPE: DNA
<213> ORGANISM: Homo sapiens

<400> SEQUENCE: 93
atgtctgaat atattcgggt aaccg                                           25

<210> SEQ ID NO 94
<211> LENGTH: 23
<212> TYPE: DNA
<213> ORGANISM: Homo sapiens

<400> SEQUENCE: 94
cattccccag ccagaagact tag                                             23

<210> SEQ ID NO 95
<211> LENGTH: 1245
<212> TYPE: DNA
<213> ORGANISM: Homo sapiens

<400> SEQUENCE: 95
atgtctgaat atattcgggt aaccgaagat gagaacgatg agcccattga ataccatcg      60 gaagacgatg ggacggtgct gctctccacg gttacagccc agtttccagg ggcgtgtggg    120
cttcgctaca ggaatccagt gtctcagtgt atgagaggtg tccggctggt agaaggaatt    180
ctgcatgccc cagatgctgg ctggggaaat ctggtgtatg ttgtcaacta tccaaaagat    240
```

```
aacaaaagaa aaatggatga gacagatgct tcatcagcag tgaaagtgaa aagagcagtc    300
cagaaaacat ccgatttaat agtgttgggt ctcccatgga aaacaaccga acaggacctg    360
aaagagtatt ttagtaccct tggagaagtt cttatggtgc aggtcaagaa agatcttaag    420
actggtcatt caaggggtt tggctttgtt cgttttacgg aatatgaaac acaagtgaaa      480
gtaatgtcac agcgacatat gatagatgga cgatggtgtg actgcaaact tcctaattct    540
aagcaaagcc aagatgagcc tttgagaagc agaaaagtgt ttgtggggcg ctgtacagag    600
gacatgactg aggatgagct gcgggagttc ttctctcagt acggggatgt gatggatgtc    660
ttcatcccca agccattcag ggcctttgcc tttgttacat ttgcagatga tcagattgcg    720
cagtctcttt gtggagagga cttgatcatt aaaggaatca gcgttcatat atccaatgcc    780
gaacctaagc acaatagcaa tagacagtta gaaagaagtg aagatttgg tggtaatcca    840 ggtggctttg ggaatcaggg tggatttggt aatagcagag ggggtggagc tggtttggga    900
aacaatcaag gtagtaatat gggtggtggg atgaactttg gtgcgttcag cattaatcca    960
gccatgatgg ctgccgccca ggcagcacta cagagcagtt ggggtatgat gggcatgtta  1020
gccagccagc agaaccagtc aggcccatcg ggtaataacc aaaaccaagg caacatgcag   1080
agggagccaa accaggcctt cggttctgga ataactctt atagtggctc taattctggt    1140
gcagcaattg ttggggatc agcatccaat gcagggtcgg gcagtggttt taatggaggc    1200
tttggctcaa gcatggattc taagtcttct ggctggggaa tgtag                  1245
```

<210> SEQ ID NO 96
<211> LENGTH: 414
<212> TYPE: PRT
<213> ORGANISM: Homo sapiens

<400> SEQUENCE: 96

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg

```
            195                 200                 205
Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
            245                 250                 255

Ile Ser Asn Ala Glu Pro Lys His Asn Ser Asn Arg Gln Leu Glu Arg
        260                 265                 270

Ser Gly Arg Phe Gly Gly Asn Pro Gly Gly Phe Gly Asn Gln Gly Gly
    275                 280                 285

Phe Gly Asn Ser Arg Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Gln Ala Ala Leu Gln Ser Ser Trp Gly Met
            325                 330                 335

Met Gly Met Leu Ala Ser Gln Gln Asn Gln Ser Gly Pro Ser Gly Asn
        340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 97
<211> LENGTH: 24
<212> TYPE: DNA
<213> ORGANISM: Homo sapiens

<400> SEQUENCE: 97
gcggactatg acttagttgc gtta                                          24

<210> SEQ ID NO 98
<211> LENGTH: 23
<212> TYPE: DNA
<213> ORGANISM: Homo sapiens

<400> SEQUENCE: 98
accttcaccg ttccagtttt taa                                           23

<210> SEQ ID NO 99
<211> LENGTH: 22
<212> TYPE: DNA
<213> ORGANISM: Homo sapiens

<400> SEQUENCE: 99
ccctggtatg agcccatcta tc                                            22

<210> SEQ ID NO 100
<211> LENGTH: 22
<212> TYPE: DNA
<213> ORGANISM: Homo sapiens

<400> SEQUENCE: 100
aaagtagacc tgcccagact cg                                            22
```

```
<210> SEQ ID NO 101
<211> LENGTH: 20
<212> TYPE: DNA
<213> ORGANISM: Homo sapiens

<400> SEQUENCE: 101
aagttcttat ggtgcaggtc                                              20

<210> SEQ ID NO 102
<211> LENGTH: 19
<212> TYPE: DNA
<213> ORGANISM: Homo sapiens

<400> SEQUENCE: 102
tgcagtcaca ccatcgtcc                                               19
```

METHOD FOR IDENTIFYING TARGET PROTEIN OF DRUG AND METHOD FOR SCREENING THERAPEUTIC AGENT FOR DIABETES USING THE TARGET PROTEIN

CROSS-REFERENCE TO RELATED APPLICATIONS

This application is a 371 National Stage Entry of International Application No. PCT/JP2006/315745 filed on Aug. 9, 2006 and claims the benefit of Japanese Patent Application Nos. P. 2005-234673 filed on Aug. 12, 2005, and P. 2005-279582 filed Sep. 27, 2005 in the Japanese Intellectual Property Office, the disclosures of each of which are incorporated herein in their entirety by reference.

TECHNICAL FIELD

The present invention relates to a method for identifying the target protein of a compound having a pharmacological action by detecting a tertiary structural change of the target protein by binding a compound having a pharmacological action to said target protein, with the use of a chaperone protein having a characteristic of binding to the protein by recognizing a tertiary structural change of the protein.

The present invention also relate to a method for screening therapeutic agent for diabetes using a target protein found by the identification method of the present invention.

BACKGROUND OF THE INVENTION

A large number of low molecular compounds used as pharmaceutical agents are still unclear in regard to their mechanism of action despite their distinct pharmacological actions. In general, most of the pharmaceutical agents act upon specific proteins in vivo and alter functions of the proteins, and induce pharmacological actions as a result. In the agents whose mechanisms of action are unclear, proteins as their targets have not been identified. In recent years, as a result of advances in the elucidation of signal transduction system in vivo at the molecular level, a large number of specific protein molecules necessary for inducing specific pharmacological actions have been identified. As a result, development of the agents so-called molecule targeting agents which target at such specific protein molecules is in progress recently, and their ratio is rapidly increasing. In the case of a compound whose target protein is evident, its in vivo functional mechanism is clear, and structure of the compound can be modified with the use of its strength to bind to said protein, or a change in the enzyme activity possessed by the protein, as the index. Thus, it is easy to carry out studies with the aim of improving pharmacokinetics including absorption and degradation, as well as pharmacological activity, so that it is markedly advantageous in developing agents. In the case of a compound whose target protein is unclear to the contrary, it is not easy to attempt improvement of its chemical structure for the purpose of improving the activity, even when distinct pharmacological action is found (cf. Non-patent Reference 1).

In addition, though there are differences in degree, pharmaceutical agents generally have both desirable pharmacological actions (principal effects) and undesirable pharmacological actions (adverse side effects). Even in the case of molecule targeting agents whose target proteins carry the principal effects and are already put on the market, there are many cases in which information on the target proteins concerned in the adverse side effects is scanty, and this causes a problem requiring time and cost for studying improvement for avoidance of the adverse side effects (cf. Non-patent Reference 1).

In fact, there are a large number of pharmaceutical agents whose significant pharmacological actions are known but their target proteins are unclear. As representative examples, biguanide which has been used for a long time as an agent for treating diabetes (cf. Non-patent Reference 2) and thalidomide in which its presence has been reconsidered in view of its drastic therapeutic effect on multiple myeloma may be cited (cf. Non-patent Reference 3). Though biguanide has a significant hypoglycemic action, and thalidomide a significant angiogenesis inhibitory action, direct target protein for each of these agents in vivo has not been identified. Thus, in spite of the useful pharmacological actions possessed by these agents, it was difficult to carry out improvement studies for enhancing the effects. In addition to this, serious adverse side effects such as lactic acidosis by biguanide (cf. Non-patent Reference 4) and teratogenicity by thalidomide (cf. Non-patent Reference 3) are known, but studies for avoiding these problems have not been advanced, because their targets are unclear. Thus, identification of the target proteins of these agents is in demand.

Conventionally, a method in which a protein which directly binds to a low molecular compound is detected and separated by physical and/or chemical means was a general means for identifying a target protein upon which said compound acts. For example, a method is known in which a part of the structure of a compound is modified and bind to high molecular weight affinity beads, and a target protein bound to the compound is separated and purified by gravity or the like physical force. Also, a method is carried out in which a tag to be used as a label is attached to a part of the structure of a compound and the target protein bound to said compound is chemically detected (cf. Non-patent Reference 5). In recent years, attempts have also been made to screen and identify, from a cDNA library, a gene fragment coding for a protein which binds to the compound of interest, by a yeast two hybrid method (cf. Non-patent Reference 6), a phage display method (cf. Non-patent Reference 7) and the like molecular biological techniques.

However, in spite of the aforementioned attempts by various methods, a case in which a target protein of an agent was actually identified from the studies in this field so far is not many. The reasons for the low frequency of success include that it is necessary to modify a part of the structure of a compound because beads or a tag is bound to the compound to be used as the probe in every case of the aforementioned methods, so that it is unavoidable to screen for a protein which binds to an artificial structure different from the original compound (cf. Non-patent References 1 and 5). That is, this becomes a reason of mistakenly identifying, as the target protein, a nonspecific protein which binds to a tag, beads, a complex thereof with a compound, or the like artificial substance which is different from the agent having original pharmacological activity. In addition, though it is essential, for the purpose of finding the true target protein, to apply modification of the structure of a compound to a region which does not exert influence upon the pharmacological action of said compound, agents and compounds having unclear targets are generally poor in information on the correlation between their structures and pharmacological activities, so that there are many cases in which compounds modified at optional regions have to be used. Because of this, there is a high frequency of selecting a compound which lost its original pharmacological activity as the probe. Essentially, it is desirable to verify firstly that said compound to which a tag or bead is added by modification is still keeping its original pharmacological activity and then use it as the probe, but since cell membrane permeability, stability and the like various parameters exert influences, it is not easy to judge the presence or absence of the pharmacological activity. Also, since modification of the structure of compounds requires time, cost and special techniques, these cause the aforementioned methods to hardly become a general purpose studying means.

On the other hand, it is possible to verify binding of a specified protein to a compound labeled by replacing an element in the molecule of a compound with a radioisotope (its structure is the same as the before labeling), but since it is not a fixable modification, it is not easy to screen the target protein from a large number of proteins. In addition, this method has a disadvantage in that the compound becomes unstable by the labeling and the cost runs up.

As another reason of the low success ratio of compound target screening by the conventional methods, a point can be exemplified that since each of the aforementioned methods carries out detection and separation of a target making use of the direct binding of a compound with a protein as the index, it is difficult to achieve target finding when the binding affinity between the compound and the target protein is low. Actually, in each of the only few cases of succeeding in finding a target by the aforementioned methods, the binding affinity between the compound and the protein is high (cf. Non-patent Reference 4). However, the degree of pharmacological activity of a compound and its binding affinity for a target protein do not always have a correlation based on the knowledge so far obtained. Rather, it is considered that strong binding of a compound to target protein may not be necessary for the induction of pharmacological action excluding irreversible inhibition (cf. Non-patent Reference 8). Based on the above problems, concern has been directed toward a method for identifying target proteins of agents, which were not able to be found by the conventional methods.

Molecular chaperone is a group of proteins which assist structure formation of protein, such as folding or denaturation (unfolding) of a protein molecule, multimer formation and the like (cf. Non-patent Reference 9). It is known now that a large number of molecules generally referred to as heat shock protein, in which its expression is accelerated by heat stimulation, act as chaperone. Among the molecular chaperones, a group of molecules generally referred to as Hsp60 family are particularly called "chaperonin" as a typical molecular chaperone.

These molecular chaperones represented by the heat shock protein interact with unstable proteins before completion of their tertiary structures in their translation process and keep them stably, and also have the action to maintain and control the protein structure such that influences upon the function of intracellular protein are not caused accompanied by an environmental change and to accelerate ubiquitination and subsequent degradation of substrate which became an abnormal state (cf. Non-patent Reference 10).

Thus, the chaperone has a property as a functional molecule which recognizes non-natural structure of a protein molecule as the substrate.

On the other hand, a screening method for identifying the ligand of already known target protein has been reported, which uses molecular chaperon for the determination of the degree of folded state and unfolded state of the target protein in the presence or absence of a ligand candidate (cf. Non-patent References 1 to 6).

Insulin is secreted from the β cell of pancreatic islets of Langerhans and reduces blood sugar level by acting mainly upon muscles, the liver and fat to store and consume blood sugar through its intake into cells. Diabetes is induced by the insufficient action of this insulin, and there are two types in its patients, namely, type I having a disorder in the production or secretion of insulin, and type II in which acceleration of glucose metabolism by insulin becomes difficult to occur. Though the blood sugar level becomes higher than that of healthy people in both of these patients, blood insulin becomes absolutely scarce in type I, while insulin resistance in which intake or consumption of blood sugar by cells is not accelerated in spite of the presence of insulin is generated in type II. The type II diabetes is a so-called life style-related disease which is induced by overeating, less exercise, stress and the like causes in addition to hereditary basic factor. These days, this type II patient is rapidly increasing in advanced nations accompanied by the increase of caloric intake, and it occupies 95% of diabetes patients in Japan. Thus, the necessity of not only a simple hypoglycemic agent but also treatment of type II diabetes for accelerating glucose metabolism through the improvement of insulin resistance is increasing as agents for treating diabetes.

Currently, insulin injections are prescribed for the treatment of type I diabetes patients. On the other hand, as the hypoglycemic agent prescribed for type II diabetes patients, a sulfonylurea system hypoglycemic agent (SU agent) which accelerates secretion of insulin by acting upon β cells of the pancreas and an α-glucosidase inhibitor which delays digestion absorption of glucose are known, in addition to the insulin injections. Though these improve insulin resistance indirectly, a thiazolidine derivative has been used in recent years as an agent which more directly improves insulin resistance. Its action is to accelerate intake of glucose into cells and use of glucose in the cells. It has been shown that this thiazolidine derivative acts as an agonist of peroxisome proliferator activated receptor gamma (PPAR γ) (cf. Non-patent Reference 11). However, it is known that the thiazolidine derivative not only improves insulin resistance but also has adverse side effects of inducing fat accumulation and edema (cf. Non-patent Reference 12). Since this induction of edema is a serious adverse side effect which results in cardiac hypertrophy, more useful new drug target molecule instead of PPAR γ is in demand for the improvement of insulin resistance. As a leading agent which produces a glucose metabolism improving action other than these, a hypoglycemia agent biguanide which has been used for a long time is known (cf. Non-patent Reference 13). The biguanide agent has been reported to have actions to enhance glucose metabolism by anaerobic glycolytic action, suppression of gluconeogenesis, suppression of appetite and suppression of intestinal absorption of glucose, and as a result, biguanide improves insulin sensitivity in the liver and muscles. Since biguanide does not act upon the pancreas and does not increase secretion of insulin, it has a characteristic in that it does not cause obesity and hardly cause hypoglycemia. The action of biguanide does not include undesirable actions possessed by the aforementioned thiazolidine derivative and insulin preparations, and there are many cases in which it is prescribed in combination with the aforementioned other hypoglycemic agents in reality. Combined with the recent year's reconsideration on its strong pharmacological action, the biguanide agent now holds its position net to the thiazolidine derivative as insulin resistance improving agent. But on the other hand, it is known that biguanide agent has an adverse side effect of causing lactic acidosis by increasing accumulation of lactic acid (cf. Non-patent Reference 14). In spite of the very old history of biguanide as an agent, a distinct target protein, like the case of PPARγ of the thiazolidine derivative, has not been identified yet. Since information on the structural activity correlation regarding biguanide agents and the target protein has not been obtained, not only a dissociate study on adverse side effect such as improvement of lactic acidosis but also an improvement study aimed at increasing hypoglycemia as the principal effect has been difficult to carry out up to the present. ATP5B protein is the β subunit of F1F0-ATP synthase, which is encoded on the genome and perform its action after transferred to mitochondria (cf. Non-patent References 15 and 16). Also, regarding the existing amounts of ATP5B, it has been reported that both of the amounts of its gene expression and protein amount are lowered in muscles of type II diabetes patients in comparison with those of healthy people (cf. Non-patent References 17 and 18 and Patent Reference 7). In addition, it has been reported that phosphorylation level of ATP5B in muscles of diabetes patients and fasting blood sugar level take inverse correlation (cf. Non-patent Reference 18 and Patent Reference 7), and those (e.g., a nucleic acid fragment) which control expression of ATP5B, a polypeptide, an antibody, a polynucleotide or a compound which binds to a polypeptide, and the like can be agents for treating diabetes-associated diseases (cf. Patent Reference 7). There is a report which discloses various polypeptides (3025 substances) included in human heart mitochondrial proteome including ATP5B, and describes that these are related to the screening for an agent for treating diseases (including diabetes) associated with mitochondrial functions (cf. Patent Reference 8). However, there are no reports stating that ATP5B protein binds to biguanide.

Patent Reference 1: U.S. Pat. No. 5,585,277
Patent Reference 2: U.S. Pat. No. 5,679,582
Patent Reference 3: US Patent Application Publication No. 2002/055123
Patent Reference 4: US Patent Application Publication No. 2004/191835
Patent Reference 5: Japanese Patent No. 2952848
Patent Reference 6: European Patent No. 0770876
Patent Reference 7: International Publication No. 03/020963
Patent Reference 8: International Publication No. 03/087768
Non-patent Reference 1: "The Journal of Antibiotics" H. Hatori et al., 2004 vol. 57 no. 7 p. 456-461
Non-patent Reference 2: "Nippon Rinsho (Japan Clinics)" Y. Yamacaki et al., 2002 vol. 60 no. 9 p. 389-92
Non-patent Reference 3: "Drug Discovery Today" Teo S K et al., 2005 vol. 15 no. 10(2) p. 107-114
Non-patent Reference 4: "Drugs" Lalau J D et al., 1999 vol. 58 no. 1 p. 55-60/75-82
Non-patent Reference 5: "Nature Biotechnology" (England) 2000, N. Shimizu et al., vol. 18, p. 877-881
Non-patent Reference 6: "Biochemical Pharmacology" 2002, D. Henthorn et al., vol. 63 no. 9 p. 1619-1628
Non-patent Reference 7: "Chemistry & Biology" Sche P P et al., vol. 6 no. 10: p. 707-716. PMID: 10508685
Non-patent Reference 8: "Biochemistry (OUTLINES OF BIOCHEMISTRY)" 1987, Eric E. CONN et al.
Non-patent Reference 9: "Pharmacology & Therapeutics" 2004, A. Sreedhar et al., vol. 101 no. 3 p. 227-257
Non-patent Reference 10: "Nature" 1992, Gething M J, Sambrook J. et al., vol. 355 no. 6355: p. 33-45
Non-patent Reference 11: "The Journal of Biological Chemistry", (USA), 1995, vol. 270, p. 12953-12956
Non-patent Reference 12: "Diabetes Frontier", (USA), 1999, vol. 10, p. 811-818
Non-patent Reference 13: "Nippon Rinsho (Japan Clinics)" Y. Yamasaki et al., 2002 vol. 60 no. 9 p. 389-92
Non-patent Reference 14: "Drugs" Lalau J D et al., 1999 vol. 58 no. 1 p. 55-60/75-82
Non-patent Reference 15: "Nature" (USA), 1997, vol. 386, p. 299-302
Non-patent Reference 16: "Nature" (USA), 1994, vol. 370 (6491), p. 621-628
Non-patent Reference 17: "Diabetes" 2002, vol. 51, p. 1913-1920
Non-patent Reference 18: "The Journal of Biological Chemistry" 2003, vol. 278, p. 10436-10442

DISCLOSURE OF THE INVENTION

Problems that the Invention is to Solve

The present invention aims at providing a method for identifying a target protein of a low molecular compound, with the use of not the binding of said compound with a protein but a change in the tertiary structure of protein responding to the compound as the index, and without requiring structural modification of the aforementioned compound.

Also, the present invention aims at providing a method for screening for a novel agent for treating diabetes.

Means for Solving the Problems

When a compound acts and thereby exerts influence upon the function of a target protein, it is expected that tertiary structure of said protein undergoes a change by its interaction with the compound. Thus, it is considered that the factor necessary for the pharmacological action produced by the compound is not a simple binding between the compound and the target but a change in the tertiary structure of the target protein by the action of the compound. Accordingly, the present inventors have considered that when it is possible to screen a protein making use of said change as the index, a true target protein which carried pharmacological action of a compound can be screened with a probability of higher than conventional compound target screening means. In addition, by developing a method for picking up and detecting the aforementioned change not from the compound side but from the side of a target protein in response to the compound, identification of the target protein of said compound was realized without requiring compound structure modification which was unavoidable by the conventional methods.

That is, the inventors have found that a molecular chaperone protein known as a functional molecule which recognizes non-natural structure of a protein as the substrate recognizes a change of the tertiary structure of protein by a compound (an agent whose target protein is unknown), and thereby have constructed a method for detecting and identifying a target protein of a compound (an agent whose target protein is unknown) making use, as the index, of a change in the binding of an intracellular protein with a molecular chaperone protein. Illustratively, the inventors have succeeded in detecting estrogen receptor as the target protein of a low molecular compound 17β-estradiol (Example 2), and also have succeeded in detecting FKBP12 as the target protein of FK506 and FK1706, detecting glucocorticoid receptor as the target protein of dexamethasone, detecting androgen receptor as the target protein of dihydrotestosterone, detecting mineralcorticoid receptor as the target protein of androsterone and detecting hydrofolate reductase as the target protein of methotrexate (Example 3). Also, we have succeeded in detecting and identifying the target protein of an agent for treating diabetes, biguanide, whose target protein was unclear in the past, and have fount that this is ATP5B (Example 4). In addition, by the method of the present invention, we have succeeded in finding TARDBP as the target protein of thalidomide whose target protein was unclear up to this time (Example 8).

Also, we have revealed that, when the aforementioned ATP5B protein as the β subunit of F1F0-ATP synthase existing on the mitochondria membrane, whose function to bind to a diabetes-treating agent biguanide has been found by the inventors, is excessively expressed in a cell, activation of intracellular AMP kinase (to be referred to as AMPK hereinafter) by biguanide is obstructed (Example 5). Based on these findings, the inventors have revealed that the ATP5B protein is the target protein concerned in the pharmacological action (principal effect) of biguanide, and thereby constructed a new screening method of an agent for treating diabetes, which uses said protein. By finding that a substance obtained by the screening method of the present invention certainly has the diabetes-treating effect and does not have adverse side effects, new screening tool and screening method of an agent for treating diabetes and a pharmaceutical composition for diabetes treatment were provided.

That is, the present invention relates to:

<1> a method for screening for an agent for treating diabetes, which comprises
[1] a step of allowing (1) a polypeptide consisting of the amino acid sequence represented by SEQ ID NO:2, (2) a polypeptide which comprises the amino acid sequence represented by SEQ ID NO: 2 or an amino acid sequence of SEQ ID NO:2 wherein 1 to 10 amino acids thereof are deleted, substituted and/or inserted, and which also binds to biguanide and/or inhibits activation of AMPK by biguanide due to over-expression, (3) a polypeptide which comprises an amino acid sequence having 90% or more of homology with the amino acid sequence represented by SEQ ID NO:2 and which also binds to biguanide and/or inhibits activation of AMPK by biguanide due to over-expression, or (4) a cell transformed with a vector which comprises a polynucleotide coding for the polypeptide described in (1) to (3), to be in contact with a substance to be tested, and
[2] a step of analyzing binding of said polypeptide with the substance to be tested, <2> the screening method described in <1>, wherein the step of [1] is a contacting step in the coexistence of biguanide, <3> the screening method described in <1> or <2>, which further comprises a step of confirming that it activates AMPK activity and/or has a therapeutic activity for diabetes, <4> a screening tool for an agent for treating diabetes having the same medicinal target with biguanide, which consists of (1) the polypeptide described in <1>, (2) a polynucleotide coding for the polypeptide described in <1> or (3) the transformed cell described in <1>, <5> use of (1) the polypeptide described in <1>, (2) a polynucleotide coding for the polypeptide described in <1> or (3) the transformed cell described in <1>, for the screening of an agent for treating diabetes having the same medicinal target with biguanide, <6> a pharmaceutical composition for treating diabetes, which comprises a substance obtained by the method described in <1> to <3>, <7> a method for treating diabetes, which comprises administering an effective amount of a substance obtained by the method described in <1> to <3> to a subject in need of diabetes treatment, <8> use of a substance obtained by the method described in <1> to <3> for the manufacture of a pharmaceutical composition for treating diabetes, <9> a method for identifying a target protein of an agent to be tested, which comprises

[1] (1) a step of allowing an agent to be tested, a molecular chaperone protein and a sample cell protein to be in contact with each other, and
(2) a step of detecting a protein which binds to the molecular chaperone protein, [2] (3) a step of allowing a molecular chaperone protein to be in contact with a sample cell protein, and
(4) a step of detecting a protein which binds to the molecular chaperone protein, and
[3] a step of comparing the protein detected by (2) with the protein detected by (4), <10> the identification method described in <9>, wherein the molecular chaperone protein is a protein consisting of a polypeptide which comprises an amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27 wherein 1 to 10 amino acids thereof are deleted, substituted and/or inserted and also binds to a protein by recognizing a change in the tertiary structure of the protein, or consisting of a polypeptide which comprises an amino acid sequence having 90% or more of identity with the amino acid sequence represented by SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27 and also binds to a protein by recognizing a change in the tertiary structure of the protein, and <11> the identification method described in <9>, wherein the molecular chaperone protein is a protein consisting of the amino acid sequence represented by SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18. SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27.

On the priority date of this application, properties of molecular chaperone as a functional molecule which recognizes a non-natural structure of a protein molecule that becomes the substrate (Non-patent Reference 9 and Non-patent Reference 10) and a method for identifying a ligand of an already known protein using molecular chaperone were known (Patent References 1 to 6), but a method for identifying a target protein of a low molecular compound using molecular chaperone was not known.

On the priority date, reduction of the existing amount of ATP5B in muscles of type II diabetes patients (cf. Non-patent References 17 and 18 and Patent Reference 7) and inverse correlation between phosphorylation level of ATP5B in muscles of diabetes patients and fasting blood glucose level (cf. Non-patent Reference 18 and Patent Reference 7) were known, but the Patent Reference 7 describes that the ATP5B itself and antibodies become agents for treating diseases associated with diabetes, but it was unclear about the way of regulating expression of ATP for generating therapeutic effect of diabetes. There is a report which discloses various polypeptides (3025 substances) included in human heart mitochondrial proteome including ATP5B, and describes that these are related to the screening of a therapeutic agent for diseases including diabetes related to a large number of mitochondrial functions (cf. Patent Reference 8), but there is no basis that ATP5B is related to the screening of an agent for treating diabetes. In addition, in a reference opened to the public after the priority date of this application (International Publication No. 2005/090992), polypeptides including ATP5B as two or more modifiers of the PTEN pathway are disclosed, and a system for detecting binding of these modifiers with a candidate compound is disclosed, but a relationship between an agent specifically binding to the modifier and diabetes is not described or suggested. Since there are no reports in these references stating that ATP5B protein and biguanide bind together, binding of ATP5B protein and biguanide is the knowledge found for the first time by the present inventors, and the diabetes treating agent-screening method which uses ATP5B and has the principal effect similar to that of biguanide (particularly a diabetes treating agent-screening method which uses ATP5B and is carried out in the coexistence of biguanide) is an invention carried out for the first time by the present inventors.

Advantage of the Invention

The method of the present invention for identifying a target protein which responds to a compound with the use of a change in the tertiary structure of the target protein as the index, without requiring structural modification of the compound and without using binding strength of said compound and target protein as the index, is useful as an identification method of target proteins useful in studying improvement of already existing agents, and is a novel means which sweeps away various problems present in the conventional screening methods of compound target proteins.

By the screening method of the present invention which uses the screening tool of the present invention (e.g., ATP5B which is the target protein of biguanide), a compound which becomes an agent for treating diabetes and has a new structurally-non-analogous mother compound can be obtained, in addition to a structurally-analogous compound o biguanide. This structure-non-analogous compound can become a new diabetes-treating agent which does not cause obesity as a characteristic of biguanide and also has an effect of hardly causing hypoglycemia. In addition to this, by the use of the binding with ATP5B protein as the index, it becomes possible to modify molecular structure of the obtained compound while keeping its principal effect, so that it becomes possible to develop an agent for treating diabetes having more high principal effect and more reduced adverse side effect in comparison with the conventional biguanide agents.

BRIEF DESCRIPTION OF THE DRAWINGS

FIG. 1 is an illustration showing a band of ERα in which its change was detected E2-dependent manner by a pull-down method which used a molecular chaperone protein as the probe. Lanes 1 and 2 show results of using GST, and lanes 3 to 6 results of using GST-HSPA4.

FIG. 2 is an illustration showing binding of human ATP5B with phenformin. The "+" in the drawing shows a case of adding MTX-phenformin, and "−" a case of not adding MTX-phenformin. The "Inp." represents input.

FIG. 3 is an illustration showing disappearance of the phenformin binding ability by the mutation of human ATP5B. The "WT" shows a case of using wild type ATP5B, and the "E175V" using Glu175Val mutation type ATP5B, and "D295V" using Asp295Val mutation type ATP5B. The "+" in the drawing shows a case of adding MTX-phenformin, and "−" a case of not adding MTX-phenformin. The "Inp." represents input.

FIG. 4 is an illustration showing disappearance of the AMPK activation ability of phenformin (PF) by the over expression of human ATP5B. The upper panel shows a result of using an anti-phospho AMPK antibody, and the lower panel a result of using an anti-AMPKα antibody. The "+" in the drawing shows a case of adding phenformin (PF), and "−" a case of not adding phenformin (PF).

FIG. 5 is a graph showing binding of human ATP5B with MTX-phenformin (MTX-PF), which depends on the concentration of phenformin (PF). The axis of ordinate shows counts (amount of ATP5B).

FIG. 6 is a graph in which, in a test showing binding of human ATP5B with phenformin, a substance to be tested (free phenformin; PF) is allowed to be in contact with each other, and whether or not it exerts influence upon the binding was detected. The axis of ordinate shows counts (amount of ATP5B).

FIG. 7 is a graph in which, in a test showing binding of human ATP5B with phenformin, a substance to be tested (compound A or compound B) is allowed to contact, and whether or not it exerts influence upon the binding was detected. The axis of ordinate shows counts (amount of ATP5B).

FIG. 8 is a graph showing that compound A and compound B show hypoglycemic action without causing in vivo accumulation of lactic acid. It shows periodical changes in the blood sugar value (A) and lactic acid value (B), 0 minute, 90 minutes and 180 minutes after intraperitoneal administration of compound A (open square), metformin (closed circle) or solvent (closed diamond) to db/db mice. In the same manner, periodical changes in the blood sugar value (C) and lactic acid value (D) are shown, 0 minute, 90 minutes and 180 minutes after intraperitoneal administration of compound B (closed square), metformin (closed circle) or solvent (closed diamond) to db/db mice. In each of A and C, the value at each measuring time in the solvent administration group is regarded as 100 based on the measured value at 0 minute, and relative values based on these are expressed, wherein the axis of ordinate shows rate of change in blood sugar value (%). In each of B and D, the measured value at 0 minute is regarded as 100, and relative values based on these are expressed, wherein the axis of ordinate shows rate of change in lactic acid value (%). The symbol * indicates the p value by the significance test is 0.05 or less, and ** 0.01 or less in the same manner.

FIG. 9 is a graph showing expression quantity of TARDBP in HeLa S3 cell transferred with pcDNA-TARDBP. The axis of ordinate shows the value of TARDBP/β-actin.

FIG. 10 is a graph showing influence of thalidomide (Tha) upon the production of TNF-α by okadaic acid (OA) in empty vector-transferred cell or pcDNA-TARDBP-transferred cell. The axis of ordinate shows the value of TNF-α/β-actin.

BEST MODE FOR CARRYING OUT THE INVENTION

The following describes the present invention in detail. The gene manipulation techniques in this description can be carried out in accordance with the conventionally known techniques of "Molecular Cloning" Sambrook, J. et al., Cold Spring Harbor Laboratory Press, 1989, and the like unless otherwise noted, and the protein manipulation techniques can be carried out in accordance with the conventionally known techniques of "*Tanpaku Jikken Protocol* (Protein experiment Protocol)" (Shujun-sha, 1997) and the like unless otherwise noted.

One of the present invention is a method for identifying a protein (target protein) whose tertiary structure was changed in response to a compound with the use of a molecular chaperone protein which is a protein having a function to recognize a change in the tertiary structure of a protein in vivo, by inclusively examining difference in the change of binding of molecular chaperone with an endogenous protein (target protein) at the time of adding or not adding a specific compound (an agent whose target protein is unclear), thereby selecting a protein whose binding amount is increased only when an agent to be tested is added or whose binding amount is reduced only when the agent to be tested is added.

The identification method of the present invention is a method for identifying a target protein of an agent to be tested, which comprises

[1] (1) a step of allowing an agent to be tested, a molecular chaperone protein and a sample cell protein to be in contact with each other, and (2) a step of detecting a protein which binds to the molecular chaperone protein,

[2] (3) a step of allowing a molecular chaperone protein to be in contact with a sample cell protein, and (4) a step of detecting a protein which binds to the molecular chaperone protein, and

[3] a step of comparing the protein detected by (2) with the protein detected by (4)

The sample cell protein according to this description means a group of proteins contained (expressed) in a cell considered to be containing the target protein to be screened (to be referred to as "sample cell" hereinafter). According to the identification method of the present invention, it is not limited by the contacting order, condition of the molecular chaperone protein (whether it is isolated, expressed in a cell or contained in a cell extract) and condition of the sample cell protein (whether it is expressed in an intact cell or contained in a cell extract), with the proviso that the agent to be tested, the molecular chaperone protein and the sample cell protein are contacted with one another. That is, the identification method of the present invention includes a method which uses an isolated and purified molecular chaperone protein and a sample cell protein contained in a sample cell extract (the first identification method), a method which uses a molecular chaperone protein expressed in a sample cell transformed with a vector comprising a partial or whole length region of a polynucleotide coding for the molecular chaperone protein and a sample cell protein expressed in the transformed sample cell (intact cell) (the second identification method), and a method which uses a molecular chaperone protein under a condition of being contained in the aforementioned extract of transformed cell and a sample cell protein under a condition of being contained in the same extract (the third identification method).

In the first identification method of the present invention, the molecular chaperone molecule is isolated. For example, it is produced in a large amount by expressing a partial or whole length region of the molecular chaperone molecule or a partial or whole length region of the molecular chaperone molecule fused with GST, Flag, His or the like tag in *Escherichia coli* or the like bacterium, yeast an insect cell or the like, or by a chemical synthesis method, and then it can be purified using an antibody of the molecular chaperone protein, antibodies of various tags fused to the molecular chaperone protein or affinity beads or affinity column having high affinity for the tag. Alternatively, it is also possible to produce and purify the molecular chaperone protein by effecting transcription and translation of a DNA fragment of the molecular chaperone gene in vitro. In the first identification method of the present invention, the purified molecular chaperone protein is mixed and contacted with a protein mixed liquid extracted from a sample cell (namely a liquid containing a sample cell protein) in vitro under a condition of adding or not adding an agent to be tested, and then both the molecular chaperone protein and proteins binding thereto are concentrated in accordance with the method described above. Preferably, a protein derived from a sample cell which binds to the molecular chaperone protein only when an agent to be tested is not added, or a protein derived from a sample cell which binds to the molecular chaperone protein only when an agent to be tested is added, can be detected by the methods described in Example 2(2) (3), 3, 4 or 8.

The second identification method of the present invention is a method for identifying a target protein of an agent to be tested, which comprises

[1] (1) a step of allowing an agent to be tested, a molecular chaperone protein expressed in a sample cell transformed with a vector comprising a polynucleotide coding for the molecular chaperone protein, and a sample cell protein expressed in the aforementioned transformed cell to be in contact with each other, and (2) a step of detecting a protein which binds to the molecular chaperone protein,

[2] (3) a step of allowing a molecular chaperone protein expressed in a sample cell transformed with a vector comprising a polynucleotide coding for molecular chaperone protein to be in contact with a sample cell protein expressed in the aforementioned transformed cell, and (4) a step of detecting a protein which binds to the molecular chaperone protein, and

[3] a step of comparing the protein detected by (2) with the protein detected by (4).

The third identification method of the present invention is a method for identifying a target protein of an agent to be tested, which comprises

[1] (1) a step of allowing an agent to be tested, a molecular chaperone protein under a condition of being contained a cell extract of a sample cell transformed with a vector comprising a polynucleotide coding for the molecular chaperone protein and a sample cell protein under a condition of being contained in the aforementioned extract to be in contact with each other, and (2) a step of detecting a protein which binds to the molecular chaperone protein,

[2] (3) a step of allowing a molecular chaperone protein under a condition of being contained a cell extract of a sample cell transformed with a vector comprising a polynucleotide coding for the molecular chaperone protein to be in contact with a sample cell protein under a condition of being contained in the aforementioned extract, and (4) a step of detecting a protein which binds to the molecular chaperone protein, and

[3] a step of comparing the protein detected by (2) with the protein detected by (4).

The second identification method and the third identification method of the present invention include a step of transforming a cell considered to be containing the target protein to be screened with a vector comprising a partial or whole length region of a polynucleotide coding for the molecular chaperone protein, and expressing a partial or whole length region of a polypeptide as the molecular chaperone protein, or a partial or whole length region of said polypeptide to which GST, Flag, His or the like tag is fused, in said cell. In the second identification method, a compound desired to screen its target protein (to be referred to as agent to be tested hereinafter) is added (contacted) or not added (un-added) to the aforementioned transformed cell of a living state. By this, the molecular chaperone protein expressing in the aforementioned transformed sample cell, a sample cell protein and a sample agent, or the molecular chaperone protein expressing in the aforementioned transformed sample cell and the sample cell protein, can be contacted. In the third identification method, an agent to be tested is added (contacted) or not added (un-added) to a protein mixed liquid extracted from the aforementioned transformed cell (namely a sample cell extract containing a molecular chaperone protein and a sample cell protein). By this, the molecular chaperone protein under a state of being contained in an extract of the aforementioned transformed sample cell, the sample cell protein under a state of being contained in the same extract and the sample agent, or the molecular chaperone protein under a state of being contained in an extract of the aforementioned transformed sample cell and the sample cell protein under a state of being contained in the same extract, can be contacted.

In the second identification method and the third identification method of the present invention, the protein binding to the molecular chaperone protein is concentrated in accordance with the same method of the first identification method.

<Molecular Chaperone Protein>

As the molecular chaperone protein which can be used in the identification method of the present invention, any conventionally known molecular chaperone protein can be used. Illustratively, typical proteins belonging to the respective families of Hsp90 (HtpG; the parenthesized part shows name of *Escherichia coli*), Hsp70 (DnaJ), Hsp60 (GroEL), Hsp40 (DnaJ), Hsp27 (IbpAB), Hsp104 (C1pB) and GRP78 (DnaK) can be exemplified (A. Sreedhar et al., *Pharmacology & Therapeutics,* 2004, vol. 101, no. 3, p. 227-257; D. S. Latchman et al., *Cardiovascular Research,* 2001, vol. 51, p. 637-646). In addition, FKBP56 and Hsp32 known as heme oxygenase-1, low molecular sHSPs (small heat shock proteins) and the like can also be used as chaperones (P. Laksanalamai, Extremphiles, 2004, vol. 8, no. 1, p. 1-11).

As the molecular chaperone protein which can be used in the identification method of the present invention, a conventionally known molecular chaperone or a polypeptide which comprises an amino acid sequence representing a conventionally known molecular chaperone protein wherein 1 to 10 (preferably 1 to 7, more preferably 1 to 5, further preferably 1 to 3) amino acids thereof are deleted, substituted and/or inserted, and also binds to a protein by recognizing a change in tertiary structure of said protein (to be referred to as "functionally equivalent variant" hereinafter) is included. Also, a polypeptide which comprises an amino acid sequence having 90% or more (preferably 95% or more, more preferably 98% or more) of identity with the amino acid sequence representing the above-described known molecular chaperone protein, also binds to a protein by recognizing a change in tertiary structure of said protein (to be referred to as "homologous polypeptide" hereinafter) is included.

Also, origins of the functionally equivalent variant and homologous polypeptide are not limited to specific organism species. In addition, they are not limited to natural polypeptides, with the proviso that they come under either the functionally equivalent variant or the homologous polypeptide, and a polypeptide artificially modified by means of genetic engineering based on an amino acid sequence representing a conventionally known molecular chaperone protein is also included therein.

In this connection, the aforementioned "identity" in this description means the value Identity obtained using the parameters arranged as default by NEEDLE program (*J. Mol. Biol.,* 1970; 48: 443-453) retrieval. The aforementioned parameters are as follows.
Gap penalty=10
Extend penalty=0.5
Matrix=EDNAFULL Preferred as the molecular chaperone protein are proteins represented by SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27 (human HSPA1A; RefSeq accession number NP_005336, human HSPH1; RefSeq accession number NP_006635, human HSPCA; RefSeq accession number NP_005339, human HSPD1; RefSeq accession number NP_955472, human DNAJA1; RefSeq accession number NP_001530, human HSPB1; RefSeq accession number NP_001531, human HSPE1; RefSeq accession number NP_002148, human HSPA4; RefSeq accession number NP_002145, human HSP90B1; RefSeq accession number NP_003290, human CCT6B; RefSeq accession number NP_006575, human TCP1; RefSeq accession number NP_110379, human HSPA14; RefSeq accession number NP_057383, human HSPA9B; RefSeq accession number NP_005338, human STCH; RefSeq accession number NP_008879, human HYOU1; RefSeq accession number NP_006380, human HSPB5; RefSeq accession number NP_001876, human HSPB2; RefSeq accession number NP_001532, human DNAJA2; RefSeq accession number NP_005871, human DNAJB1; RefSeq accession number NP_006136, human DNAJB2; RefSeq accession number NP_006727, human HCG3; RefSeq accession number NP_001001394, human DNAJB11; RefSeq accession number NP_057390, human DNAJC11; RefSeq accession number NP_060668, human DNAJC7; RefSeq accession number NP_003306, human DNAJC6; RefSeq accession number NP_055602), and a polypeptide which comprises an amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27 wherein 1 to 10 (preferably 1 to 7, more preferably 1 to 5, further preferably 1 to 3) amino acids thereof are deleted, substituted and/or inserted and also binds to a protein by recognizing a change in the tertiary structure of the protein, or a polypeptide which comprises an amino acid sequence having 90% or more (preferably 95% or more, more preferably 98% or more) of identity with the amino acid sequence represented by SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27 and also binds to a protein by recognizing a change in the tertiary structure of the protein.

The term "binds to a protein by recognizing a change in the tertiary structure of the protein" means that the molecular chaperone binds to a protein by responding to a change in the tertiary structure of the protein caused by its binding with an agent to be tested, or the molecular chaperone once bound to a protein of unchanged state is separated by responding to a change in the tertiary structure of the protein caused by its binding with an agent to be tested. Whether or not the molecular chaperone "binds" by responding to a change in the tertiary structure of the protein can be verified in the same manner as the method for "detecting a protein which binds to molecular chaperone protein" of the identification method of the present invention. Particularly, regarding the functionally equivalent variant and homologous polypeptide of a polypeptide consisting of an amino acid sequence represented by SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18. SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27, to "bind to a protein by recognizing a change in the tertiary structure of the protein" is verified, by responding to a change in the tertiary structure of the ATP5B protein caused by its binding to biguanide (agent to be tested), based on the separation of the molecular chaperone protein once bound to the ATP5B protein of unchanged state by responding to a change in the tertiary structure of the ATP5B protein caused by its binding to biguanide. Alternatively, it is verified by the binding of the molecular chaperone to a protein by responding to a change in the tertiary structure of the TARDBP protein caused by its binding to thalidomide (agent to be tested). These verifications are carried out under the conditions of Example 4 or Example 8, using a functionally equivalent variant or homologous polypeptide to be examined instead of the molecular chaperone protein used in Example 4 or Example 8.

In the identification method of the present invention, among the molecular chaperone proteins, use of the proteins represented by SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18. SEQ ID NO:19, SEQ ID NO:20, SEQ ID NO:21, SEQ ID NO:22, SEQ ID NO:23, SEQ ID NO:24, SEQ ID NO:25, SEQ ID NO:26 and/or SEQ ID NO:27 is particularly desirable. Since these proteins belong to the aforementioned respective families of different chaperones (Hsp90, Hsp70, Hsp60, Hsp40, Hsp27, Hsp104 and GRP78), it is expected that each of them has a property characteristic to each family of the molecular chaperone protein.

<Production Method of Molecular Chaperone Protein>

In the identification method of the present invention, a molecular chaperone protein can be easily produced and obtained by a general genetic engineering and/or biochemical means using a polynucleotide coding for the molecular chaperone protein. Said polynucleotide can be easily produced and obtained by a general genetic engineering technique based on the sequence information disclosed in this description or conventionally known sequence information.

For example, it can be obtained in the following manner, but it can be obtained not only by this method but also by conventionally known operations ("Molecular Cloning" [Sambrook, J. et al., Cold Spring Harbor Laboratory Press, 1989, and the like]). For example, (1) a method which uses PCR, (2) a method which uses a usual genetic engineering technique (namely a method in which a transformant containing the desired polypeptide is selected from the transformants transformed with a cDNA library), or (3) a chemical synthesis method can be cited. Respective production methods can be carried out in the same manner as described in WO 01/34785.

In the method which uses PCR, a polynucleotide coding for a molecular chaperone protein can be produced, for example, by the procedure described in the "Mode for Carrying Out the Invention" 1) Production method of protein gene, a) First production method, of the aforementioned patent reference. For example, mRNA is extracted from human liver, brain, mammary gland or the like tissue. Next, a first strand cDNA is synthesized by carrying out a reverse transferase reaction of this mRNA in the presence of random primers or oligo(dT) primers. A polynucleotide coding for the molecular chaperone protein or a part thereof can be obtained by subjecting the thus obtained first strand cDNA to a polymerase chain reaction (PCR) using two primers interposing a partial region of the gene of interest. More illustratively, a polynucleotide coding for a molecular chaperone protein can be produced by the method described in Example 1.

In the method which uses a usual genetic engineering technique, a polynucleotide coding for a molecular chaperone protein can be produced, for example, by the procedure described in the "Mode for Carrying Out the Invention" 1) Production method of protein gene, b) Second production method, of the aforementioned patent reference.

In the method which uses a chemical synthesis method, a polynucleotide coding for a molecular chaperone protein can be produced, for example, by the procedure described in the "Mode for Carrying Out the Invention" 1) Production method of protein gene, c) Third production method, d) Fourth production method, of the aforementioned patent reference. Illustratively, it can be produced by liquid phase and solid phase peptide synthesis methods. The synthesis may be carried out by successively binding amino acids one by one, or by synthesizing a polypeptide fragment consisting of several amino acids and then binding it. The polypeptide of the present invention obtained by these means can be purified in accordance with various conventionally known methods.

Mutation of the sequence sometimes occurs by a natural mutation, but can also be prepare by carrying out artificial modification. The present invention does not care about the cause and means of the mutation. Regarding the artificial means for preparing the aforementioned mutants, in addition to the gene engineering techniques such as the base-specific substitution method (*Methods in Enzymology*, (1987) 154, 350, 367-382) of a polynucleotide coding for the aforementioned polypeptide, phosphotriester method, phospho-amidide method and the like chemical synthesis means (*Science*, 150, 178, 1968) can for example be cited. It is possible to obtain a polynucleotide which accompanies the desired base substitution by their combination. Alternatively, it is possible to generate substitution of a non-specific base in the polynucleotide molecule by repeating the operation of PCR or adding manganese ion or the like to its reaction liquid.

The molecular chaperone protein can be expressed in vitro or in a cell to be tested, by connecting the molecular chaperone protein-encoding polynucleotide obtained as described in the above to the downstream of an appropriate promoter by the method described in "Molecular Cloning, Sambrook, J. et al., Cold Spring Harbor Laboratory Press, 1989" or the like.

Illustratively, by adding a polynucleotide containing a specific promoter sequence to the upstream of the initiation codon of the polynucleotide obtained as described in the above, and using this as the template, expression of the molecular chaperone protein by transcription and translation of the gene in a cell-free system can be carried out. Alternatively, when the molecular chaperone protein-encoding polynucleotide is integrated into an appropriate vector plasmid and transform a host cell by the plasmid, expression of said polypeptide becomes possible. Still alternatively, a cell in which such a construction is integrated into chromosomal DNA may be prepared and used. More illustratively, when a fragment containing the isolated polynucleotide is again integrated into an appropriate vector plasmid, it can transform host cells of eukaryote and prokaryote. In addition, when an appropriate promoter and a sequence concerned in the gene expression are transferred into these vectors, it becomes possible to effect expression of the molecular chaperone protein in respective host cells. The host cell is not particularly limited, and it may be any cell which can realize expression of the molecular chaperone protein in an amount sufficient for the purpose of applying to the method of the present invention. As the host cell, for example, a monkey cell COS cell (Gluzman, Y. (1981) *Cell*, 23, 175-182), a dehydrofolate reductase deficient strain of Chinese hamster ovary cell (CHO) (Urlaub, G. and Chasin, L. A. (1980) *Proc. Natl. Acad. Sci. USA*, 77, 4216-4220), human fetal kidney derived HEK293 cell and 293-EBNA cell in which EBNA-1 gene of Epstein Barr virus is transferred into the same cell (mfd. by Invitrogen), and the like can be cited.

The method for expressing a gene by transforming a host cell can be carried out, for example, by the method described in the recombinant protein production method of the "Mode for Carrying Out the Invention" 2) of the aforementioned patent reference. The expression vector to be used in the production of a molecular chaperone expression cell (expression vector for molecular chaperone expression) is not particularly limited, with the proviso that it contains the desired polynucleotide. For example, an expression vector obtained by inserting the polynucleotide of interest into a conventionally known expression vector optionally selected in response to the host cell to be used can be cited. As the conventionally known expression vector, for example, pSV2dhfr having SV40 early promoter (Subramani, S. et al. (1981) *Mol. Cell. Biol.*, 1, 854-864), pEF-BOS having human elongation factor promoter (Mizushima, S, and Nagata, S. (1990) *Nucleic Acids Res.*, 18, 5322), pCEP4 having cytomegalovirus promoter (Invitrogen), pME18S (Maruyama, K. and Takebe, Y. (1990) *Med. Immunol.*, 20, 27-32), pCDM8 (Seed, B. (1987) *Nature*, 329, 840-842) and the like can be cited. The molecular chaperone protein can be obtained, for example, by transforming a desired host cell with the aforementioned expression vector, and effecting expression of the aforementioned polypeptide in said cell. More illustratively, by integrating a desired polynucleotide into a bacterial expression vector, a desired molecular chaperone protein can be produced in bacterial cells in a large amount. Also, the molecular chaperone protein can also be produced in a large amount using yeast, an insect cell or the like. In addition, a desired molecular chaperone protein can be produced in vitro by a conventionally known method using the aforementioned polynucleotide linked to the downstream of a certain promoter. More illustratively, a desired molecular chaperone protein can be produced in vitro by carrying out transcription and translation reactions in vitro using, as the template, the aforementioned polynucleotide linked to the downstream of the aforementioned promoter.

By culturing the aforementioned cell, the molecular chaperone protein produced in the cells can be detected, determined and further purified. For example, it is possible to detect and purify said protein by western blotting or immunoprecipitation using an antibody which binds to the molecular chaperone protein. Alternatively, by expressing said protein as a fusion protein with an appropriate tag protein such as glutathione-S-transferase (GST), protein A, β-galactosidase, maltose-binding protein (MBP) or the like, said protein can be detected by western blotting or immunoprecipitation using an antibody specific for such a tag protein. In addition, the aforementioned protein can be purified making use of these tag proteins. More illustratively, the aforementioned protein can be purified making use of a tag protein in the following manner.

In the method of the present invention, a polynucleotide coding for a molecular chaperone protein (e.g., a polypeptide represented by SEQ ID NO:3, 4, 5, 6, 7, 8, 9, 10, 11, 12, 13, 14, 15, 16, 17, 18, 19, 20, 21, 22, 23, 24, 25, 26 or 27) is integrated for example into a vector by which GST tag or His tag is added to the expressed protein of interest, more illustratively the pGEX-6P1 (mfd. by Amersham) described in Example 1 or a commercially available pET-28a (Novagen) for example, and transferred into a bacterium, and the molecular chaperone protein can thereby expressed as a GST fusion type protein in the case of the former, and as a His fusion type protein in the case of the latter. Said fusion type protein can be purified from a protein extract derived from the bacterial cell expressing the protein, making use of the properties of the GST or His tag. For example, each of the chaperone expression plasmids prepared in Example 1 using pGEX-6P1 is designed in such a manner that the GST tag is added to the N-terminal of the molecular chaperone protein. By this, the desired molecular chaperone protein can be purified from a cell in which said protein was expressed, making use of the GST tag. More illustratively, the molecular chaperone protein fused with GST tag can be isolated from a disrupted cell extract by binding to glutathione Sepharose beads (Glutathione Sepharose 4B; Amersham) and centrifuging it, in accordance with the conventionally known GST pull-down method (N. Matsu et al., *Jikken Kogaku* (Experimental Engineering), Vol. 13, No. 6, page 528, 1994). On the other hand, regarding the purification of a desired molecular chaperone protein from a cell expressing said protein making use of His tag, the molecular chaperone protein fused with His tag can be isolated from a disrupted cell extract by binding to $Ni^{2+}$-NTA-Agarose (mfd. by Funakoshi) and centrifuging it, in accordance with the conventionally known method (Nakahara et al., *Jikken Igaku Bessatsu Tanpakushitsu no bunshikan sogo sayo jikken-ho* (Experimental Medicine, supplement, Experimental methods of the intermolecular interaction of protein), page 32, 1996).

Alternatively, as occasion demands, the molecular chaperone protein can also be purified by a method which does not use a tag protein, for example by various separation operations making use of its physical properties and chemical properties. Illustratively, application of ultrafiltration, centrifugation, gel filtration, adsorption chromatography, ion exchange chromatography, affinity chromatography and high performance liquid chromatography can be exemplified.

<Agent to be Tested>

Though not particularly limited, examples of the agent to be tested include commercially available compounds (including peptides), various conventionally known compounds (including peptides) registered in chemical files, a group of compounds obtained by the combinatorial chemistry techniques (N. Terrett et al., Drug Discov. Today, 4(1): 41, 1999), microbial culture supernatants, natural components derived from plants and marine organisms, animal tissue extracts (including polynucleotides and peptides), or those which are chemically or biologically modified compounds thereof and have distinct pharmacological actions. Not only the actions desirable for medical treatments but also the actions toxic for the living bodies are included in the pharmacological actions. As compounds considered to be useful in the application of the method of the present invention in comparison with the conventional methods, (1) compounds to which modifications can hardly be applied due to their chemical structures, (2) compounds in which the aforementioned pharmacological actions are lost, or considered to be lost, by modifications, (3) compounds having unidentified chemical structures which produce pharmacological actions by their mixing with degradation or metabolic products or other contaminants, (4) compounds (including natural substances) whose available amounts are limited due to difficulties in performing synthesis and purification or obtaining their raw materials, and the like can be exemplified.

<Cell Extract>

A liquid obtained by extracting protein from a primary target tissue for use in inducing pharmacological action possessed by the agent to be tested, or from a cultured cell keeping most properties of said tissue, can be used as the cell extract to be used in the method of the present invention. Regarding the method for extracting protein from a cell, it is desirable to use a preparation method in response to the purpose. Illustratively, in accordance with conventionally known protein extraction methods, a substance fitted to the purpose is selected from SDS, Triton-X, or CHAPS, CHAPSO and the like various surfactants, the aforementioned cell is disrupted and centrifuged using a buffer containing the substance, and then the supernatant is separated and recovered to be used as the cell extract of the method of the present invention. More illustratively, it is desirable that inhibitors of various living body-derived proteolytic enzymes, such as PMSF (phenylmethyl sulfonylfluoride), EGTA (ethylene glycol-bis($\beta$-aminoethylether)-N,N,N',N'-tetraacetic acid) and the like, are contained in the buffer to be used in the disruption, and it is desirable to store it under a condition of $-80°$ C. or lower which can stably maintain the frozen protein until its application to the method of the present invention.

<Step of Detecting a Protein which Binds to Molecular Chaperone Protein>

It is considered that each molecular chaperone protein responds to a large number of substrate proteins per molecule. However, it is considered that the substrate specificity varies depending on their kinds. Thus, in order to truly inclusively screen targets of compounds having various structures, it is desirable to arrange molecular chaperone proteins belonging to a large variety of different families and use simultaneously as the probe. More preferably, as shown in Example 2(3), 3, 4 and 8 of the present invention, it is desirable to arrange two or more molecular chaperone proteins derived from different chaperone families and use them simultaneously.

Also, in the case of a biochemical test system, when the protein to be used as the probe (molecular chaperone protein in the case of this present invention) is present in large excess in comparison with the protein to be used as the substrate, substrate specificity of the probe is thinned, so that it can be expected that even a protein other than the original protein is recognized by the prove when it is a molecule analogous to said substrate. Accordingly, like the case of the in vitro pull-down method shown in Example 2(2) of the present invention, use of a system in which a large amount of the probe protein can be used in the reaction, in comparison with the cell-derived protein to be used as the substrate, is more desirable in enabling inclusive target screening of compounds.

In addition, it has been reported that many molecular chaperone proteins undergo their actions by forming a polymer in vivo. Accordingly, in carrying out the method of the present invention, it is more desirable to use such a living body sample-derived cell extract and separation conditions that an endogenous chaperone capable of forming a complex with the molecular chaperone protein (probe) is present therein as a mixture, as shown in Examples 2(2) and 4. More illustratively, it is desirable to use a system in which a molecular chaperone protein (probe protein) is allowed to react with a cell extract derived from a cell which contains an endogenous chaperone, like the in vitro pull-down method shown in Example 2(2) of the present invention.

In order to "detect a protein which binds to a molecular chaperone protein", the following operation is carried out. A molecular chaperone protein and a protein which binds to the molecular chaperone protein can be concentrated from a sample cell extract extracted from a cell to which an agent to be tested was added or not added, or a sample cell extract to which an agent to be tested was added or not added, by the conventionally known immunoprecipitation method using an antibody of the molecular chaperone protein or an antibody of a tag fused to the molecular chaperone protein. Alternatively, the molecular chaperone protein and a protein which binds to the molecular chaperone protein can also be concentrated by a conventionally known method which uses affinity beads or affinity column having affinity for the aforementioned tag. As an illustrative method, a GST pull-down method which uses the peptide purified by attaching GST or the like tag can be exemplified.

The protein binding to the molecular chaperone protein is detected by separating the concentrated liquid of molecular chaperone protein and its binding protein obtained in the above by a conventionally known protein separation method. For example, after separating them by polyacrylamide gel electrophoresis, the molecular chaperone protein and the sample cell-derived protein linked to the molecular chaperone protein can be detected by various conventional methods for detecting proteins including already existing protein staining methods such as silver staining, Coomassie Brilliant Blue staining or Negative Gel Staining (Wako Pure Chemical Industries) ("*Idensgi Cloning no Tame no Tanpakushitsu Kozo Kaiseki* (Protein Structure Analysis for Gene Cloning)" Hisashi Hirano Tokyo Kagaku Dojin 1993 p. 37-p. 40). The method to be used in this step of the present invention is not limited to the above method with the proviso that it can detect the protein.

Regarding the proteins detected by the above method, the proteins which bind to the molecular chaperone protein in the case of adding and not adding the agent to be tested are compared. By comparing both cases, a sample cell-derived protein whose binding to the molecular chaperone protein was changed at the time of adding or not adding the agent to be tested (namely, the target protein of the agent to be tested) can be identified. As the method for detecting and comparing a group of sample cell-derived proteins at the time of adding or not adding the agent to be tested, the conventionally known SDS polyacrylamide gel electrophoresis can be exemplified. In that case, more precise comparison can be made when developed by a two dimensional electrophoresis. By comparing the bands developed by the electrophoresis based on the results of the case of the addition of the agent to be tested and the results of the case of the un-addition of the agent to be tested (namely, by comparing whether there is a case in which the quantity of a band increases only at the time of the addition of the agent to be tested or a case in which the quantity of a band increases only at the time of the un-addition of the agent to be tested), a protein whose binding quantity increases only at the time of the addition of the agent to be tested, or whose binding quantity decreases only at the time of the addition of the agent to be tested, can be selected. As the protein whose binding quantity increases only at the time of the addition of the agent to be tested, or whose binding quantity decreases only at the time of the addition of the agent to be tested, it is desirable to select a protein which binds only at the time of the addition of the agent to be tested or does not bind only at the time of the addition of the agent to be tested.

Subsequently, the proteins detected and selected by the above method are identified. The amino acid sequences presenting in their molecules are determined by conventionally known protein purification methods and protein identification methods (Schevchenko et al., *Analytical Chemistry*, vol. 68, p. 850-p. 858, 1996), and based on this amino acid sequence information, a protein whose binding with the molecular chaperone protein changes at the time of the addition or un-addition of the agent to be added (namely a target protein of the agent to be tested) can be identified. Illustratively, the target protein of the agent to be tested can be identified by recovering and purifying the protein from the gel and then determining its amino acid sequence by a mass spectrum method or a conventionally known method. More illustratively, identification of the protein can be carried out by the mass spectrum analysis after digesting the protein of interest separated by the SDS polyacrylamide gel electrophoresis into fragments using trypsin or the like and recovering the thus formed peptide mixture from the gel (Schevchenko et al., *Analytical Chemistry*, vol. 68, p. 850-p. 858, 1996). Alternatively, after eluting the protein of interest from the gel by an electric elution method or the like, or after blotting the protein of interest on the gel on a film of PVDF (polyvinylidene fluoride) or the like, it is made into fragments by an enzyme digestion or a chemical digestion as occasion demands, and, as occasion further demands, the thus obtained peptide fragments are separated by a liquid chromatography, a capillary electrophoresis or the like, and then identification of the protein can be carried out by a mass spectrum analysis or an N-terminal or C-terminal amino acid sequence analysis (H. Hirano, *Proteome Kaiseki—Rixon to Hoho*— (Proteome Analysis—Theory and Method) Tokyo Kagaku Dojin, 2001). In this connection, the identification method to be used in the method of the present invention is not limited to the method described in the above, with the proviso that identification of a group of purified said target proteins can be carried out.

More illustratively, as described in Example 4 and Example 8, identification of the target protein separated by the SDS polyacrylamide gel electrophoresis can be carried out by digesting the protein into fragments using trypsin or the like, recovering the thus formed peptide mixture from the gel and then carrying out a mass spectrum analysis.

It is possible to verify by the conventionally known gene function analyzing techniques that the target protein identified by the method of the present invention is a true target protein which produces pharmacological actions of the agent to be tested. Firstly, illustratively, the presence or absence of direct binding between the agent to be tested and the thus obtained target protein molecule can be examined by the method shown below.

A part or the whole length region of a polypeptide to be examined for whether or not it binds thereto or a part or the whole length region of a polypeptide to be examined to which GST, Flag, His or the like tag was fused is expressed in a cell. The expressed polypeptide to be examined is isolated and purified from said cell by an affinity purification method making use of the affinity for the GST, Flag, His or the like tag, or by an immunoprecipitation method making use of an antibody which responds to said tag. Subsequently, the thus purified a polypeptide is mixed with an agent to be tested, and the complex formed by the binding of said agent to be tested and the polypeptide is isolated. Next, by examining whether or not said agent to be tested is contained in the sample by carrying out a mass spectrometry analysis using a mass spectrometer, after re-separating the compounds by denaturing said complex by an acid, heat or other stimulation and thereby removing the protein alone, the binding of the peptide to be examined with said agent to be tested can be verified. In addition, as another method, whether or not the polypeptide to be examined and said agent to be tested bind to each other can be verified by conventionally known ELISA, western blotting, binding assay and the like methods using, as the probe, a labeled agent to be tested prepared by labeling a part of the molecular structure of the agent to be tested. It is desirable that a radioisotope which does not exert influence upon the binding with the target protein is used as the label of the agent to be tested. Illustratively, for example, a labeled compound can be prepared by substituting an element in the molecule of the agent to be tested with a radioisotope. By using said labeled agent to be tested as the probe, binding of a polypeptide with said agent to be tested can be verified by an ELISA method in which the polypeptide to be examined purified by the aforementioned method is immobilized. Alternatively, after separating the polypeptide to be examined by a conventionally known SDS acrylamide gel electrophoresis and transferring it on a nitrocellulose film, binding of said polypeptide with said agent to be tested can also be verified by a far western method using the aforementioned labeled agent to be tested as the probe. Also after mixing the labeled agent to be tested with the polypeptide to be examined purified by the aforementioned method and washing them by trapping on a filter, binding of said polypeptide with said agent to be tested can be verified by a so-called binding assay in which total amount of the thus formed complex of the compound and peptide is detected by measuring the radiation dose derived from the labeled probe.

Also, whether or not a keyhole structure is present in the target protein identified by the method of the present invention, to which said compound to be tested can bind, by a conventionally known protein tertiary structure predicting technique (*J. Med. Chem.*, Dec. 30, 2004; 47 (27): 6804-11). In addition, expression quantity of the aforementioned target protein can be increased or decreased by various biochemical and/or genetic engineering test methods, such as a conventionally known gene knockout test at the cell level using an RNA interference technique (Tuschl T. et al., Nat. Biotechnol., 2002, 20(5): p. 446-448) and a conventionally known gene over-expression test also at the cell level, as well as the preparation of a gene knockout animal or preparation of a gene over-expressing animal, and since the effect to accelerate or suppress the principal effect or an adverse side effect is found when the principal effect or an adverse side effect is tested under these conditions, it can be confirmed that a target protein encoded by a gene whose expression was changed is the true target protein.

Though the identification method of the present invention can identify the target protein of an agent to be tested which produces pharmacological action of the agent to be tested, the identification method of the present invention is more suited as a method for identifying a target protein which produces a desired pharmacological action (principal effect) among the pharmacological actions of the agent to be tested.

<Screening Tool of the Present Invention and its Use for Screening>

The screening tool of the present invention consists of the following (1) to (3).

(1) A diabetes-treating agent screening tool which has the same medicinal target with biguanide (to be referred to as polypeptide type screening tool of the present invention hereinafter), consisting of a human ATP5B protein (a polypeptide consisting of the amino acid sequence represented by SEQ ID NO:2), an ATP5B functionally equivalent variant (a polypeptide which comprises the amino acid sequence represented by SEQ ID NO:2 or an amino acid sequence of the amino acid sequence represented by SEQ ID NO:2 wherein 1 to 10 (preferably 1 to 7, more preferably 1 to 5, further preferably 1 to 3) amino acids thereof are deleted, substituted and/or inserted, and also binds to biguanide and/or inhibits AMPK activation of biguanide by its over-expression), and an ATP5B homologous protein (a polypeptide which comprises an amino acid sequence having 90% or more, preferably 95% or more, more preferably 98% or more) of identity with the amino acid sequence represented by SEQ ID NO:2, and also binds to biguanide and/or inhibits AMPK activation of biguanide by its over-expression) (to be referred to as polypeptide for tool use hereinafter), (2) a diabetes-treating agent screening tool which has the same medicinal target with biguanide (to be referred to as polynucleotide type screening tool of the present invention hereinafter), consisting of a polynucleotide coding for the polypeptide for tool use (to be referred to as polynucleotide for tool use hereinafter), or (3) a diabetes-treating agent screening tool which has the same medicinal target with biguanide (to be referred to as cell type screening tool of the present invention hereinafter), consisting of a cell which is transformed with the polynucleotide for tool use and thereby expressing the polypeptides for tool use (to be referred to as cell for tool use hereinafter).

In addition, use of
(1) polypeptides for tool use,
(2) polynucleotide for tool use, or
(3) cell for tool use
for the screening of a diabetes-treating agent which has the same medicinal target with biguanide is also included in the present invention.

According to this description, the "screening tool" means a substance for use in the screening (illustratively, the polypeptide, polynucleotide or cell to be used in the screening). The "screening tool of a diabetes-treating agent, which has the same medicinal target with biguanide" is a cell or polypeptide which becomes the object to which a compound to be tested is contacted, or a polynucleotide for obtaining or expressing a polypeptide which becomes the object to which a compound to be tested is contacted, for use in the screening of a diabetes-treating agent which has the same medicinal target with biguanide by the screening method of the present invention.

Origins of the ATP5B functionally equivalent variant and ATP5B homologous polypeptide are not limited to human. With the proviso that it comes under any one of the polypeptides for tool use, not only the mutants of the amino acid sequence represented by SEQ ID NO:2 in human but those derived from all kinds of organisms ranging from a vertebrate to a bacterium are also included therein, and not only natural polypeptides but also polypeptides artificially modified by genetic engineering techniques based on the amino acid sequence represented by SEQ ID NO:2 are included therein. In addition, with the proviso that it binds to biguanide and/or inhibits AMPK activation of biguanide by its over-expression, a polypeptide in which a marker sequence which is described later is contained in the ATP5B functionally equivalent variant or ATP5B homologous polypeptide is also included in the polypeptide for tool use.

In the Example 5(5) and (6) which are described later, it was revealed that amino acid residues concerned in the peripheral structure of site 20, particularly Glu 175 and Asp 295 in the case of human ATP5B, are important for the binding of ATP5B with biguanide. Accordingly, when a mutation is introduced, a modified polypeptide which keeps its activity to bind with biguanide can be easily produced by preserving the amino acid residues concerned in the peripheral structure of site 20, particularly Glu 175 and Asp 295 in the case of human ATP5B, and introducing a mutation into a part other than this.

Human ATP5B polypeptide is more desirable among the polypeptides for tool use, as the polypeptide type screening tool of the present invention, and a polynucleotide coding for human ATP5B polypeptide (particularly preferably the polynucleotide represented by the nucleotide sequence of SEQ ID NO:1) among the polynucleotides for tool use, as the polynucleotide type screening tool of the present invention, and a cell which is transformed with a vector comprising a polynucleotide coding for human ATP5B and is thereby expressing human ATP5B, among the cells for tool use, as the polynucleotide type screening tool of the present invention.

The polynucleotide for tool use can be easily produced and obtained by general genetic engineering techniques based on the sequence information disclosed in this description or conventionally known gene sequence information. As such techniques, as described in the aforementioned <Production method of molecular chaperone protein>, conventionally known operations "Molecular Cloning" [Sambrook, J. et al., Cold Spring Harbor Laboratory Press, 1989, and the like], for example, (1) a method which uses PCR, (2) a method which uses a usual genetic engineering technique (namely a method in which a transformant containing the desired polypeptide is selected from the transformants transformed with a cDNA library), or (3) a chemical synthesis method can be cited. Respective production methods can be carried out in the same manner as described in WO 01/34785.

In the method which uses PCR, a polynucleotide for tool use or a part thereof can be obtained, for example, by extracting mRNA from human skeletal muscle, brain or the like tissue, and using a first strand cDNA in the same manner as described in the aforementioned <Production method of molecular chaperone protein>, by subjecting it to PCR using two primers interposing a partial region of the polynucleotide for tool use. More illustratively, the polynucleotide for tool use can be produced, for example, by the method described in Example 5(1).

Also by the method which uses a usual genetic engineering technique or the method which uses a chemical synthesis method, the polynucleotide for tool use can be produced in the same manner as described in the aforementioned <Production method of molecular chaperone protein>.

In the same manner as described in the aforementioned <Production method of molecular chaperone protein>, the polynucleotide for tool use obtained in the above manner can be expressed in vitro or in a cell to be tested by connecting the polynucleotide for tool use to the downstream of an appropriate promoter by a conventionally known method (e.g., the method described in "Molecular Cloning, Sambrook, J. et al., Cold Spring Harbor Laboratory Press, 1989" or the like).

The expression vector to be used in the production of the cell for tool use (expression vector for tool use) is not particularly limited, with the proviso that it comprises the polynucleotide for tool use. For example, an expression vector prepared by inserting the polynucleotide for tool use into a conventionally known expression vector optionally selected in response to the host cell to be used can be cited. The polypeptide for tool use can be obtained, for example, by transforming a desired host cell with the expression vector for tool use, and effecting expression of the polypeptide for tool use in said cell. More illustratively, the polypeptide for tool use can be produced in a large amount in a bacterial cell by integrating the polynucleotide for tool use into a bacterial expression vector. In addition, the polypeptide for tool use can be produced in vitro by a conventionally known method using the polynucleotide for tool use linked to the downstream of a predetermined promoter. More illustratively, as described in Example 5(4), the polypeptide for tool use can be produced in vitro by carrying out transcription and translation reactions in vitro using, as the template, the aforementioned polynucleotide for tool use linked to the downstream of a promoter and using the TNT system (mfd. by Promega).

The cell for tool use is not particularly limited with the proviso that it is transformed with the expression vector for tool use and comprises the polynucleotide for tool use, so that it may be a cell in which the polynucleotide for tool use is integrated into the chromosome of a host cell, or a cell which comprises the polynucleotide for tool use in the form of an expression vector. As the cell to be used in the transformation, a cell which responds to biguanide is desirable, and more illustratively, HeLa S3 cell, a liver-derived cell or a skeletal muscle-derived cell is desirable. As the cell for tool use, it may contain a polynucleotide comprising a marker sequence which is described later, with the proviso that it comes under the polynucleotide for tool use. As the cell type screening tool according to this description, a cell transformed with the expression vector for tool use is desirable.

The desired transformant cell obtained in the above can be cultured in accordance with a usual method, and the polypeptide for tool use is produced by said culturing. As the medium to be used in said culturing, generally used various media can be optionally selected in response to the employed host cell, and in the case of the aforementioned HeLa S3 cell for example, Dulbecco's modified Eagle's minimum essential medium (DMEM) supplemented with fetal bovine serum (FBS) or the like serum component, and the like can be used.

As occasion demands, the polypeptide for tool use produced by the above manner can be separated or purified by various conventionally known separation operations making use of the physiological properties, biochemical properties and the like of said polypeptide. Also, when a marker sequence (tag protein) is contained in the polypeptide for tool use, it is possible to carry out expression confirmation, purification and the like of said polypeptide making use of the tag protein. Examples of the marker sequence include FLAG epitope, Hexa-Histidine tag, Hemagglutinin tag, myc epitope, glutathione-S-transferase (GST), protein A, β-galactosidase, maltose-binding protein (MBP) and the like.

In addition, it is possible also to obtain the polypeptide for tool use by effecting expression of a fusion polypeptide in which a specific amino acid sequence which can be recognized by enterokinase, factor Xa, thrombin and the like proteases is inserted between a marker sequence and the polypeptide for tool use, purifying it making use of the tag protein, and then digesting and removing the marker sequence moiety by these proteases.

More illustratively, the polypeptide for tool use can be expressed, for example, using a vector by which the GST tag or His tag is added to the protein of interest, more illustratively a commercially available pGEX-6P1 (Amersham) or pET-28a (Novagen) for example, as a GST fusion type protein in the former case or a His fusion type protein in the latter case. Said fusion type proteins can be purified from the protein extracts derived from the bacterial cells which expressed them, in the same manner as described in the aforementioned <Production method of molecular chaperone protein> making use of the properties of the GST tag or His tag.

The "polypeptide which binds to biguanide" according to this description means a polypeptide which binds to a low molecular compound classified into biguanide (metformin, phenformin, buformin or the like), and whether or not the polypeptide "binds" to biguanide can be verified by the following method.

The polypeptides to be examined on whether or not they bind thereto are isolated and purified. Expression of the polypeptides and their isolation and purification can be carried out making use of the aforementioned methods. Subsequently, whether or not they bind to phenformin is verified by the method of Example 5(4). A polypeptide whose binding to phenformin at its adding concentration of preferably 10 μM or less, more preferably 1.0 μM or less, further preferably 0.1 μM or less, can be confirmed under the conditions of said Example is regarded as a polypeptide which binds to biguanide.

In addition, the term "inhibits AMPK activation of biguanide by its over-expression" means that activation of AMPK in a cell when stimulated with biguanide under such a condition that a certain polypeptide is present in the cell in an excess amount than usual, namely degree of phosphorylation, is reduced in comparison with the cells of usual state. Whether or not it "inhibits AMPK activation" can be verified by the method of Example 5(7). When increase in the phosphorylation of AMPK by phenformin stimulation in a cell over-expressing the polypeptide to be examined is reduced by a factor of 50%, preferably 79%, further preferably 90%, in comparison with the control (a cell not over-expressing the polypeptide to be examined) under the conditions of Example 5(7), it is judged that the polypeptide to be examined is a polypeptide which inhibits AMPK activation of biguanide by its over-expression.

<Screening Method of the Present Invention>

The inventors have found that when human ATP5B (SEQ ID NO:2) as one of the polypeptides for tool use is over-expressed in HeLa S3 cell, AMPK activation in said cell by treatment with phenformin, metformin or the like biguanide is inhibited (Example 5(7)). This means that activation ability of AMPK contributing to the drug effect of biguanide changes by the change of the amount of ATP5B protein which exists in the cell, and shows that ATP5B is evidently positioned at the upstream of AMPK in terms of the intracellular signal of biguanide. In addition, the inventors have found that ATP5B biochemically binds to phenformin as a species of biguanide (Example 5(4)). Based on these findings, it can be concluded that ATP5B is a true target protein which binds to biguanide and contributes to the drug effect (principal effect) of said compound. In accordance with said findings, the inventors have revealed that a compound capable of showing a drug effect similar to the diabetes-treating effect of biguanide can be newly obtained by carrying out screening of a low molecular compound which activates AMPK, and thereby have accomplished a screening method of an agent for treating diabetes.

The following methods are included in the screening method of the present invention.

<I> Binding Assay Screening Method

A method for screening for an agent for treating diabetes, which comprises

[1] a step of allowing a polypeptide for tool use or a cell for tool use and a substance to be tested to be in contact with each other, and

[2] a step of analyzing binding of said polypeptide with the substance to be tested.

<II> Competitive Inhibition Screening Method

The screening method described in <I>, wherein the step [1] is a step of allowing them to be in contact with each other in the coexistence of biguanide.

The "screening" according to this description both of the screening of a substance having the activity of interest from a large number of substances to be tested and the detection of whether or not the substance is a substance having the property of interest.

<Binding Assay Screening Method which Uses a Polypeptide for Tool Use>

Included in the screening method of the present invention, which comprises a step of allowing a polypeptide for tool use and a substance to be tested to be in contact with each other, is a method in which a purified polypeptide for tool use and a substance to be tested are allowed to be in contact with each other by mixing them (a step of contacting), a substance which directly binds to said polypeptide and acts thereon (namely an agent for treating diabetes) is analyzed by identifying, by a mass spectrometry, the compounds separated by denaturing a complex formed by the binding of said substance to be tested and polypeptide after its isolation (a step of analyzing the binding), and then a substance which binds to the polypeptide for tool use (namely an agent for treating diabetes) is selected. Such a method can be carried out by an affinity selection-mass spectrometry (AS-MS method; cf. *Pharmacia* (Pharmaceutical Society of Japan) Vol. 41 No. 6 p. 564 2005, *J. Protein Chem.* 1997, 16, 5, 505-511, *J. Comb. Chem.* 1999, 1, 82-90, *Anal. Biochem.* 324 (2004) 241-249, *J. Biomol. Screening* 9 (6); 2004 498-505). In the screening method of the present invention, these steps can be carried out illustratively, for example in the following manner. A polypeptide for tool use is expressed in a cell. The expressed said polypeptide is isolated and purified from said cell by an affinity purification method making use of its affinity for GST, Flag, His or the like tag, or an immunoprecipitation method or the like using an antibody which responds to the polypeptide for tool use (e.g., an anti-ATP5B antibody or a tag antibody). Subsequently, the purified said polypeptide are mixed to effect their contact, and then the substance which does not bind to said polypeptide is removed by a low molecular compound-adsorbing resin or the like. A complex of the remaining protein and substance to be tested is isolated, and then the low molecular substance in the complex is separated by denaturing said complex by an acid, heat or other stimulation, and the remained protein alone is removed. A substance which binds to the polypeptide for tool use is selected by identifying the substance contained in the same sample through the mass spectrometry analysis using a mass spectrometer. When concentration of the polypeptide for tool use is 1 µM or 10 µM in the method described in the above, a substance having preferably 5% or more, more preferably 10% or more, further preferably 50% or more, as the total amount of recovered said substances to be tested, under a condition of 1 µM as the adding concentration of the substances to be tested, in comparison with the control which does not go through the step of adhering and removing the substances to be tested, is selected as the substance which binds to the polypeptide for tool use.

In addition, a method in which a substance which binds to the polypeptide for tool use is selected making use of a conventionally known ELISA method, far western method, binding assay method or the like method, by applying a specified label to a group of substances to be tested is also included in the method of the present invention. As an illustrative example of such a case, the method of Example 5(4) can be cited. In such a method, a substance to be tested which can detect binding with the polypeptide for tool use at a concentration of preferably 10 µM or less, more preferably 1 µM or less, further preferably 0.1 µM or less, is selected as the substance which binds to polypeptide for tool use.

<Competitive Inhibition Screening Method which Uses a Polypeptide for Tool Use>

The screening method of the present invention which comprises a step of allowing a polypeptide for tool use and a substance to be tested to be in contact with each other in the coexistence of biguanide can be accomplished by measuring, in the step of detecting binding of the polypeptide for tool use and biguanide by an ELISA method, far western method, a binding assay or the like using a labeled or modified biguanide and said polypeptide, a change in said binding which occurs when a substance to be tested is allowed to be present at the same time.

Illustratively, various experimental means exemplified in the following are used. A polypeptide for tool use is expressed in a cell. The expressed polypeptide for tool use is isolated and purified from said cell by an affinity purification method making use of its affinity for a tag, or an immunoprecipitation method or the like using an antibody which responds to the polypeptide for tool use (e.g., an anti-ATP5B antibody or a tag antibody). Subsequently, the purified polypeptide is mixed a substance to be tested and biguanide, and the thus formed complex is isolated. Next, the substance to be tested and biguanide are again separated by denaturing said complex by an acid, heat or other stimulation, the remained protein alone is removed, and then whether or not the binding of the polypeptide for tool use and biguanide is inhibited by the substance to be tested is examined by examining whether or not a corresponding biguanide compound is contained in the same sample through the mass spectrometry analysis using a mass spectrometer. In addition, as another means, binding of the polypeptide for tool use and biguanide can be verified by a conventionally known ELISA method, far western method, binding assay or the like method using, as the probe, a labeled biguanide prepared by labeling a part of its molecular structure. Illustratively, for example, a labeled compound is prepared by substituting an element in the molecule of biguanide with a radioisotope. Making use of said labeled biguanide as the probe, binding of the purified polypeptide for tool use and biguanide is verified by a said polypeptide-immobilized ELISA method. Alternatively, polypeptides for tool use are separated by the conventionally known SDS acrylamide gel electrophoresis and transferred on a nitrocellulose film, and then binding of said polypeptide with biguanide is also verified by the far western method which uses the aforementioned labeled biguanide as the probe. Also alternatively, binding of a polypeptide for tool use and biguanide is verified by a so-called binding assay in which labeled biguanide and purified polypeptide for tool use are mixed and washed by trapping on a filter, and then total amount of the formed complex of the compound and peptide is detected by measuring the radiation dose derived from the labeled probe. The labeling of biguanide is not limited to a radioisotope, and it is possible to attain the purpose by modifying a part of its molecular structure within such a range that it does not exert influences upon its pharmacological activities. For example, it can be labeled by modifying through the biotinylation of a part of the molecular structure of phenformin, metformin or buformin. Also in this case, binding of the polypeptide for tool use and biguanide is verified by the ELISA or far western method in the same manner as described in the above making use of biotin and avidin and by the use of a labeled avidin antibody or the like. Preferably, binding of the polypeptide for tool use and biguanide is verified by the method of Example 5(4).

In the aforementioned step of verifying binding of the polypeptide for tool use and biguanide, whether or not the binding of said polypeptide and biguanide is inhibited is examined in the presence a substance to be tested together with biguanide. When the concentration of biguanide is 10 μM, a substance having an IC50 value of preferably 10 μM or less, more preferably a substance of 1 μM or less, further preferably a substance to be tested of 0.1 μM or less, is selected as an agent for treating diabetes. When binding of the polypeptide for tool use and biguanide is obstructed by the presence of a specific substance to be tested, it can be judged tat this phenomenon is a result of the competitive inhibition of the binding of biguanide and said polypeptide caused by the binding of said substance to be tested to the biguanide binding site in the molecule of the polypeptide for tool use. Regarding the verification that it is evidently competitive binding inhibition by the substance to be tested, it can be verified by examining stepwise obstruction of biguanide to be bound to said polypeptide, by carrying out stepwise changing of the ratio of concentrations of the biguanide and substance to be tested to be present at the same time. By the same method, a substance which binds to the polypeptide for tool use in competition with biguanide (namely an agent for treating diabetes) can be selected. More illustratively, a substance which binds to the polypeptide for tool use can be selected for example by the method shown in Example 6 which is described later.

<Binding Assay Screening Method which Uses a Cell for Tool Use>

Included in the screening method of the present invention, which comprises a step of allowing a cell for tool use and a substance to be tested to be in contact with each other, is a method in which a cell for tool use and a substance to be tested are allowed to be in contact with each other by mixing them (a step of contacting), a substance which directly binds to said polypeptide and acts thereon (namely an agent for treating diabetes) is analyzed by identifying, by a mass spectrometry, the compounds separated by denaturing a complex formed by the binding of said substance to be tested and polypeptide after its isolation (a step of analyzing the binding), and then a substance which binds to the polypeptide for tool use (namely an agent for treating diabetes) is selected. As the method for analyzing the binding, the aforementioned AS-MS method and the like can be used. Illustratively, it can be carried out for example in the following manner.

Firstly, a cell for tool use in which a polypeptide for tool use is expressed by transforming a cell with a vector comprising the polypeptide for tool use is allowed to be in contact with a substance to be tested. A complex of the polypeptide for tool use and the substance to be tested binding thereto is concentrated from the aforementioned cell by an affinity purification method making use of its affinity for GST, Flag, His or the like tag, or an immunoprecipitation method or the like using an antibody which responds to the polypeptide for tool use (e.g., an anti-ATP5B antibody or a tag antibody). It is desirable to contain the same substance to be tested used in the above for treating the cell, in the reaction liquid of this concentration step. Substances which do not bind to said polypeptide are removed by a low molecular compound-adsorbing resin or the like, and then the low molecular substance in the complex is separated by denaturing the thus obtained complex of the polypeptide for tool use and the substance to be tested binding thereto with an acid, heat or other stimulation, and the remained protein alone is removed. A substance which binds to the polypeptide for tool use is selected from substances to be tested by identifying the substances contained in the same sample through the mass spectrometry analysis using a mass spectrometer. Illustratively, under a condition of 1 μM in concentration of the test substance to be added, a substance having preferably 5% or more, more preferably 10% or more, further preferably 50% or more, as the total amount of recovered said substances to be tested, in comparison with the control which does not go through the step of adhering and removing the substances to be tested, is selected as the substance which binds to the polypeptide for tool use.

<Competitive Inhibition Screening Method which Uses a Cell for Tool Use>

By allowing a cell for tool use and a substance to be tested to be in contact with each other in the coexistence of biguanide, whether or not the binding of the polypeptide for tool use and biguanide is competitively inhibited by said substance to be tested and the substance to be tested and the polypeptide for tool use are bound with each other can be examined. Illustratively, a complex of the polypeptide of the present invention and the biguanide binding thereto is concentrated from a cell in the coexistence of biguanide, by the same process of the aforementioned <Binding assay screening method which uses a cell for tool use>, Subsequently, binding of the polypeptide for tool use and a substance to be tested is analyzed. Analysis of the binding can be carried out by the same method described in the aforementioned <Competitive inhibition screening method which uses a polypeptide for tool use>. For example, in the case of the use of biguanide modified with a label or the like, it can be carried out by determining binding of the polypeptide for tool use and biguanide using the conventionally known binding assay or the like method. When binding of the polypeptide for tool use and biguanide was obstructed by the presence of a substance to be tested, it can be judged that binding of biguanide and the polypeptide for tool use was competitively inhibited by the substance to be tested, and the polypeptide for tool use and the substance to be tested were bound to each other.

It is desirable that the screening method of the present invention further comprises a step, after analyzing binding of the polypeptide for tool use and a substance to be tested and selecting the substance which binds to the polypeptide for tool use, of verifying activation of AMPK by the selected substance to be tested, and/or a step of verifying its possession of diabetes-treating activity.

The step of verifying activation of AMPK by the selected substance can be carried out for example in the following manner. A cell expressing the polypeptide for tool use (e.g., HeLa S3 cell) is cultured after adding a substance to be tested or a vehicle control thereto. Using a cell lysate prepared by lysing the cultured cells, phosphorylation level (namely activation level) of intracellular AMPK is detected by conventionally known SDS electrophoresis and western blotting which uses an anti-phosphorylation AMPK antibody (e.g., Phospho-AMPK-α(Thr 172) Antibody, mfd. by Daiichi Pure Chemicals). Preferably, activation of AMPK by the selected substance can be verified by the method of Example 5(7). By comparing with the control, a substance which accelerates phosphorylation of AMPK is selected as a substance which activates AMPK. As the substance which accelerates phosphorylation of AMPK, a substance which accelerates phosphorylation of AMPK by a factor of 50%, preferably 70%, more preferably 90% or more, in comparison with the control is selected.

As the step of verifying possession of diabetes-treating activity by the selected substance, a step of carrying out a conventionally known evaluation method, for example a method for analyzing diabetes-treating effect of a selected substance as shown below, can be exemplified.

The presence or absence of the diabetes-treating effect is judged by continuously administering a compound selected by the screening method of the present invention to a diabetes model animal and verifying its hypoglycemic action on demand in accordance with the usual way, or by carrying out verification of hyperglycemia suppressing action after oral glucose tolerance test. Alternatively, its effect to treat type II diabetes is analyzed by measuring insulin resistance of human and using improvement of the value as the index. The insulin resistance in human is measured by mainly two methods. One is to measure blood glucose level and insulin concentration after fasting, and the other is a method so-called glucose tolerance test in which glucose liquid is orally administered and its clearance ratio from the blood circulation is checked. In addition, a euglycemic hyperinsulinemia clamp method can be exemplified as a more accurate method. This method is based on the theory that insulin and glucose in blood are maintained at certain concentrations, and periodically measures total amount of the administered glucose liquid and concentration of insulin used for its metabolism ("*Tonyobyo* (Diabetes)" O. Nakagawa 1999 vol. 42(2): pages 111-113). Possession of diabetes-treating activity by the selected substance can be verified preferably by the method described in Example 7.

Though not particularly limited, examples of the test substance to be used in the screening method of the present invention include commercially available compounds (including peptides), various conventionally known compounds (including peptides) registered in chemical files, a group of compounds obtained by the combinatorial chemistry techniques (N. Terrett et al., Drug Discov. Today, 4(1): 41, 1999), microbial culture supernatants, natural components derived from plants and marine organisms, animal tissue extracts, or compounds (including peptides) prepared by chemically or biologically modifying compounds (including peptides) selected by the screening method of the present invention.

<Pharmaceutical Composition for Diabetes Treatment Use, Method for Treating Diabetes and Use of a Substance for Producing the Pharmaceutical Composition for Diabetes Treatment Use>

A pharmaceutical composition for diabetes treatment use, which comprises a substance obtained by the screening method of the present invention [e.g., DNA, a protein (including antibody or antibody fragment), a peptide or a compound other than that] as the active ingredient, is included in the present invention. Also, a method for treating diabetes, which comprises administering a substance obtained by the screening method of the present invention at an effective dose to an object that requires treatment of diabetes, is included in the present invention. In addition, use of a substance obtained by the screening method of the present invention, for producing the pharmaceutical composition for diabetes treatment use, is included in the present invention.

The active ingredient in the pharmaceutical composition of the present invention can be selected by the screening method of the present invention. As the compound selected by the screening method of the present invention, the 2-[(E)-(1H-1,2,4-triazol-3-ylimino)methyl]phenol and 6-chloro-9H-purine-2-amine described in Examples 6(2) and 7 which are described later can be exemplified. In this connection, verification of the presence of diabetes-treating effect can be carried out by using a conventional method known to those skilled in the art or a modified method thereof (c.f., the aforementioned "step of verifying that the selected substance has diabetes-treating activity").

Pharmaceutical preparations for diabetes treatment use, which comprise a substance obtained by the screening method of the present invention [e.g., DNA, a protein (including antibody or antibody fragment), a peptide or a compound other than that] as the active ingredient, can be prepared as pharmaceutical compositions in response to the type of the aforementioned active ingredient, using pharmacologically acceptable carriers, fillers and/or other additive agents which are generally used in preparing them.

As the administration, oral administration by tablets, pills, capsules, granules, fine subtilaes, powders, solutions for oral use or the like, or parenteral administration by injections for intravenous injection, intramuscular injection, intraarticular injection or the like, suppositories, percutaneous administration preparations, transmucosal administration preparations or the like can be exemplified. Particularly in the case of peptides which are digested in the stomach, intravenous injection or the like parenteral administration is desirable.

In the solid composition for use in the oral administration, one or more active substances can be mixed with at least one inert diluent such as lactose, mannitol, glucose, microcrystalline cellulose, hydroxypropylcellulose, starch, polyvinyl pyrrolidone, aluminum magnesium silicate or the like. In accordance with the usual way, the aforementioned composition may contain other additives than the inert diluent, such as a lubricant, a disintegrating agent, a stabilizing agent, a solubilizing or solubilization assisting agent or the like. As occasion demands, tablets or pills may be coated with a sugar coating or with a film of a gastric or enteric substance or the like.

The liquid composition for oral administration may include emulsions, solutions, suspensions, syrups, elixirs or the like and may contain a generally used inert diluent such as purified water or ethanol. In addition to the inert diluent, the aforementioned composition may contain other additive agent such as a moistening agent, a suspending agent, a sweetener, an aromatic or an antiseptic.

The injections for parenteral administration may include aseptic aqueous or non-aqueous solutions, suspensions or emulsions. The aqueous solutions or suspensions may include distilled water for injection, physiological saline or the like as a diluent. The non-aqueous solutions and suspensions may include propylene glycol, polyethylene glycol, a plant oil (e.g., olive oil), an alcohol (e.g., ethanol), polysorbate 80 or the like as the diluent. The aforementioned composition may further contain a moistening agent, an emulsifying agent, a dispersing agent, a stabilizing agent, a solubilizing or solubilization assisting agent, an antiseptic or the like. The aforementioned compositions can be sterilized by filtration through a bacteria retaining filter, blending of a germicide or irradiation. Alternatively, they may be used by firstly producing sterile solid compositions and dissolving them in sterile water or other sterile medium for injection prior to their use.

The dose can be optionally decided by taking into consideration strength of the activity of the substance obtained by the screening method of the present invention, symptoms, age, sex and the like of each object to be administered.

For example, in the case of oral administration, the dose is generally from about 0.1 to 100 mg, preferably from 0.1 to 50 mg, per day per adult (as 60 kg in body weight). In the case of parenteral administration in the form of injections, it is from 0.01 to 50 mg, preferably from 0.01 to 10 mg.

EXAMPLES

The following describes the present invention in detail based on examples, but the present invention is not restricted by said examples. In this connection, unless otherwise noted, they can be carried out in accordance with the conventionally known methods ("Molecular Cloning" Sambrook, J. et al., Cold Spring Harbor Laboratory Press, 1989, and the like). Also, when commercially available reagents and kits are used, they can be carried out in accordance with the instructions attached to the articles on the market.

Example 1

Construction of Molecular Chaperone Protein (1) Cloning of Molecular Chaperone Gene and Preparation of GST Fusion Molecular Chaperone Protein Expression Plasmid Using oligonucleotides represented by SEQ ID NOs:28 to 77 (even numbers for 5' side, odd numbers for 3' side) as primers (e.g., a primer set for human HSPA1A by SEQ ID NO:28 and SEQ ID NO:29, the same shall apply hereinafter), cDNA sequences coding for the complete length regions of 25 species of chaperone proteins (human HSPA1A, human HSPH1, human HSPCA, human HSPD1, human DNAJA1, human HSPB1, human HSPE1, human HSPA4, human HSP90B1, human CCT6B, human TCP1, human HSPA14, human HSPA9B, human STCH, human HYOU1, human HSPB5, human HSPB2, human DNAJA2, human DNAJB1, human DNAJB2, human HCG3, human DNAJB11, human DNAJC11, human DNAJC7, human DNAJC6) represented by the amino acid sequences of SEQ ID NO:3, 4, 5, 6, 7, 8, 9, 10, 11, 12, 13, 14, 15, 16, 17, 18, 19, 20, 21, 22, 23, 24, 25, 26 or 27 were prepared by carrying out PCR using a DNA polymerase (Pyrobest DNA Polymerase, Takara Shuzo) under conditions of 3 minutes of thermal denaturation reaction at 95° C., subsequent 35 repetition of a cycle consisting of 10 seconds at 98° C., 30 seconds at 60° C. and 1 minute and 30 seconds at 74° C. and final heating at 74° C. for 7 minutes, using respective templates; a human liver-derived cDNA library (Clontech) for HSPH1, HSPE1, HSP90B1, HSPA9B and DNAJC11, a human grain-derived cDNA library (Clontech) for HSPCA, HSPA1A and HSPD1, a HeLa cell-derived cDNA library (Clontech) for DNAJA1 and HSPA4, a human mammary gland-derived cDNA library (Clontech) for HSPB1, a human skeletal muscle-derived cDNA library (Clontech) for TCP1, HSPA14, HYOU1 and HSPB2, and commercially available cDNA samples (Ultimate TM ORF Clones, Invitrogen) for CCT6B, STCH, HSPB5, DNAJA2, DNAJB1, DNAJB2, HCG3, DNAJB11, human DNAJC7 and human DNAJC6. The thereby formed DNA fragments of about 2.58 kbp (HSPH1), 2.2 kbp (HSPCA), 1.93 kbp (HSPA1A), 1.72 kbp (HSPD1), 1.19 kbp (DNAJA1), 0.62 kbp (HSPB1), 0.3 kbp (HSPE1), 2.52 kbp (HSPA4), 2.41 kbp (HSP90B1), 2.04 kbp (HSPA9B), 1.69 kbp (DNAJC11), 1.67 kbp (TCP1), 1.05 kbp (HSPA14), 3.0 kbp (HYOU1), 0.53 kbp (HSPB2), 1.59 kbp (CCT6B), 1.42 kbp (STCH), 0.53 kbp (HSPB5), 1.24 kbp (DNAJA2), 1.02 kbp (DNAJB1), 0.98 kbp (DNAJB2), 0.44 kbp (HCG3), 1.077 kbp (DNAJB11), 1.46 kbp (human DNAJC7) and 2.74 kbp (DNAJC6) were obtained. From the sequences contained in the primers, each of the cDNA samples was designed in such a manner that the following restriction enzyme sites are added to both termini thereof. BglII site and XhoI site are added in the case of the cDNA of HSPH1, and EcoRV site and NotI site in the case of the cDNA of HSPA4, EcoRI site and XhoI site in the case of the cDNA of STCH, HSPB5, DNAJC6 and DNAJC11, BglII site and NotI site in the case of the cDNA of TCP1, and BamHI site and NotI site in the case of the cDNA of DNAJA2. In the case of other cDNA molecules, they were designed such that BglII site and XhoI site are added. In order to insert these cDNA molecules into a GST fusion expression vector pGEX-6P-1 (Amersham Bioscience), each of the cDNA fragments obtained by the aforementioned PCR reaction was respectively digested at the respectively added restriction enzyme sites. 1) In the case of the cDNA digested with BamHI (or BglII) and XhoI, the vector was used by making it into a linear form through its digestion with the restriction enzymes BamHI and XhoI, and 2) in the case of the cDNA digested with restriction enzymes EcoRV and NotI, the vector was used by treating it with the restriction enzymes SmaI and NotI, 3) in the case of the cDNA fragment digested with restriction enzymes EcoRI and XhoI, the vector was used by treating it with the restriction enzymes EcoRI and XhoI, and 4) in the case of the cDNA fragment digested with restriction enzymes BamHI and NotI, the vector was used by treating it with the restriction enzymes BamHI and NotI, respectively. A mixture of each of the restriction enzyme-treated chaperone cDNA fragments and the vector was mixed with a DNA ligase liquid (DNA ligation kit II; Takara Shuzo) and treated at 16° C. for 3 hours, thereby preparing a plasmid in which each chaperone cDNA was inserted into the multi cloning site of pGEX-6P-1. By carrying out determination of nucleotide sequences using the oligonucleotide shown in SEQ ID NO:86 as the primer and using a sequencing kit (Applied Biosystems) and a sequencer (ABI 3700 DNA sequencer, Applied Biosystems), those which are the reported respective nucleotide sequences (RefSeq accession numbers NM_005345, NM_006644, NM_005348, NM 199440, NM_001539, NM_001540, NM_002157, NM_002154, NM_003299, NM_006584, NM 030752, NM_016299, NM_005347, NM_006948, NM_006389, NM_001885, NM_001541, NM_005880, NM_006145, NM_006736, NM_001001394, NM_016306, NM_018198, NM_003315, NM_014787) and into which the coding region of each molecular chaperone cDNA and the GST tag translation frame of pGEX vector were simultaneously inserted were respectively selected.

(2) Purification of GST Fusion Molecular Chaperone Protein

A group of GST fusion expression plasmids obtained in the aforementioned (1) prepared by cloning 25 species of molecular chaperone were respectively transferred into *Escherichia coli* BL 21 (Takara Bio) through its transformation by a heat shock method. After overnight shaking culture using 2.4 ml of a culture liquid, its entire volume was transferred into 400 ml of the culture liquid and cultured at 37° C. for 3 hours on a shaker, and then IPTG (Sigma) was added thereto to a final concentration of 2.5 mM and the shaking culture was further carried out for 3 hours to induce respective GST fusion chaperone proteins (hereinafter, respectively referred to as GST-HSPA1A (ca. 96 kDa), GST-HSPH1 (ca. 123 kDa), GST-HSPCA (ca. 111 kDa), GST-HSPD1 (ca. 87 kDa), GST-DNAJA1 (ca. 71 kDa), GST-HSPB1 (ca. 59 kDa), GST-HSPE1 (ca. 37 kDa), GST-HSPA4 (ca. 120 kDa), GST-HSP90B1 (ca. 118 kDa), GST-HSPA9B (ca. 100 kDa), GST-DNAJC11 (ca. 89 kDa), GST-TCP1 (ca. 86 kDa), GST-HSPA14 (ca. 81 kDa), GST-HYOU1 (ca. 137 kDa), GST-HSPB2 (ca. 46 kDa), GST-CCT6B (ca. 84 kDa), GST-STCH (ca. 78 kDa), GST-HSPB5 (ca. 46 kDa), GST-DNAJA2 (ca. 72 kDa), GST-DNAJB1 (ca. 64 kDa), GST-DNAJB2 (ca. 62 kDa), GST-HCG3 (ca. 43 kDa), GST-DNAJB11 (ca. 67 kDa), GST-DNAJC7 (ca. 81 kDa) and GST-DNAJC6 (ca. 125 kDa)) (parenthesized numbers are respectively expected molecular weights). The cells were recovered, and each GST fusion molecular chaperone protein was purified on glutathione Sepharose beads in accordance with the conventionally known GST pull-down method. As the control, a protein of the GST tag moiety alone (to be referred to as GST protein hereinafter; expected molecular weight about 26 kDa) was expression-induced from the *Escherichia coli* BL 21 transformed with pGEX-6P-1 and purified, in the same manner as described in the above. By carrying out separation by SDS polyacrylamide gel electrophoresis and Coomassie Brilliant Blue staining in accordance with the conventionally known methods, it was confirmed that respective proteins having expected molecular weight were purified.

Example 2

Detection of Estrogen Receptor as the Target Protein of 17-β Estradiol (1) Cloning of Estrogen Receptor Gene and Preparation of V5 Tag Fusion Estrogen Receptor Expression Plasmid A gene cDNA coding for the complete length region of estrogen receptor α (to be referred to as ERα hereinafter) as a species of the steroid hormone receptors shown by a conventionally known data base was cloned using two species of DNA primers (SEQ ID NO:78 and SEQ ID NO:79) designed in accordance with the sequence shown by the RefSeq accession number NM_000125. Illustratively, a DNA fragment of about 1.78 kbp coding for the complete length region of ERα was amplified by carrying out PCR using a primer set of SEQ ID NO:78 and SEQ ID NO:79 and using a HeLa cell-derived cDNA library (Clontech) as the template. The PCR reaction was carried out at 98° C. (1 minute) and subsequent 35 repetition of a cycle consisting of 98° C. (5 seconds), 55° C. (30 seconds) and 72° C. (5 minutes), using a DNA polymerase (Pyrobest DNA Polymerase; Takara Shuzo). The thus obtained DNA fragment was sub-cloned into an expression vector (pcDNA3.1/V5-His-TOPO; Invitrogen) using TOPO TA Cloning System (Invitrogen). The primer represented by SEQ ID NO:79 was designed in such a manner that a vector-derived V5 epitope (derived from the V protein of paramyxovirus SV5, Southern J A, *J. Gen. Virol.* 72, 1551-1557, 1991) and a His 6 tag (lindner P, *BioTechniques* 22, 140-149, 1997), excluding the stop codon, are continued in the same frame of ERα gene triplet on the 3' side after the cloning. Nucleotide sequence of the inserted DNA fragment in the thus obtained plasmid was determined using primers which bind to the T 7 promoter region on the vector (TOPO TA Cloning kit; Invitrogen; SEQ ID NO:89) and a sequencing kit (Applied Biosystems) and a sequencer (ABI 3700 DNA sequencer; Applied Biosystems). As a result, it was confirmed that the cDNA coding for the human ERα shown by the RefSeq accession number NM_000125 is inserted the aforementioned expression vector pcDNA3.1N5-His-TOPO. Hereinafter, this expression plasmid is referred to as pcDNA-ER.

(2) Preparation of Human Estrogen Receptor Expression Cell and Detection of 17-β Estradiol Target Protein by the Identification Method of the Present Invention Using Lipofectamine 2000 reagent (Invitrogen), the aforementioned pcDNA-ER was transiently transferred into COS-7 cell (ATCC) cultured on a 10 cm plate to a 70% confluent state. After 30 hours of culturing and subsequent removal of the medium, the cells were washed with ice-cooled PBS and then lysed by adding 1.0 ml of a buffer A (50 mM Tris-HCl (pH 7.5), 10% glycerol, 120 mM NaCl, 1 mM EDTA, 0.5 mM EGTA, 0.5 mM PMSF, 0.5% NP-40). This cell extract was centrifuged at 1500 rpm for 5 minutes to remove the precipitate, and soluble fraction of the supernatant (hereinafter, ER expression cell extract) was collected. ERα known as a target protein which shows the drug effect of 17-β estradiol (to be referred to as E2 hereinafter) (Green S. & Chambon P. *Trends Genet.* 1988 November; 4(11): p. 309-314) is contained in the soluble fraction of this cell extract. In addition, as a control, a cell extract soluble fraction of untransferred COS-7 cell (hereinafter, control COS-7 cell extract) was prepared in the same manner. Whether or not a target protein, ER, can be actually detected by the identification method of the present invention using a chaperone protein, HSPA4 protein, was examined. A 1 µg portion of GST-HSPA4 protein or GST protein (prepared in the aforementioned Example 1(2)) purified on the glutathione Sepharose beads was mixed with the aforementioned ER expression cell extract or control COS-7 cell extract and shaken at 4° C. for 1 hour under a condition of adding or not adding 10 µM of E2. Thereafter, the protein binding to the GST-HSPA4 or GST protein on the beads was co-precipitated by centrifugation. This was suspended in the aforementioned buffer A' (a buffer prepared by changing NaCl concentration in the buffer A to 100 mM) and again co-precipitated by centrifugation. After repeating this operation 4 times, proteins in the precipitate were separated by SDS polyacrylamide gel electrophoresis in accordance with a conventionally known method, and the amounts of ERα as the target protein of E2 were compared by western blotting using an anti-ERα antibody (MC-20; Santa Cruz). As a result (FIG. 1), when the ER expression cell extract was used, an ERα band of about 70 kDa, which is not detected when the control COS-7 cell extract is used, was detected under the E2 un-addition condition (lane 5). On the other hand, the band of ERα was detected only slightly under the E2-added condition (lane 6). Based on these results, it was proved that detection of the target protein of an agent to be tested can be detected without requiring modification of the compound, by comparing the protein which binds to a molecular chaperone protein at the time of adding or not adding said agent to be tested, actually using the molecular chaperone protein.

(3) Detection of Target Protein of 17-β Estradiol by the Identification Method of the Present Invention In the Example 2(2) described in the above, it was proved that detection of the target protein of an agent to be tested can be detected by comparing the protein which binds to a molecular chaperone protein at the time of adding or not adding said agent to be tested, using the molecular chaperone protein. In the following example, it was confirmed that the identification method of the present invention is useful even when molecular chaperones other than the one used in the Example 2(2) are used.

That is, in this Example (3), whether or not the target protein ER can be detected in reality by the identification method of the present invention in the same manner as in the Example 2(2) was examined using the 25 species of chaperone proteins of Example 1(2). The test was carried out in the same manner as in the Example 2(2), except that a mixture in which the aforementioned 25 species of GST fusion proteins (Example 1(2)) were divided into 3 groups 8 or 9 species in accordance with their molecular weight and mixed in 0.2 µg portions, instead of the use of HSPA4 protein as the chaperone protein, or 1.4 µg of GST protein was used, and that western blotting was carried out using an anti-V5 antibody (Invitrogen)which recognizes the V5 epitope fused to ER, and signal strengths of the thus obtained bands were converted into numerals as measured values of the density per unit area using VersaDoc Imaging System (Bio-Rad). Details of the mixed 8 or 9 species of GST fusion chaperone proteins are 3 groups; a group in which a group of chaperons having relatively high molecular weights, GST-HSPH1, GST-HSPA4, GST-HSPCA, GST-HYOU1, GST-DNAJC6, GST-HSP90B1, GST-HSPA9B and GST-DNAJC11, were mixed, a group in which a group of chaperons having medium degree of molecular weights, GST-HSPA1A, GST-HSPD1, GST-DNAJA1, GST-TCP1, GST-CCT6B, GST-HSPA14, GST-DNAJC7 and GST-STCH, were mixed, and a group in which a group of chaperons having relatively low molecular weights, GST-HSPB1, GST-HSPE1, GST-DNAJA2, GST-DNAJB11, GST-DNAJB1, GST-DNAJB2, GST-HSPB2, GST-HSPB5 and GST-HCG3, were mixed. As a result (Table 1), in each case of the use of the chaperon protein mixture groups, an ERα band of about 70 kDa, which is not detected when the control COS-7 cell extract is used, was detected from the ER expression cell extract, under the E2 un-addition condition, and the band of ERα was detected only slightly under the E2-added condition. The ER(L), ER(M) and ER(H) in the table show the results of using the aforementioned a group of chaperons having relatively low molecular weights, a group of chaperons having medium degree of molecular weights and a group of chaperons having relatively high molecular weights, respectively.

Based on these results, it was confirmed that detection of the target protein of an agent to be tested can be detected by comparing the protein at the time of adding or not adding said agent to be tested, even when a large variety of molecular chaperone proteins are simultaneously used.

The following shows that it was able to identify various target proteins of respective agents by the identification method of the present invention using various molecular chaperones, in Example 3, Example 4 and Example 8. Regarding those which were not described in detail in each Example, tests were carried out in accordance with the aforementioned Example 2. In this connection, signal strengths of the bands obtained by the western blotting were converted into numerals as measured values of the density per unit area using VersaDoc Imaging System (Bio-Rad).

Example 3

Identification Method of the Present Invention Using Various Molecular Chaperones It is known that FKBP 12 is one of the target proteins of FK 506 and FK 1706 (*J. Biol. Chem.* 1993 Nov. 5; 268(31): 22992-22999, *Eur. J. Pharmacol.* 2005 Feb. 10; 509(1): 11-19).

It is known that glucocorticoid receptor (hereinafter GR) as a species of human steroid hormone receptors is a target protein which shows the drug effect of dexamethasone (*J. Clin. Invest.* 1995 June; 95(6): 2435-2441).

It is known that human dehydrofolate reductase (to be referred to as DHFR hereinafter) is a target protein which shows the drug effect of methotrexate (hereinafter MTX) (*J. Med. Chem.* 2000 Oct. 19; 43(21): 3852-3861).

Androgen receptor (hereinafter AR) which is known as the target protein of 5a-dihydrotestosterone (hereinafter DHT) (*J. Steroid Biochem. Mol. Biol.* 1993 December; 46(6): 699-711) is contained in the soluble fraction of a human prostate-derived cell, LNCaP cell (ATCC).

Mineralcorticoid receptor (hereinafter MR) which is known as the target protein of aldosterone (*Science* 1987 Jul. 17; 237(4812): 268-275) is contained in the soluble fraction of a human blood vessel-derived cell, HUVEC (ATCC).

By preparing the following respective cell extract soluble fractions, whether or not the aforementioned target proteins of respective agents which are present in said cell extract soluble fractions can be detected by the identification method of the present invention using respective chaperone protein groups. In this connection, among the agents, FK 506 (JP-B-03-038276) and FK 1706 (European Patent No. 346427) were synthesized, and other agents were used by purchasing from Sigma. Each of the bands of FKBP 12, GR and DHFR was detected by the western blotting using an antibody which recognizes the V tag added to respective target proteins in the same manner as in the aforementioned Example 2(3), and the bands of AR and MR by the western blotting using commercially available antibodies (N-20 and C-19, Santa Cruz).

(a) Cell extract soluble fraction of HeLa S3 cell (ATCC) in which a gene cDNA coding for the complete length region of human FKBP 12 (RefSeq accession number NM_054014) was over-expressed (to be referred to as FKBP 12 expression cell extract hereinafter)/a mixed group of respective proteins of chaperone proteins; GST-HSPH1, GST-HSPA4, GST-HSPCA, GST-HYOU1, GST-DNAJC6, GST-HSP90B1, GST-HSPA9B, GST-HSPA1A and GST-DNAJC11

(b) Cell extract soluble fraction of HeLa S3 cell in which a gene cDNA coding for the complete length region of GR (RefSeq accession number NM_001024094) was over-expressed (to be referred to as GR expression cell extract hereinafter)/a mixed group of respective proteins of chaperone proteins; GST-HSPA1A, GST-HSPH1, GST-HSPCA and GST-HSPA4

(c) Cell extract soluble fraction of HeLa S3 cell in which a gene cDNA coding for the complete length region of DHFR (RefSeq accession number NM_000791) was over-expressed (to be referred to as DHFR expression cell extract hereinafter)/a mixed group of respective proteins of chaperone proteins; GST-HSPD1, GST-DNAJA1, GST-HSPB1 and GST-HSPE1

(d) LNCaP soluble fraction/a mixed group of respective proteins of chaperone proteins; GST-HSPA1A, GST-HSPH1, GST-HSPCA and GST-HSPA4

(e) HUVEC soluble fraction/a mixed group of respective proteins of chaperone proteins; GST-HSPA1A, GST-HSPH1, GST-HSPCA and GST-HSPA4

(f) Cell extract soluble fraction of HeLa cell (hereinafter, control HeLa cell extract; control of the aforementioned (a) to (c))

As a result (Table 1), when the FKBP 12 expression cell extract, GR expression cell extract and DHFR expression cell extract were used, the bands of FKBP 12, GR and DHFR which are not detected when the control HeLa cell extract is used was detected more distinctively under added condition of each agent, in comparison with the un-added condition. In addition, the band of AR was detected more distinctively under the un-added condition of DHT, and the band of MR was detected more distinctively under the added condition of aldosterone. Based on these results, it was confirmed similar to the case of Example 2 that target protein of agents to be tested can be detected by comparing proteins binding to molecular chaperone proteins at the time of adding or not adding said agents to be tested, by using various molecular chaperone proteins.

TABLE 1

| Target proteins | Agents (concentration μM) | Detected amount of target proteins | |
|---|---|---|---|
| | | Not added | Added |
| ER (L) | E2 (100) | 18 | 8 |
| ER (M) | E2 (100) | 14 | 10 |
| ER (H) | E2 (100) | 4 | 3 |
| FKBP 12 | FK 506(100) | 2 | 5 |
| FKBP 12 | FK 1706 (100) | 941 | 2361 |
| GR | Glucocorticoid (100) | 8069 | 9362 |

TABLE 1-continued

| Target proteins | Agents (concentration μM) | Detected amount of target proteins | |
|---|---|---|---|
| | | Not added | Added |
| PPARγ | Pioglitazone (100) | 7248 | 9229 |
| AR | DHT (100) | 11535 | 9408 |
| MR | D-aldosterone (100) | 47 | 53 |
| DHFR | MTX (100) | 3552 | 4856 |

Example 4

Identification of Target Protein of Biguanide Using Molecular Chaperone

Using the aforementioned method shown in Example 2(2), attempt was made to screen the target protein of biguanide whose direct target protein has been unclear in spite of its significant drug effect as an agent for treating diabetes. Firstly, a rat skeletal muscle-derived cell, L 6 cell (ATCC), was suspended in a minimum essential medium (αMEM, Invitrogen) containing 10% fetal calf serum (FCS) and cultured on a collagen-coated plate of 15 cm in diameter (Asahi Techno Glass) until reaching the confluent state. The resulting cells were washed twice with 15 ml of ice-cooled phosphate buffer (PBS) and then lysed by adding 2.0 ml of the aforementioned buffer A, and the cell extract was collected using a scraper. This cell extract was centrifuged at 1500 rpm for 5 minutes to remove the precipitate, and the supernatant soluble fraction was collected. Phenformin (Sigma) which is a species of biguanide and whose hypoglycemic action has been clinically recognized (UK Prospective Diabetes Study (UKPDS) Group: *Lancet*, 352, 854 (1998)) was added to the soluble fraction of this cell extract to a final concentration of 50 nM, or not added thereto, and under such a condition, the pull-down test was carried out by adding 1 g of the GST-HSPA4 protein purified on the glutathione Sepharose beads in the same manner as in the aforementioned Example 2(2). After 1 hour of shaking at 4° C., the protein binding to the GST-HSPA4 on beads was co-precipitated by centrifugation. In this connection, in order to prevent drop out of the molecular chaperone protein from the beads, the molecular chaperone protein and beads were used by chemically crosslinking them in advance by a conventionally known method. Illustratively, the GST-HSPA4 protein purified on the glutathione Sepharose beads was washed with 0.2M sodium borate solution and then treated at 4° C. for 45 minutes by suspending in 20 mM DMP. After washing this with 0.2 M monoethanolamine solution to stop the reaction, this was washed by adding 20 mM glutathione solution to remove un-crosslinked molecular chaperone protein, and the resulting substance was used as the probe. After co-precipitating the protein binding to the GST-HSPA4, this was suspended in the aforementioned buffer A' to which 50 nM in final concentration of phenformin was added or not added and again co-precipitated by centrifugation. After repeating this operation 4 times, proteins in the precipitate were separated by SDS polyacrylamide gel electrophoresis in accordance with a conventionally known method, and the proteins were detected by a conventionally known silver staining method. As a result, a large protein band of about 60 kDa, in which its amount to bind to the molecular chaperone protein is reduced at the time of adding phenformin in comparison with the case of no addition, was detected. It is considered that said protein is one of the target protein of phenformin, whose tertiary structure is changed by the addition of phenformin. Thus, this band was cut out, the protein was digested into fragments using trypsin, and the thus formed peptide mixture was recovered from the gel to carry out identification of the protein by mass spectrum analysis in accordance with the conventionally known method (Schevchenko et al., Analytical Chemistry, Vol. 68, pages 850 to 858, 1996). As a result, it was revealed that the protein in said band is ATP5B (RefSeq accession number NP 599191).

Example 5

Inspection of the Binding of ATP5B and Biguanide and Biguanide Response of ATP5B (1) Cloning of Human ATP5B Gene and Preparation of Human ATP5B Expression Plasmid Firstly, cloning of human ATP5B gene was carried out. By synthesizing the primers represented by SEQ ID NO:80 and SEQ ID NO:81, and using said primers, an attempt was made to amplify complete length cDNA of human ATP5B from a human skeletal muscle-derived cDNA library (Clontech) by PCR. The PCR reaction was carried out using a DNA polymerase (TAKARA LA Taq; Takara Shuzo), by heating at 94° C. (3 minutes) and then repeating 35 times of a cycle consisting of 94° C. (30 seconds), 58° C. (1.5 minutes) and 72° C. (4 minutes), and PCR was again carried out using the PCR product as the template under the same conditions. As a result of separating the PCR product by an agarose gel electrophoresis, it was confirmed that a DNA fragment of about 1600 base pairs was amplified. Accordingly, the same DNA fragment in the reaction liquid was cloned into an expression vector (pcDNA3.1N5-His-TOPO; Invitrogen) using TOPO TA Cloning System (Invitrogen). The primer used in this case, represented by SEQ ID NO:81, was designed for excluding the stop codon sequence of human ATP5B so that a vector-derived V5 epitope (derived from the V protein of paramyxovirus SVS, Southern J A, *J. Gen. Virol.* 72, 1551-1557, 1991) is continued to the human ATPSB gene triplet by the same frame on the 3' side after the cloning. Nucleotide sequence of the inserted DNA fragment in the thus obtained plasmid was determined using primers which bind to the T7 promoter region on the vector (TOPO TA Cloning kit; Invitrogen; SEQ ID NO:89) and a sequencing kit (Applied Biosystems) and a sequencer (ABI 3700 DNA sequencer; Applied Biosystems). As a result, it was confirmed that it is a clone which comprises the complete length cDNA sequence for human ATPSB shown by SEQ ID NO:1. Hereinafter, this expression plasmid is referred to as pcDNA-ATPSB.

It was inspected by the following test that the ATP5B, which was found by the identification method of the present invention and considered to be a target protein of biguanide, is the true target protein which produces the pharmacological action (principal effect) of biguanide. In this connection, since all of the conventional methods for screening target proteins of compounds use only direct binding of a compound and a protein as the index, a large number of proteins capable of binding to said compound are obtained, but the probability of finding a protein actually concerned in the drug effect of the compound is low in general. Different from the conventional methods, the method of the present invention aims at finding out the target of a compound using a tertiary structural change of a protein to which the compound is bound as the index, so that it can be necessarily expected that the thus found protein is not a simple binding protein of the compound but a protein molecule whose function is greatly changed by said compound.

(2) Cloning of DHFR Gene and Preparation of GST Fusion Type DHFR Expression Plasmid The DHFR described in the aforementioned Example 3 is a protein whose ability to bind to MTX is known (*Proc. Natl. Acad. Sci. USA*, vol. 87, no. 8: pp. 2955-2959, 1990). In order to use in the following example as the tool for detecting biochemical binding of ATP5B and biguanide, complete length cDNA of human DHFR gene (RefSeq accession number NM_000791) was cloned under the same conditions of Example 2(1) using a human lymphocyte cDNA library (Clontech) as the template and using primers of the nucleotide sequences represented by SEQ ID NO:84 and SEQ ID NO:85. After cloning the thus obtained DHFR cDNA fragment of about 560 base pairs into pcDNA3.1/V5-His-TOPO, the DHFR cDNA fragment was cut out making use of the restriction enzyme sites BamHI and XhoI added to both termini of the aforementioned primers. At the same time, a GST fusion protein expression vector pGEX-6P-1 (Amersham) was converted into a straight chain form by digesting it with the restriction enzymes BamHI and XhoI. A mixture of both of them was mixed with a DNA ligase liquid (DNA ligation kit II; Takara Shuzo) and treated at 16° C. for 3 hours, thereby preparing a plasmid in which the DHFR cDNA is inserted into the multi cloning site of pGEX-6P-1 (to be referred to as pGEX-DHFR hereinafter). By carrying out determination of nucleotide sequence in the same manner as in the aforementioned example using the oligonucleotide shown in SEQ ID NO:86 as the primer, a plasmid into which the coding region of DHFR cDNA and the GST tag translation frame of pGEX vector were simultaneously inserted was selected.

(3) Expression and Purification of GST Fusion Type DHFR Protein

The pGEX-DHFR prepared in the Example 5(2) described in the above was transferred into *Escherichia coli* BL 21 through its transformation by a heat shock method. After overnight shaking culture using 2.4 ml of a culture liquid, its entire volume was transferred into 400 ml of the culture liquid and cultured at 37° C. for 3 hours on a shaker, and then IPTG (Sigma) was added thereto to a final concentration of 2.5 mM and the shaking culture was further carried out for 3 hours to induce expression of a GST fusion DHFR protein (to be referred to as GST-DHFR hereinafter). The cells were recovered, and the GST-DHFR was purified on glutathione Sepharose bawds in accordance with the conventionally known GST pull-down method. As the control, a protein of the GST tag moiety alone (to be referred to as GST protein hereinafter) was expression-induced from the *Escherichia coli* BL 21 transformed with pGEX-6P-1 and purified, in the same manner as described in the above. By carrying out separation by SDS polyacrylamide gel electrophoresis and Coomassie Brilliant Blue staining in accordance with the conventionally known methods, it was confirmed that the protein having expected molecular weight (GST-DHFR; 45 kDa, GST protein; 26 kDa) was purified.

(4) Biochemical Binding of Biguanide and ATP5B

Making use of the GST-DHFR protein prepared in the Example 5(3) described in the above, the presence or absence of biochemical binding of biguanide and ATP5B protein was examined. Illustratively, making use of the property of DHFR to bind to methotrexate (MTX), a compound in which methotrexate was fused to a part of the molecular structure of a biguanide species phenformin, (2S)-5-[(3-{[{[amino(imino)methyl]amino}(imino)methyl]amino}propyl)amino]-2-({4-[[(2,4-diaminopteridin-6-yl)methyl](methyl)amino]benzoyl}amino)-5-oxopentanonic acid dihydrochloride (to be referred to as MTX-phenformin hereinafter), was prepared, this compound was fixed to the GST-DHFR purified on glutathione Sepharose beads by binding to its MTX moiety, and the presence or absence of the binding with ATP5B on the protruding phenformin side was verified by the GST pull-down method.

Firstly, the MTX-phenformin was prepared using conventionally known organic synthesis techniques in accordance with the following reaction scheme.

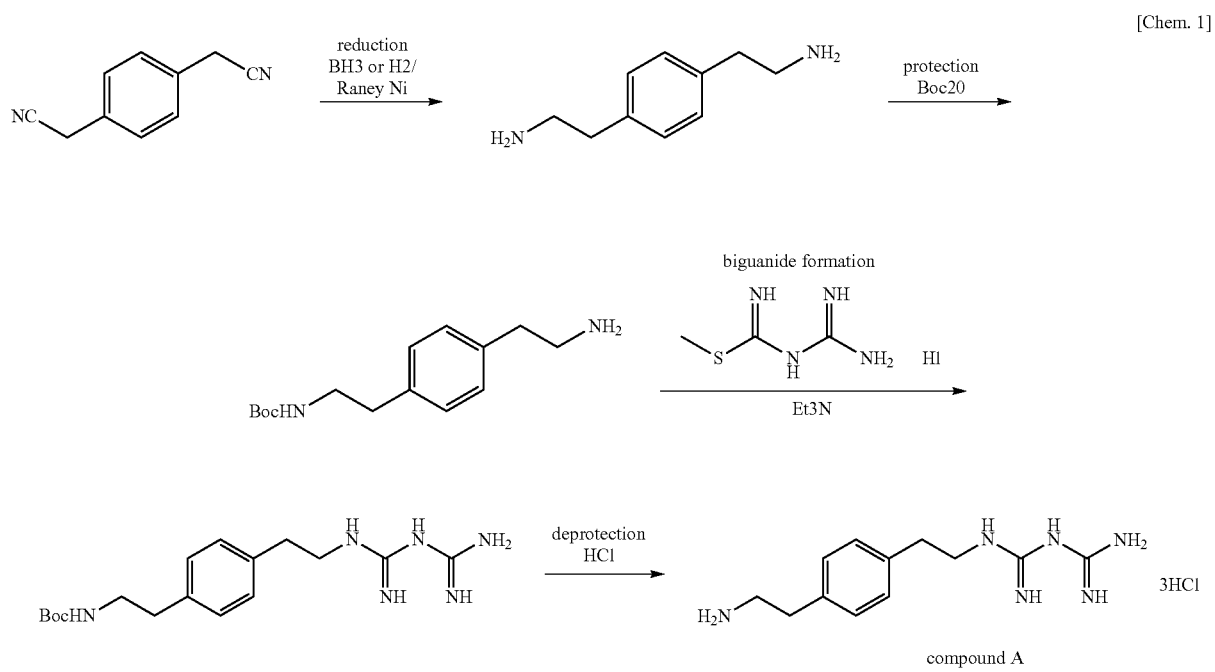

[Chem. 1]

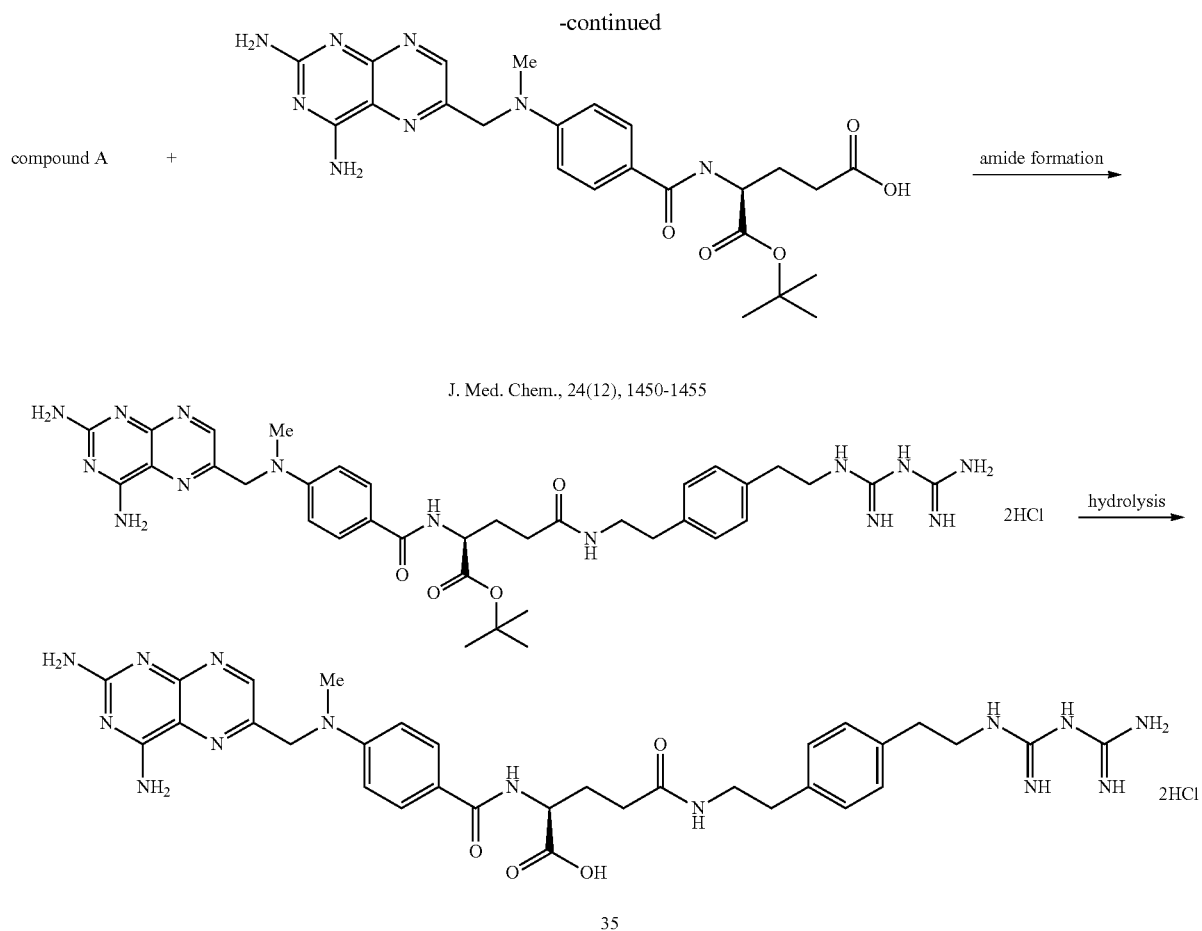

Subsequently, binding of phenformin and ATP5B was examined by the GST pull-down method using the aforementioned purified MTX-phenformin and GST-DHFR protein. Firstly, using 1.0 ng of the aforementioned pcDNA-ATP5B prepared in Example 5(1) as the template, radioisotope-labeled human ATP5B protein was prepared by in vitro transcription and translation by mixing 40 μl of a TNT system (TNT$^R$ Quick Coupled Transcription/Translation System; Promega) and 0.74 MBq of a radioisotope (redivue Pro-mix L-[35S]; Amersham) and in accordance with the protocols attached thereto. A 15 μl portion of this human ATP5B protein preparation liquid and 1 μg for each of the GST protein or GST-DHFR, purified on the glutathione Sepharose beads, were mixed and shaken at 4° C. for 1 hour after adding 0.3 ml of buffer A thereto. Thereafter, the protein binding to the GST protein or GST-DHFR on beads was co-precipitated by centrifugation. After repeating this operation 4 times, proteins in the precipitate were separated by SDS polyacrylamide gel electrophoresis in accordance with a conventionally known method, and the protein bound to the probe was detected by an autoradiography. In all steps of this test, 10 μM in final concentration of the aforementioned MTX-phenformin was added or not added to the buffer, and the results were compared. As a result, as shown in FIG. 1, a band of human ATP5B protein of about 60 kDa synthesized in vitro was detected in the form of binding to the GST-DHFR, only under the condition of adding the MTX-phenformin. This band of human ATP5B protein was not detected when the GST protein was not mixed or under a condition of not adding the MTX-phenformin. By this, it was found that the human ATP5B as one of the polypeptides for tool use directly binds to phenformin.

(5) Prediction of Biguanide Binding Site Existing on the ATP5B Molecule Surface

From the results of the aforementioned Example 5(4), it was confirmed that the human ATP5B protein as one of the polypeptides for tool use directly binds to phenformin. Accordingly, whether or not a keyhole structure to which biguanide can bind is present on the surface of ATP5B protein molecule was examined on a computer based on the data of X-ray crystalline structure analysis of bovine ATP5B. Illustratively, prediction was carried out about a region (site) which is judged that binding of biguanide is possible, on the protein surface of ATP5B as one of the subunits of F1F0-ATP synthase (F1 indicates extramembrane polymer, and F0 indicates intramembrane polymer).

The crystal structure data were obtained from "RCSB Protein Data Bank" as an ID of 1BMF. Heptamer molecules (3 α subunits (A, B and C chains), 3 β subunits (D, E and F chains) and 1 γ subunit (G chain)) of bovine mitochondrial F1-ATP synthase (bovine mitochondrial F1-ATPase) are contained in the 1BMF. ATP5B is β subunit of F1-ATPase as the extracellular region of F1F0-ATP synthase (*Nature*, 1997; 386: 299-302, *Nature*, 1994; 370 (6491): 621-628), and the bovine ATP5B has 99% of identity with human ATP5B in terms of amino acid residues (human ATP5B has 529 residues and bovine ATP5B has 482 residues, and human ATP5B is longer by 46 residues in the N-terminal and by 1 residue in the C-terminal). Among the heptamer molecules of the aforementioned bovine mitochondrial F1-ATP synthase, only the D chain which is bovine ATP5B and one of the β subunits and the A chain and C chain as α subunits adjacent thereto (to be referred to as complex αβα hereinafter) were used in the analysis. Ph4Dock which is a function prepared in the MOE (molecular operating environment) software of Chemical Computing Group Inc. (CCG) was used in the analysis. The Ph4Dock is a function to automatically screen a stable complex structure including its binding position making use of a computer, by merely providing a tertiary structure of a ligand and a receptor (*J. Med. Chem.* 2004 Dec. 30; 47 (27): 6804-11). By providing structural information of metformin and phenformin which are species of biguanide and structural information of the complex αβα making use of this function, sites on the complex αβα, to which these compounds bind, are screened. The results of carrying out screening of the sites on the surface of bovine ATP5B protein molecule, which render possible formation of a stable complex body through the binding of each of metformin and phenformin and the complex αβα, are shown in the following Table 2.

TABLE 2

| Metformin | | Phenformin | |
| --- | --- | --- | --- |
| Site | U_ele- + U_vdw | Site | U_ele- + U_vdw |
| 20 | −957 | 29 | −1156 |
| 20 | −936 | 20 | −1143 |
| 5 | −907 | 29 | −1134 |
| 29 | −898 | 29 | −1119 |
| 5 | −896 | 29 | −1099 |
| 5 | −886 | 29 | −1089 |
| 5 | −877 | 6 | −1084 |
| 5 | −873 | 20 | −1081 |
| 29 | −870 | 29 | −1080 |
| 29 | −861 | 20 | −1075 |
| 3 | −861 | 20 | −1073 |
| 29 | −857 | 29 | −1071 |
| 37 | −852 | 29 | −1066 |
| 6 | −837 | 29 | −1047 |
| 5 | −835 | 20 | −1045 |
| 29 | −834 | 6 | −1034 |
| 48 | −831 | 29 | −1034 |
| 29 | −828 | 6 | −1027 |
| 48 | −827 | 20 | −1026 |
| 48 | −825 | 20 | −1022 |

Table 2 shows the sites to which metformin and phenformin are respectively bound and the energy values on the binding at that time (U_ele+U_vdw). The site in the table indicates binding site, and the binding sites are numbered in order of larger and higher hydrophobic nature for the sake of convenience. The U_ele represents electrostatic interaction energy, and the U_vdw van der Waals energy, respectively, and 20 candidates were arranged and inscribed in order of smaller values of U_ele-+U_vdw. In the molecular mechanics calculation, mmff94s force field was used. In this case, when it is assumed that metformin and phenformin use the same molecule as the medicinal target, the binding sites to which metformin and phenformin bind in common are only the site 20 and site 29. In addition, since the human ATP5B prepared in the aforementioned Example 5(4) by carrying out in vitro transcription and translation bound to phenformin, it can be seen that ATP5B can bind to biguanide, not only under a state of complex but also by itself alone. Thus, when it is limited to a site where ATP5B by itself forms a binding site, the site 20 alone remains as the candidate. Based on the above, it was predicted that metformin and phenformin bind to the site 20 of the complex αβα.

In order to inspect the prediction described in the above, namely direct binding of phenformin to the site 20, it may be effected by finding the most important residue for the binding of phenformin, and experimentally showing that the binding ability disappears when the residue is mutated. Accordingly, when binding of phenformin and site 20 was observed, the presence of 3 patterns of binding mode was predicted as a result. It was found that a cooperative molecular recognition is carried out in each of these binding modes by 3 residues of Glu 125, Glu 241 and Asp 245 (each numeral shows position of the amino acid residue counting from the amino-terminal side of bovine ATP5B molecule) as amino acid residues in the ATP5B molecule. Accordingly, a mutation type human ATP5B was actually prepared in accordance with the method shown in the following example, by respectively substituting Glu 175 and Asp 295 on the human ATP5B molecule, which corresponds to the Glu 125 and Asp 245 among the aforementioned 3 amino acid residues of bovine ATP5B, and its ability to bind to phenformin was examined.

(6) Preparation of Mutation Type Human ATP5B Expression Plasmid and Inspection of Biguanide Binding Ability of Mutation Type Human ATP5B Using the aforementioned expression plasmid pcDNA-ATP5B as the template and using respective sets of primers of the nucleotide sequences represented by SEQ ID NO:87 and SEQ ID NO:81, and SEQ ID NO:80 and SEQ ID NO:88, two DNA fragments of about 530 base pairs of 5'-side and about 1080 base pairs of 3'-side of cDNA having a mutation in which the 175$^{th}$ position of amino acid, Glu, of human ATP5B was replaced by Val were amplified by PCR. All of the PCR reaction, cloning stem and determination of nucleotide sequence were the same as the methods shown in Example 5(1). Using an equivalent mixture of the thus obtained two PCR products as the template, PCR was carried out using the primers represented by SEQ ID NO:80 and SEQ ID NO:81 this time, thereby obtaining a complete length cDNA of about 1600 base pairs coding for a Glu 175 Val mutation type ATP5B. The thus obtained cDNA fragment was cloned into an expression vector (pcDNA3.1/V5-His-TOPO; Invitrogen), and then the nucleotide sequence inserted into the vector was identified using the synthetic primer represented by SEQ ID NO:90 to confirm that the Glu 175 Val mutation was formed in ATP5B. The thus obtained expression plasmid is referred to as pcDNA-ATP5B(E175V) hereinafter. Next, using respective sets of primers of the nucleotide sequences represented by SEQ ID NO:91 and SEQ ID NO:81, and SEQ ID NO:80 and SEQ ID NO:92, a complete length cDNA coding for an Asp 295 Val mutation type ATP5B was obtained by the same method, and an expression vector pcDNA-ATP5B(D295V) was prepared.

Using the pcDNA-ATP5B(E175V) and pcDNA-ATP5B(D295V) prepared in the above, binding ability of the Glu 175 Val or Asp 295 Val mutation type ATP5B protein with phenformin was inspected by the pull-down assay in accordance with the method shown in the aforementioned Example 5(4). As a result, as shown in FIG. 3, it was able to confirm binding of phenformin which can be confirmed by the wild type ATP5B through a band, but it was not able to confirm the binding by the Glu 175 Val or Asp 295 Val mutation type ATP5B because the band disappeared. By this fact, it was proved experimentally that the Glu 175 and Asp 295 of human ATP5B protein are important for the binding with phenformin. In addition, as shown by the results of Example 5(4), it was found that the human ATP5B protein as one of the polypeptides for tool use directly binds to phenformin.

(7) Detection of AMPK Activation Ability of Biguanide in Cell Over-Expressing Human ATP5B or LKB1

Though direct target protein of biguanide has not been found yet, it has been revealed that it activates intracellular AMP activation kinase (AMPK) through its phosphorylation (Zhou G. et al. *J. Clin. Invest.* 2001 October; 108 (8): 1167-74). Since the activity of AMPK is to improve glucose metabolism by accelerating uptake of glucose, it is considered that this activation of AMPK is the main reaction pathway which produces diabetes treating effect which is the dug effect of biguanide. In case that the ATP5B found by the identification method of the present invention is the true target molecule which carries the drug effect (principal effect) of biguanide, the ATP5B protein should be positioned at further upstream of the activation of AMPK in the intracellular signal transduction system which is functioned by biguanide. Accordingly, in order to inspect by an experiment that the ATP5B molecule binding to biguanide is actually positioned at upstream of AMPK activation, whether or not the activation of AMPK by biguanide undergoes an influence under a condition in which ATP5B is excessively expressed in a cell was examined.

For the aforementioned purpose, cloning of a gene cDNA coding for LKB1 which has been shown as one of the enzymes that phosphorylate AMPK (Hardie D G, *J. Cell Sci.* 2004 Nov. 1; 117 (Pt 23): p. 5479-5487) and preparation of an LKB1 expression plasmid were firstly carried out.

In the same manner as the method described in Example 5(1), DNA oligo primers represented by SEQ ID NO:82 and SEQ ID NO:83 were prepared, and a complete length cDNA of human LKB1 gene was cloned by PCR using a human kidney-derived cDNA library (Clontech) as the template. The PCR was carried out under the same conditions of the aforementioned Example 5(1), and the thus amplified DNA fragment of about 1300 base pairs was inserted into the expression vector pcDNA3.1/\75-His-TOPO. As a result of determining nucleotide sequence of the insertion DNA fragment of the accomplished plasmid, it was confirmed that it is a clone consisting of the complete length cDNA sequence of human LKB1 shown by RefSeq accession number NM_000455. Hereinafter, this expression plasmid is referred to as pcDNA-LKB1.

This expression plasmid pcDNA-LKB1 and the pcDNA-ATP5B prepared in the aforementioned Example 5(1) or an empty vector (pcDNA3.1) (Invitrogen) were transferred into HeLa S3 cell. The HeLa S3 cell (ATCC) was cultured in a 6 well culture plate (35 mm in well diameter) until it reached a state of 70% confluent, by adding 2 ml of a minimum essential medium DMEM (Gibco) containing 10% fetal bovine serum (Sigma) to each well of the culture plate. The medium was substituted by 1 ml per well of a serum-free medium OPTI MEM I (Invitrogen), and 3.0 μg/well of each of the empty vector (pcDNA3.1), pcDNA-LKB1 and pcDNA-ATP5B was transiently transferred using Lipofect amine 2000 (Invitrogen). After 12 hours of the culturing, this was substituted by 2 ml/well of DMEM containing 10% of fetal bovine serum from which low molecular substances had been removed by a charcoal treatment, and further cultured for 36 hours. This was further cultured for 1 hour (1 hr) under a condition of adding phenformin (Sigma) to a final concentration of 1 mM or the solvent (DMSO) alone. The medium was discarded, the cells were washed with a phosphate buffer (to be referred to as PBS hereinafter, and then the cells were lysed by adding 0.15 ml of the aforementioned buffer A (however, the NaCl concentration was 150 mM, and various phosphatase inhibitors; 2 mM $Na_3VO_4$, 10 mM NaF, 25 mM β-glycerophosphate, 0.2 mM $Na_2MoO_4$, 20 nM okadaic acid, were added). The activity of AMPK in the cells was detected at the level of phosphorylation of molecules by a conventionally known SDS electrophoresis and a western blotting which uses an anti-phosphorylation AMPK antibody (Phospho-AMPK-α(Thr172) Antibody, Daiichi Pure Chemicals). In this case, in order to confirm that there is no difference in the amount of protein of AMPKα (an AMPK subunit which undergoes phosphorylation) among samples, a western blotting which uses an anti-AMPKα antibody (Daiichi Pure Chemicals) was simultaneously carried out. As a result, as shown in FIG. 4, it was observed that the phosphorylation level of AMPK was significantly accelerated and activated in each of the aforementioned empty vector-transferred cell and the cell in which LKB1 was expressed by transferring pcDNA-LKB1, when treated with phenformin, in comparison with the case of treating with the solvent. However, in the cell in which human ATP5B was expressed by transferring pcDNA-ATP5B, activation of AMPK by phenformin treatment was not found. When the same test was carried out by adding 10 mM in final concentration of metformin (Sigma) instead of phenformin, activation of AMPK was not found in the human ATP5B-expressed cell similar to the case of phenformin treatment.

These mean that the AMPK activation ability contributing to the drug effect of phenformin, metformin or the like biguanide changes when the amount of ATP5B protein presenting in the cell is changed, and show that ATP5B is evidently positioned at the upstream of AMPK in the intracellular signal of biguanide. When both of this fact and another fact that biochemical binding of ATP5B and phenformin was shown by the aforementioned example are considered, it can be concluded that ATP5B binds to biguanide, and is the true target protein which contributes to the drug effect of said compound. In this connection, the phenomenon in which activation of AMPK by biguanide, namely acceleration of phosphorylation, was obstructed by the over-expression of ATP5B can be explained by either one of the following theories. It can be explained by a mechanism in which ATP5B originally has an action to suppress phosphorylation of AMPK, and biguanide activates AMPK by binding to ATP5B and thereby preventing its AMPK suppressing action. Alternatively, it can be explained that since the ATP5B molecule which acts by forming a complex with an endogenous molecule was over-expressed alone, biguanide was purged (removed) by binding to excess monomer of ATP5B, and as a result, acceleration of phosphorylation of AMPK originally generated by biguanide via a complex including ATP5B was not found. In this connection, such a phenomenon in which actions of compounds are offset each other by over-expression of a target protein is generally known and is also used as a means for identifying that a specified protein is a target protein of a compound (Curr. Genet. 2002; 41 (3): p. 142-149, *J. Biol. Chem.* 2005; 280 (13): p. 12231-12238, *Proc. Natl. Acad. Sci. USA* 1996; 93 (21): 11919-11924, *Yeast*, 1998 14 (10): 935-942). By either one of the above explanations of theories, there is no change in the fact that ATP5B is the target protein which contributes to the drug effect of biguanide, and that the substance which binds to ATP5B has the same drug effect (principal effect) of biguanide.

Based on the above results, it was shown that a compound which can induce the same principal effect of the drug effect produced by biguanide as an agent for treating diabetes, by making use of the same intracellular signal pathway, (namely an agent for treating diabetes) can be selected by making use of the polypeptides for tool use including ATP5B as the target protein of biguanide as an agent for treating diabetes (namely using as a screening tool of an agent for treating diabetes).

In addition, it was proved that a target protein of an agent to be tested, which contributes to the principal effect of the compound, can be identified by the identification method of the present invention.

Example 6

Method for Screening for an Agent for Treating Diabetes Making Use of a Polypeptide for Tool Use (1) Screening Method A screening method which can select a substance to be tested (namely an agent for treating diabetes) that binds to a polypeptide, using biguanide and ATP5B as one of the polypeptide for tool use, and using a change in the binding of said polypeptide and biguanide as the index, is shown.

Binding of ATP5B and biguanide can be detected in accordance with the aforementioned Example 5(4). As sown in FIG. 5, when concentration of MTX-phenformin (1.0, 10, 100 μM) to be present is increased in the method described in Example 5(4), its binding to the ATP5B protein was clearly detected. When free phenformin (10 μM) was added to this system as a substance to be tested, it was shown that binding of said protein and MTX-phenformin is obstructed as shown in FIG. 6. When the phenformin added in this case is replaced by a test substance desired to be evaluated, whether or not said test substance exerts a change in the binding of ATP5B protein and MTX-phenformin (biguanide) can be examined, and a substance which competitively inhibits binding of biguanide and a polypeptide for tool use and binds to the polypeptide for tool use, namely an agent for treating diabetes, can be screened. When, among the conditions described in the above, concentration of MTX-phenformin is 10 a substance having an IC50 value of 10 μM or less, preferably a substance of 1 μM or less, more preferably a substance of 0.1 μM or less is selected as an agent for treating diabetes.

(2) Screening of an Agent for Treating Diabetes

In accordance with the screening method of the aforementioned (1), screening was carried out by adding various compounds as the substances to be tested instead of free phenformin under a condition of 10 μM in concentration of MTX-phenformin (MTX-PH), and 2 compounds, 2-[(E)-(1H-1,2,4-triazol-3-ylimino)methyl]phenol (Maybridge, to be referred to as compound A hereinafter) and 6-chloro-9H-purine-2-amine (Aurora, to be referred to as compound B hereinafter), were found as a result thereof as hit compounds. That is, as shown in FIG. 7, it was shown that these 2 compounds obstruct binding of ATP5B and MTX-phenformin by the addition of 10 thereof. In addition, each of these compounds showed a significant AMPK activation ability by the AMPK activation ability detection test shown in the aforementioned Example 5(7), and this activation ability disappeared by the over-expression of ATP5B similar to the case of phenformin and metformin shown in the aforementioned Example 5(7). These results show that both of the aforementioned compound A and compound B activate intracellular AMPK by directly interacting with the biguanide-binding site of ATP5B. At the same time, it was confirmed that a compound having the AMPK activation ability similar to that of biguanide can be actually selected by the screening method of an agent for treating diabetes which uses the polypeptide of this description, shown in Example 6(1).

Example 7

Hypoglycemic Action of the Hit Compounds and Measurement of their Influence Upon Blood Lactic Acid Level As described in the aforementioned Example 6, the compound A and compound B found by the screening method of the present invention have the ability to activate AMPK in cells. Next, whether or not these compounds have the in vivo hypoglycemic action similar to the case of biguanide was examined. At the same time, action of the aforementioned 2 compounds on the increase of blood lactic acid value as an adverse side effect of biguanide was also examined. A total of 15 animals of 11 weeks of age of db/db mouse (BKS.Cg-+Leprdb/+Leprdb/Jcl; CLEA Japan) as a diabetes model mouse were divided into 3 groups, each consisting of 5 animals. Each of metformin (Sigma) and the aforementioned compound A was dissolved in a solvent (5% Cremophor, 0.2% methyl cellulose: MC) to a concentration of 30 mg/ml or 10 mg/ml. Metformin was administered at a dose of 300 mg/kg body weight, and the compound A at 100 mg/kg body weight, to the abdominal cavities of respective 5 animals of the aforementioned mouse, and compared with a group to which the same volume of the vehicle (5% Cremophor, 0.2% MC) alone was administered. They were subjected to fasting at the same time with the administration, and blood samples were collected from the tail of each animal 0 minute, 90 minutes and 180 minutes thereafter to measure blood sugar level and blood lactic acid level. The blood sugar level was measured using a simplified blood sugar analyzer (Acu Check Active II; Roche), and the blood lactic acid level was measured using a simplified lactic acid analyzer (Lactate Pro; Arkray Marketing), respectively. In the same manner, 12 animals of the db/db mouse of 18 weeks of age were divided in 3 groups, 4 animals for each. Each of metformin (sigma) and the aforementioned compound B was dissolved in physiological saline to a concentration of 30 mg/ml or 9 mg/ml. Metformin was administered at a dose of 300 mg/kg body weight, and the compound A at 100 mg/kg body weight, to the abdominal cavities of respective 4 animals of the aforementioned mouse, and compared with a group to which the same volume of the vehicle (physiological saline) alone was administered. In the same manner as the above, they were subjected to fasting at the same time with the administration, and the blood sugar level and blood lactic acid level were respectively measured 0 minute, 90 minutes and 180 minutes thereafter in the same as described in the above.

As a result, in comparison with the vehicle administration group, metformin shoed significant hypoglycemic action after 90 minutes and 180 minutes in each test. Each of the compound A and compound B showed the hypoglycemic action after 90 minutes and 180 minutes having a significant difference (FIGS. 8A and C). On the other hand, significant increase in the blood lactic acid level was found in the metformin administration group after 90 minutes in each test, but both of compound A and compound B did not induce increase of the blood lactic acid level (FIGS. 8B and D). Based on this result, it was confirmed that a new therapeutic agent for diabetes having significant hypoglycemic action similar to that of biguanide can be found in reality by the screening method of the present invention. In addition, since both of the aforementioned two species of compounds do not induce increase of blood lactic acid level known as an adverse side effect of biguanide, it was confirmed that screening of a new therapeutic agent for diabetes, which has the principal effect (pharmacological action of biguanide; namely diabetes treating effect) but does not have an adverse side effect (namely, increase of blood lactic acid level) can be carried out by the screening method of the present invention.

Example 8

Identification of Target Protein of Thalidomide Using Molecular Chaperone

Thalidomide has significant drug effects for sleep inducing agents, multiple myeloma, HIV, Hansen's disease and the like, but direct target protein of thalidomide has so far been unclear. Accordingly, an attempt was made to screen a target protein of thalidomide using the method shown in the aforementioned "Example 2(2). A human monocytic cell line THP-1 (ATCC) was cultured and suspended in 60 ml of a minimum essential medium (RPMI 1640, Invitrogen) containing 10% fetal calf serum (FCS) and cultured on a plate of 10 cm in diameter (Asahi Techno Glass) until reached $10^6$ cells/ml. The cells were collected by 3 minutes of centrifugation at 1200 rpm, washed once with 10 ml of ice-cooled PBS and then lysed by adding 2.0 ml of the aforementioned buffer A, and the cell extract was collected. This cell extract was centrifuged at 1500 rpm for 5 minutes to discard the precipitate, and the soluble fraction of supernatant was collected. Under a condition of adding or not adding 100 μM in final concentration of thalidomide ((−)-thalidomide, Sigma), a pull-down test was carried out by mixing this soluble fraction of cell extract with 8 species of GST fusion chaperone proteins purified on the glutathione Sepharose beads (a mixture of GST-HSPA1A, GST-HSPH1, GST-HSPCA, GST-HSPD1, GST-DNAJA1, GST-HSPB1, GST-HSPE1 and GST-HSPA4; respective proteins were mixed in 0.5 μg portions). In this connection, steps and conditions of the pull-down test were the same as the aforementioned Example 2(2). That is, after shaking at 4° C. for 1 hour, proteins binding to the GST fusion chaperone protein mixture on beads were co-precipitated. In the same manner as in the aforementioned Example 4, each molecular chaperone protein and beads were used by chemically crosslinking them in advance by a conventionally known method. After co-precipitation of the proteins binding to the chaperone protein mixture, the residue was suspended in 0.5 ml of the aforementioned buffer A' to which 100 μM in final concentration of thalidomide had been added or not added, and again co-precipitated by centrifugation. After repeating this operation 4 times, proteins in the precipitate were separated by SDS polyacrylamide gel electrophoresis in accordance with a known method, and the proteins were detected by a negative staining method (Wako Pure Chemical Industries. As a result, the presence of two or more protein bands which are present only when thalidomide was added was detected. These proteins are a group of proteins in which binding of said proteins and the molecular chaperone protein mixture was changed by the addition of thalidomide, namely a group of proteins in which their tertiary structures were changed by the addition of thalidomide. These bands were cut out, the proteins were digested into fragments using trypsin, and then the thus formed peptide mixtures were recovered from the gel and subjected to the identification of proteins by mass spectrum analysis in the same manner as the method of Example 4. As a result, it was revealed that the protein contained in a band of about 45 kDa which is present only when thalidomide was added is TARDBP (RefSeq accession number NP_031401).

Example 9

Inspection of Thalidomide-Response of TARDBP

It is known that TARDBP is a transcription factor having the activity to bind to DNA, RNA and the like nucleic acids and has an action to suppress HIV (Ou S H et al., *Virol* 1995 June; 69 (6): 3584-3596). Since a significant anti-HIV action of thalidomide is known (Franks M E et al., *Lancet* 2004; 363 (9423): 1802-1811), there is no inconsistency in thinking that TARDBP is a target protein of thalidomide.

Though a protein as direct target of thalidomide has not been known yet, it has been reported that it suppresses production of tumor necrosis factor α (TNF-α) or the like cytokine from cells (Franks M E et al., *Lancet* 2004; 363 (9423): 1802-1811). Thus, an attempt was made to inspect whether or not the target protein of thalidomide, TARDBP, found by the method of the present invention in the aforementioned Example 8 is the true target molecule carrying the principal effect of thalidomide, by carrying out an experiment using a change in the production of TNF-α from a cell as the index.

(1) Cloning of TARDBP Gene and Preparation of TARDBP Expression Plasmid

In accordance with the gene sequence of human TARDBP in the RefSeq accession number NM_007375, primers having the nucleotide sequences represented by SEQ ID NO:93 and SEQ ID NO:94 were synthesized, and an attempt was made to amplify complete length cDNA of human TARDBP by PCR from a human lymphocyte-derived cDNA library (Clontech) using said primers. The PCR was carried out using a DNA polymerase (TAKARA LA Taq; Takara Shuzo), by heating at 94° C. (3 minutes) and then repeating 35 times of a cycle consisting of 94° C. (30 seconds), 58° C. (1.5 minutes) and 72° C. (4 minutes). As a result of separating the PCR product by an agarose gel electrophoresis, it was confirmed tat a DNA fragment of about 1250 base pairs was amplified. Accordingly, this DNA fragment in the reaction liquid was cloned into an expression vector (pcDNA3.1/V5-His-TOPO; Invitrogen) using TOPO TA Cloning System (Invitrogen). The primer used in this case, represented by SEQ ID NO:94, was designed in such a manner that the stop codon of said gene was removed so that a vector-derived V5 epitope (derived from the V protein of paramyxovirus SV5, Southern J A, *J. Gen. Virol.* 72, 1551-1557, 1991) and a His 6 tag (lindner P, *BioTechniques* 22, 140-149, 1997) are continued in the same frame of TARDBP gene triplet on the 3' side after the cloning. Nucleotide sequence of the inserted DNA fragment in the thus obtained plasmid was determined using primers which bind to the T 7 promoter region on the vector (TOPO TA Cloning kit; Invitrogen; SEQ ID NO:89) and a sequencing kit (Applied Biosystems) and a sequencer (ABI 3700 DNA sequencer; Applied Biosystems). As a result, it was confirmed that it is a clone comprising the complete length cDNA coding for the human TARDBP, shown by the RefSeq accession number NM_007375 (SEQ ID NO:95). Hereinafter, this expression plasmid is referred to as pcDNA-TARDBP.

(2) Preparation of TARDBP High Expression Cell and Measurement of TNF-α Expression in Said Cell The pcDNA-TARDBP or an empty vector (pcDNA3.1) (Invitrogen) was transferred into HeLa S3 cell. Illustratively, the HeLa S3 cell (ATCC) was firstly cultured in a 12 well culture plate until it reached a state of 70% confluent, by adding 1 ml of a minimum essential medium DMEM (Gibco) containing 10% fetal bovine serum (Sigma) to each well of the culture plate. The medium was substituted by 0.5 ml per well of a serum-free medium OPTI MEM I (Invitrogen), and 0.8 μg/well of the pcDNA-TARDBP or pcDNA3.1 was transiently transferred using Lipofect amine 2000 (Invitrogen). After 12 hours of the culturing, this was substituted by 1 ml/well of DMEM containing 10% of fetal bovine serum and further cultured for 12 hours. This was further cultured for 16 hours under a condition of adding or not adding okadaic acid (Wako Pure Chemical Industries) to a final concentration of 50 nM. In this case, 100 of thalidomide was added a part of the cells simultaneously with the okadaic acid treatment. The medium was discarded, the cells were washed twice with ice-cooled PBS, and then these cells were frozen and stored at −80° C.

(3) Measurement of TNF-α Expression in Cells

Total RNA was prepared from each cell frozen in the aforementioned Example 9(2), using a reagent for RNA extraction use (Isogen; Nippon Gene) and in accordance with the instructions attached thereto. The thus prepared each total RNA was then treated with a deoxyribonuclease (Nippon Gene), subjected to phenol/chloroform treatment and ethanol precipitation and dissolved in sterile water. Using 1 μg of this total RNA, its reverse transcription into a single-stranded cDNA was carried out in a system of 20 μl using a kit for reverse transcription reaction use (Advantage™ RT-for-PCR Kit; Clontech).

Six oligonucleotides (SEQ ID NO:97 to SEQ ID NO:102) were designed and synthesized as primers of PCR for the measurement of gene expression quantity. A combination of SEQ ID NO:97 and SEQ ID NO:98 was used for human β-actin gene, and a combination of SEQ ID NO:99 and SEQ ID NO:100 for human TNF-α gene, and a combination of SEQ ID NO:101 and SEQ ID NO:102 for human TARDBP gene, respectively.

Real time measurement of PCR amplification by PRISM™ 7700 Sequence Detection System was carried out in a system of 25 μl using the aforementioned 6 species, 3 sets of primers and in accordance with the instructions attached thereto. In each system, 5 μl of single-stranded cDNA, 12.5 μl of 2×SYBR Green reagent and 7.5 μmol of each primer were used. In this case, the single-stranded cDNA stored in (2) was used bi diluting it 100 times. In this connection, 0.1 of a human genomic DNA (Clontech) was diluted and a 5 μl portion thereof was used instead of the single-stranded cDNA. The PCR was carried out, after heating at 50° C. for 10 minutes and subsequent 95° C. for 10 minutes, by repeating 45 cycles of a process consisting of 2 steps of 95° C. for 15 seconds and 60° C. for 60 seconds.

The expression quantities of human TNF-α gene and human TARDBP gene in each sample were corrected by the expression quantity of β-actin gene based on the following equation.

[Corrected expression quantity of TNF-α or TAR-
DBP]=[expression quantity of TNF-α or TAR-
DBP gene (raw data)/[expression quantity of
β-actin gene (raw data)]

In comparing the expression quantities of TNF-α and TARDBP genes, relative amounts were calculated by regarding the expression quantity in a cell, into which an empty vector (pcDNA3.1) was transferred and which was treated only with the solvent (DMSO), as 100, with the results sown in FIG. 9 and FIG. 10. The values in the drawings represent average±SE.

As shown in FIG. 9, it was confirmed that expression quantity of TARDBP was accelerated in the cell transferred with pcDNA-TARDBP (TARDBP high expression cell) by a factor of about 7 times in comparison with the empty vector-transferred cell (control cell).

As shown in FIG. 10, it was observed that expression of TNF-α from the control cell is sharply increased (up to 80 times) by the okadaic acid treatment. Since the addition of thalidomide suppressed this expression acceleration of TNF-α by okadaic acid close to 50%, it was confirmed that the action of thalidomide can be detected in said cell.

On the other hand, in the case of the TARDBP high expression cell, the action to accelerate expression of TNF-α from the cell by the addition of okadaic acid was almost the same in comparison with the control cell, but the action to suppress expression of TNF-α by the addition of thalidomide was not observed. This result can be easily explained based on an assumption that the thalidomide which should act originally was purged (removed) from inside the cell due to the binding of thalidomide in the cell and excess amount of TARDBP protein caused by the over-expression of TARDBP. It is known that TARDBP is a transcription factor which has the activity to bind to DNA, RNA and the like nucleic acids. That is, since TARDBP is considered to be one molecule in a functional complex consisting of two or more transcription factors essential for the expression induction of TNF-α, it is considered that expression induction of TNF-α is not accelerated when the molecule alone is over-expressed, but when the function of said molecule is inhibited by thalidomide, function of the transcription complex essential for the expression induction of TNF-α is lost, and as a result, production of TNF-α is suppressed.

Based on the above results, it was considered that the protein TARDBP which binds to molecular chaperon only when thalidomide is added, found by the identification method of the present invention, is a molecule concerned in the expression control of TNF-α considered to be one of the molecular mechanisms carrying the drug effect of thalidomide.

Based on this, it was proved that the identification method of the present invention can be used for the identification of target proteins without applying modification of agents to be tested, in addition to the identification of the biguanide target ATPSB shown in the aforementioned example.

INDUSTRIAL APPLICABILITY

The screening method of the present invention can be applied to the screening of an agent for treating diabetes. The screening tool of the present invention can be used in the aforementioned screening.

The identification method of the present invention is useful as an identification method of target proteins which are useful in studying improvement of existing agents.

While the invention has been describe with reference to specific embodiments thereof, changes and modifications obvious to those skilled in the art are included in the scope of the invention.

SEQUENCE LISTING FREE TEXT

Explanation of "Artificial Sequence" is described in the numerical heading <223> in the following Sequence Listing. Illustratively, respective nucleotide sequences represented by SEQ ID NOs:28 to 77, 84 to 89, 91 and 92 of the Sequence Listing are artificially synthesized primer sequences.

The invention claimed is:

1. A method for screening for an agent for treating diabetes, which comprises:
   (a) allowing a polypeptide consisting of the amino acid sequence of SEQ ID NO:2, or a polypeptide which comprises the amino acid sequence of SEQ ID NO: 2, to be in contact with a substance to be tested in the coexistence of biguanide;
   (b) analyzing binding of said polypeptide with the substance to be tested;
   (c) verifying binding of said polypeptide and biguanide is inhibited; and
   (d) selecting the substance which binds to said polypeptide in competition with biguanide as an agent for treating diabetes.

2. The method for screening of claim 1, which further comprises:
   (a) analyzing whether the substance which binds to the polypeptide activates AMPK activity; and
   (b) selecting the substance which binds to the polypeptide and activates AMPK activity as an agent for treating diabetes.

3. The method for screening of claim 1, which further comprises:
   (a) analyzing whether the substance which binds to the polypeptide, has a therapeutic activity for diabetes; and
   (b) selecting the substance which binds to the polypeptide and has the therapeutic activity for diabetes as an agent for treating diabetes.

* * * * *